(12) United States Patent
Tan et al.

(10) Patent No.: US 8,014,954 B2
(45) Date of Patent: Sep. 6, 2011

(54) METHODS FOR CHARACTERIZING AGONISTS AND PARTIAL AGONISTS OF TARGET MOLECULES

(75) Inventors: Yejun Tan, Seattle, WA (US); Hongyue Dai, Kenmore, WA (US); Pek Yee Lum, Seattle, WA (US); John Ryan Thompson, Scotch Plains, NJ (US); Joel Peter Berger, Hoboken, NJ (US); Eric Stanley Muise, New York, NY (US); Richard F Raubertas, Essex, VT (US); Kenny Kin Chung Wong, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1494 days.

(21) Appl. No.: 11/397,327

(22) Filed: Apr. 4, 2006

(65) Prior Publication Data

US 2006/0240457 A1    Oct. 26, 2006

Related U.S. Application Data

(60) Provisional application No. 60/668,773, filed on Apr. 5, 2005.

(51) Int. Cl.
   *G01N 33/48* (2006.01)
   *C12Q 1/68* (2006.01)
   *G06G 7/58* (2006.01)
(52) U.S. Cl. .................. 702/19; 435/6; 702/20; 703/11
(58) Field of Classification Search ...................... None
   See application file for complete search history.

(56) References Cited

U.S. PATENT DOCUMENTS 6,294,559 B1 * 9/2001 Smith ........................... 514/369

FOREIGN PATENT DOCUMENTS

| WO | WO 99/37817 | * | 7/1999 |
| WO | WO 02/059560 | * | 8/2002 |

* cited by examiner

*Primary Examiner* — Shubo Zhou
(74) *Attorney, Agent, or Firm* — Christensen O'Connor Johnson Kindness PLLC

(57) ABSTRACT

In one aspect, the present invention provides methods of determining whether an agent is more like a partial agonist of a target molecule than a full agonist of the same target molecule. In another aspect, the present invention provides methods to select a candidate compound that may reduce blood plasma glucose concentration in a mammal. Populations of genes are provided that are useful in the practice of the present invention.

19 Claims, 1 Drawing Sheet

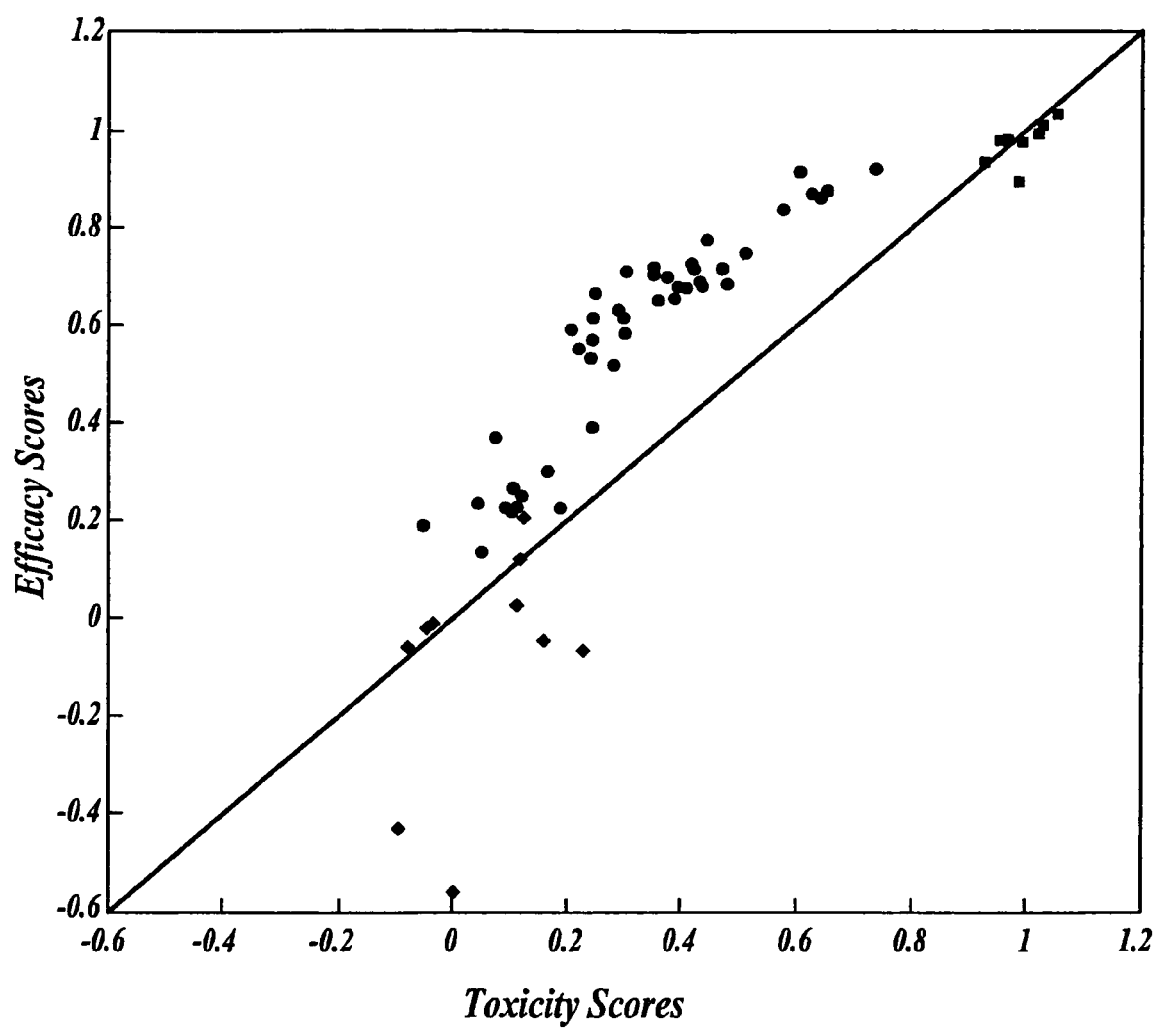

SEQUENCE LISTING

<160> NUMBER OF SEQ ID NOS: 86

<210> SEQ ID NO 1
<211> LENGTH: 504
<212> TYPE: DNA
<213> ORGANISM: Mus musculus

<400> SEQUENCE: 1

```
ccgactcctg tcccagccac cgtcagccac agtcgcagcc ggacctcgct cctcaacttg     60
aagcaaaaat gcctacagag actgagagat gcattgagtc cctgattgct gttttccaaa    120
agtacagcgg gaaggatgga aacaacactc aactctccaa aactgaattc ctttccttca    180
tgaacacaga gctggctgcc ttcacaaaga accagaagga tcctggtgtc cttgaccgca    240
tgatgaagaa gctggacctc aactgtgacg ggcagctaga tttccaagag tttctcaacc    300
tcattggtgg cttagctata gcgtgccatg attctttcat ccaaacttcc cagaagcgaa    360
tctaatcctc ttagttccat ccaaccacca agtcatcacc tcccccgacc ccatccacac    420
ctgcactgag cccagcacac ctaccacaac atgtatccca cgcctgctgg caaaaataaa    480
acaatgccat ttttttttaa atgt                                           504
```

<210> SEQ ID NO 2
<211> LENGTH: 837
<212> TYPE: DNA
<213> ORGANISM: Mus musculus

<400> SEQUENCE: 2

```
ggaaaaatct tacaggatcc agaacaaaca aacaaacaaa aaaaaaaaac cctcttagaa     60 tgaatttttac ttttgaagta atggtttata ttttgaaatt gtatttaaga atcctaaaaa   120
ttaagggttg agttctatca taactttctg aaaggacact gttaaaatac tgctctgtgc   180
atatatgaag ctcagaatag tgagcttagt ttaattatct ctgatcattt ttggtcctgc   240
acatacggaa tatctctgtt aagaggagga gaccgtgtca tatcactggg tagacaggta   300
cccattacct tagcaagtat gtttagtgct cagtgagcgt ttcagacact gtcaagcttc   360
tgctgcacaa aagctccaat ggtaatatgt tataacagtt gaggaagaac ttatgtgctg   420
tttaatgttc tctgaagcct gtgtatgcag tctcatcctg ttttcagtga gggcacttga   480
tttatgtctc atcaccacca ttcctattga aaatgttgct caaagactca catggtgcaa   540
atagtgtggt atgccacatt ttcatgtaag tgcagtagta tcacacagcc tgatgatggg   600
ataggaatgt tctagtgtca ctttcttagt tgatgctgtt tggtgaaatg gttatctgtg   660
```

-continued

```
ttttattcaa aaggctggtg atattgatgt acttagtgaa gtatctttta ttttttatttt    720 tctttaggaa aaatatctag gaaaacatga tatgaaaatt atattcactt cattgtagtg    780
tagcattttc atgtatggca gtgcctgtgt gaaggagttg tagaaatgcc ctgtccg       837
```

<210> SEQ ID NO 3
<211> LENGTH: 1775
<212> TYPE: DNA
<213> ORGANISM: Mus musculus

<400> SEQUENCE: 3

```
gaaaggcgtg gtgagcgaca gaacgatggc ggacgcggag aaaaacgctg ttgcggagaa     60
aaacaacgct gttgcgacga aagaggttct ggctgaggca gcagccattc tagaacctgt    120
aggcttgcag gaagaagcag agctgcctgc caagatcatg gaggagttta tgaggaactc    180
gcggaagaaa gacaaactgc tctgtagcca gcttcaagta gtgaacttct tacagacttt    240
tctggctcag gaggacactg agcagagccc tgatgctctg gcttctgaag atgccagtcg    300
gcaaaaggca actgaaacta aggagcagtg gaaggacatg aaggccacat acatggatca    360
cgtggatgtc ataaaatgtg ccctgtctga ggccttaccc caggttaaag aggctcacag    420
gaagtacaca gagcttcaga aggcttttga gcaactcgag gctaagaagc gagttcttga    480
ggagaaactt cagctggctc agaagcagtg ggtactgcaa cagaagcgtt tgcagaacct    540
gacaaagatt tctgcagagg tcaagaggcg ccggaagagg gctctggaga gcttgacgg    600 atcccatcag gaactggaaa ccttgaagca gcaagcgggg caggaacagg agaagctgca    660
gaggaaccag agctacctcc agctgctgtg ttcgctgcag aataagctgg tcatctctga    720
gggcaaggct gaggacaaag atgtgaaagg gcgagccctt acagccaaat cctaatctcc    780
ttatagatga aaggatgaga agagagccgt attcataccc tgcttgggct gagaccagat    840
tggtttcttc actgttgtat ctctaggcct aagcctggag tttgttgctc tgtacatcta    900
atctccagct gatcacatct ggcatctctt gctttcagtg actgttgtgt tttgtctcat    960
gctaactttg acagtatatt ctggcttgtt ctgtcttcac ctgtgtctaa cttgctgtcc   1020
ttgcaacctg tctctgtaaa agtgtaccag tgatactcac acgcatgcat gcacgcacac   1080
aggcacgcat gccacaacca ccctttttctc tcgctgatct tcagtagtct ctcctcttgt   1140
cctctctttt tctttgtctt ctctccctac cagatgtgaa agcaacttta tgcgcctgct   1200
gtaattgttg tctgaggatt actgcgagta agctcaccct ttgtagttac taaactggcc   1260
ggctggctgg gtcagtccgc tgtactggtt cataacccgg cttcaagttg actgattcaa   1320
agggccctct cttggcttct gactgaactg ctctgcttgg aaagtctgat ggacttcagg   1380
aacagaactg tactgactgc cctgactcag ctgaactcaa ctacaccaaa ttcattggtt   1440
ctctctgctg tactgctctt aggtagcctc tctcctgtgc tgtcctcctg agtcgtgctg   1500
tcaaatctct ctctgattca tcactttgcc cctcaattag actggcagtt tcaaacacgg   1560
cacttaacat ttcagttgta gtcacttgat actgcattcc gaacttgagt ctattgaatc   1620
cagaatgtga atccatgcct ttgtgactgt gacctcactc tcttcagtat tgtgtaaaag   1680
ttttaggaac tctccaagta aatacttggt aattgctcat tgatagaaca gaaaaatgct   1740
gtgtagataa taaataaaca tataactata agatt                              1775
```

<210> SEQ ID NO 4
<211> LENGTH: 1533
<212> TYPE: DNA
<213> ORGANISM: Mus musculus

<400> SEQUENCE: 4

```
gtcttcgggg cgtgagaagc cggcaaacat ggcggccccc tgcttcctca ctctgcgggt    60
ggctaccctg gccgccttgg cgctcttgtc tctcggcagc tctgccgctg acacatcga    120
ggatcaagcc gaacagttct ttagaagtgg acacacaaat aactgggctg ttttggtgtg   180
cacatcccga ttctggttta actaccgaca tgttgcaaat actctttctg tttatagaag   240
cgtcaagagg ctaggtatcc cggacagtca cattgtcctg atgcttgctg atgacatggc   300
gtgcaatgct cggaaccccca agccagccac agtgttcagc cacaagaaca tggagctcaa   360
tgtgtatgga gacgatgtgg aagtggacta cagaagctat gaggtaactg tggagaactt   420
tttaagggta ttgaccggga ggggttccac ccagtacccc tcgctcaaag cgtcttcttt   480
ccgacgacag aagcaatatc ctcatttata tgacaggtca tggagggaat ggtttcttga   540
aattccaaga ttctgaagaa atcaccaaca tagaacttgc agatgcgttt aacagatgt    600
ggcagaagag acgctacaat gagctgctgt tcattattga acttgccag ggcgcgtcca    660
tgtacgagcg gttctactct cctaacatca tggccttggc tagtagccag gtgggagagg   720
attcgctgtc gcaccagcct gaccctgcga ttggagttca tcttatggat aggtacacgt    780
tttatgtctt ggaattttg gaagaaatta tccagctag ccaaactaac atgaacgacc    840
ttttttcaagt gtgtccccaa agtctctgtg tgtcgacccc tggacatcgc actgaccttt   900
tccagcgaga tccaaaaaat gtcgtgatca ccgatttctt cggaagtgtg cgcaaggtgg   960
aaatcacaac agaagagatc agtttgcagt gggattcaca agtcgtggac agcagttcta  1020
aagaagacgg cacggccgag gagcgcatgg gacctctcaa gtatgctgag cagctcccgg  1080
tggctcagat aatacaccag aagccaaagc cgagagactg gcaccctccc ggaggcttca  1140
tcctggggct gtgggcgctc atcatcatgg tcttcttcaa gacctatggg atcaagcata  1200
tgaagttcat tttctaagac tcaaggatgt atgaggaaga atgaatggaa gactgcagcc  1260
ttggagcaaa acttaggttt tcatatgttt ttaaatatgt tgcttttgtg taaatttggg  1320
aagaaaatta ggaaaattga atattaatga acttttgact ttaaaacata atattgttaa  1380
tgcacttgtt tactggccac agaatatatc tttcattgtg tttgtgtgtt tgagttatag  1440
aaagcagaga gcaatgacat tggaacttta tgcttaattc ttttttaccct cctctcattg  1500
taaaagtgag tagtaaaggt gttagttccc acc                               1533
```

<210> SEQ ID NO 5
<211> LENGTH: 1484
<212> TYPE: DNA
<213> ORGANISM: Mus musculus

<400> SEQUENCE: 5

```
gagagagctc ccagggagct gagctgatcg cctttgtgta cagagggaag agacggtggc    60
gtgaccccac ccgggaagcc ccgcggcagg aacaatgcta gcctgcttga cccgcgggaa   120
cttactggac gtcctgcaag agggcttcaa tgagcaacag ctacaggcct acgtggcctg   180
ggtgaatgcc cagctgaaga gaggccatc cgtgaagcct gtgcaggacc tcgacagga    240
tctccgagat ggggtgatcc tggcctatct catcgagatt gttggtcagt tggccttgga   300
ctctgatgct agtgtagacg agagaactga cttctttctt ctccattcgc ccttcaaagc   360
aggttgttcc ttcttagaa tgcatggcaa cagcgtcggg aaatacctaa agtacttgc    420
cctggttaat ctacgtgttg gtcaataaat gctgtgtgcc aggtgctgta ttgtatggga   480
agatgttaac tctgccagtg ccctcagagg ttcctagtct aattgaaaag actggagagt  540
```

```
gaggtctgtt ttattactgt ccttagtatt ctgatggagg gaggcagagg aggatacata      600
gaagagatgc cctccttagt cctagggctc aggaatggca gaccagaaga attagtgtct      660
gaatagggaa ggacaacatc cagaagaact gctgtctgaa ttaaaagaca gaagtgggat      720
ggctagaaag ttggctcagc cattgagaac acaggctgct ctagcagagg acctgggttc      780
aattcctagc acccacgtag cagccgacaa ccagtcccag gggaacccac actttttct       840 gcacaatata catgcaggca aaacactcac acacacacac acacacacac acacacacac      900
acacacacac acacacatgg gggtggcggg agaagaaaca acaggagta gcattcaggc       960 caaaagagaa aatgtcacca gcaaaaggac tggcctccat gacattcaga cccaagtgtt     1020 gaagggttt  gctcttcact tttggggctg ttcttcttat agcattatgc ccatgatgtt     1080
tgtccatagc ttgctatgat ttctctcccc tgactagcaa ttagccatga tttagactga     1140
gcttttaaag aggttgttac actgtatttt gcttttttgg ttccacgaac cctagtcgga     1200
tgcacagaat aagttctcca acatttatta ttggtcagtt gatgttgctt agtgtcccca     1260
gaggtctgtg gtgtggaggg agctgctttc cacaggcagc ctatctgtga atactttctt     1320
gtattcacga ggcagtagta accacggctg ctaggatgga atgctttcta tcttgtgtga     1380
attgatttgg ccatcatacc cttagaaaat agatattatc attcctgttt tcaggaaaca     1440
aaaggaaaaa tctataaaaa taaataaaga cttaagtatg tgtc                      1484

<210> SEQ ID NO 6
<211> LENGTH: 1960
<212> TYPE: DNA
<213> ORGANISM: Mus musculus

<400> SEQUENCE: 6
gaaaggagat tgatatttga aagacgagtt tgttctacct agcaccctag ctctagctct       60
gtcagatacg ttaatgcata catcctctct aatgcatgtt catttattgc tgcagtttgg      120
ttcttctgga gtattttcat catttagcta ttggaataca attatgaaaa ccaactgttg      180
aacatacttg gagtagctgt ttcttttccta aagaaccaaa gttgttttca gctaatagaa     240
caggttgaag tccgcctgca ttagctgtgt tttccctcat cttgttagag ggatgcacag      300
ggcacggtga catcatttcc ctcatgttgt tagagggatg cacagggcac ggtgacatca      360
tttgagggag gaaaattgtc gttaagaatt tccagtaaga tcaaacttaa taactgagat      420
tatgaaagca ttttatgtt ttcgatgata taaacaaaag tcaactcgtt tatagcaagg       480
tgaacaaacc ctaggttctc ttgaagttga tagtatttaa tgtatttga aaattaacct       540 ccattaatta aatctttct  ttgtggtagg gcctaccttc tgctttcctg gaaaagatga      600
atatacatca tatgaaccta ttttgagttt ttctgttgtt tgtttgccta attttgtttt      660
tatagcctaa aataaaaata tgacacagtt ttagctctca tgggatgctg tctcggtttg      720
tactgattga ggctattgca gagggttagt tggaattcag gggtgcctag ttttctatat      780
tgaacaacgc tggaggagct aatacacacg tgctttaaaa aaagtgatat gctctagttt      840
gagcagaaag gtacagttgt gcttgttaga actgaaacct tgtttggac  tttgtttatt      900 ctgtcctcag gaggatgagg agtgtcggga gccatgctgt ttatttactg tgcataacca     960
agaatgggtg ggactgttga ttcaactacc tcaactctgt taaggcatat ggggtatat     1020 ctcacaaact ctcagtctta cttgcaaaat gctcaaaaaa ttgggcctct ataccatgag     1080
tgtgatattc agcattatat tcacaccaag cttttgatgat taaactggag aatgaagttt    1140
aaacacttct attctagatc tgagcatgtg gctccaattt tagtgggaag gaatgaaagt     1200
```

```
agtgtatgat tcaagagat tgaagagttt tgggattttt gagttttacc cccttcaga    1260 tatttcaagt gaccacatta taaaacaccc taaggtggta acgaggcagg ggaggatggc    1320
atgaagttgc attaagtttc agaccactga gagccacatt taaataccct caggctaatt    1380
actgttcact ttggggcagg agtaggtttt gccagggtat agtaattgga ttgcactcca    1440
aggaaagttc ctattgttaa taaaatttac gtagaggaga aacgtttgtt tgaggtggta    1500
gttctttctg tgaggtttta gtattcgaac tcttagaatg tgaacacatt cgagagctga    1560
cttcttcctg agagttttaa ctactggaaa tccttaacca attatatttt ctttatttg    1620 agaatgattt ggttgctttt tcttagatgg tttctgctat tttctgtaat catagttcat    1680
ctaaacacag cctatttcg tgaacattga agtttgtaac ggaaagatag gatctcattt    1740
tcagtgaact tccagactag cgcactcttc ccttccctct gtaggaagta gctgttgcca    1800
aagcgaagag gtagctggct cttgtataat gggaaagtgc cgtgtggagc ttcaggggtc    1860
agtgtttatt atgacatctg tcagtcccca aatggttcta ttctctacaa gtctgaaata    1920
tgtaatctga atccttaat aaaattggat ctaattttat                           1960

<210> SEQ ID NO 7
<211> LENGTH: 1201
<212> TYPE: DNA
<213> ORGANISM: Mus musculus

<400> SEQUENCE: 7
aaattccacg aagataaaat gtgtgtagag agacctttgc ccagaggtgg cccactggaa     60
gacttgaggg tctttggggg aactaaggca atagggtgag gtaaaaggca gagtgtttgg    120
tggataaagg ccccaccaaa ataagcagaa ggcgggtaga gcctgggaaa gggtggtagg    180
tgtgtgggga gagggctta tttacaaagc tacaaaacct gcacacagga gcacgtgagt    240
tttctttgga aagagagagg aagctagaag agggttgaaa tggaattaga agaaatgcc    300 cttgttaaca acacaaagaa attcaagagt cccactttgg taggatctca agacagcagg    360
gcagcttccg ggtcaggagg gaagtcagtt ttagaaagtg tgttccaaag agacgtcagc    420
ctgattggat tctctcttcc agaatctagg aactgccttc cgggaagcct tgttttccat    480
gcccggaaaa ttagggttcc agcaggggc agcagcgagt tgtggagaac tggcagctgg    540
ggaaagcaag gtgcctctgg agctgagctc cctagctgga agctggagca gcagggccag    600
ctggcttgcc cacctaact ccctctcagc tgcttctacc atggatcttt ctctaatgtg    660
aaactttaga gcttgccaag accctcctgt gttccttgcc tttggggccc ccttttacctg    720 aaagttgggg agagtggggt gctgcttcat gtccaaggct tgatttctta tagttactga    780
ccaggttttc tcctaaggac acatttgttc cccctttaat ggctgatcag gagcaggcaa    840
cacctccccc aattgatagc tacaggctac ttccttctcc tcacctacat gtattccctg    900
cttcttagaa ttgtagctca ttgatatttt ggggtgggga gggatgaaa accacaaacc    960 ttttatacca tacaaagctt tgctttttat tttttatttt taattttttt tttcttggtc    1020
cccttccctc ctctgaatgc ttggagacgg agaagctgag gagggtgggt aagtgttgga    1080
tgaggtcctc tgtgctgatg ggtaatgtt gtgggcagat gcagtttcct gtgggctcta    1140
ggggagtccc ttgagttgct gtgttctggt gagcagccgg accaataaac ctgcttttct    1200
c                                                                    1201

<210> SEQ ID NO 8
<211> LENGTH: 1606
```

```
<212> TYPE: DNA
<213> ORGANISM: Mus musculus

<400> SEQUENCE: 8
gacttcactt ggtggaaaga gaaggaagga agcctagggc ttaacaggca ctggtcccca      60
agttcattgg tcatggctcc tcgttcacgg cggcgaaagc acaagaaacc cccaccagtg     120
attcccatga ttgaaatccc acccacagaa gtgtctccag tatctccagc cctctcaaaa     180
cctggcccta gcattgatgc acttggcttc atttccttgg acaataatgt accaggtctg     240
tcccagttga tcctccaaaa gctgaacatg aaaaactatg aagaatacaa gttggtgata     300
aatgggggaa ccccagtatc aagctttgga tttcgatgtc aacaagaaat gttccagaag     360
atggaggaca cattcagatt ctgtgcttat tgtaaagtgc tccctcatgg cctttccaat     420
tgcaaggttc tccggcactg taagaggtgc agaaatgtct attactgtga tacagagtgc     480
cagaggtcag attggccagc acataggaag gtttgtcgag agctccgtct tgtggctgta     540
gatcgtgtca tggaatggct tctggtcaca ggtgattttg tcctaccctc aggaccttgg     600
ccatggctac ctgaagatat acagaattgg atacctggt tttctatgag gggtttacag      660
ctagaatcta cattgaatgc tcttctgggt agtcactcta tgaccatgct ttgggcaagt     720
ctaggaaggc cacggccaga cccagatgtc ttgcatggct ctttgaagcg ttgatgaca      780
gatgttctgt cacggccctt gaccctgggc ttagggcttc ggactgtggc aatagatgtt     840
gggaagactg gaggaagcac attgcatgtg gttggtgctt cccacgtaga gacatttctt     900
attcgttctg gagattatga tgagcttggc tacatgtttc ctgaacaccct tggctttcat     960
gtgatcatgg tgggtgtgga tgtggctact gacctttac agagttcttc atctttatcc     1020
ttggagcctg gaacaattca gcttagtggc cacagggccc tgtatcatga cttctgggag     1080
gagcaaatag agactgggat tctggcccat ccagatttgg tggctgcatt ccatccaggt     1140
ttccatgcct ccccaggctt gatggaagct tggttaccca ccctgctgct acttcgtgac     1200
tatgagattc caacattgat tactgtttac agccaacagg aactggaagc ctctttgcag     1260
attctggtga acttggatac acacatcatt gcttgtggag ctaatccttt cgcatccctc     1320
aaaccagaac aagtctattc taatcccaac aagcaaccag tatacagcag tgcctactac     1380
atcatgtttc ttggaagttc ccctgccaat tagataagaa gcaacgagaa ggaaaaaaaa     1440
aaaaaacaaa accagatgat ttttcagtaa ttgaaccaag tctttactga atgcctggaa     1500
aatgaaagct taatcaactt accctgttga tgtcagattt ttgccagctt tgaaccctgt     1560
ggtatgctaa accttattca cagttcaaat aaagatgttt aaaccg                    1606

<210> SEQ ID NO 9
<211> LENGTH: 824
<212> TYPE: DNA
<213> ORGANISM: Mus musculus

<400> SEQUENCE: 9
ggggaagggg ccgaggtcca gctgactggg aaagtctggg atgaagccaa tgtaaaagca      60
caagaactgg ccacaaggga tggctgggtg aacgtctccc cgtttgacca tccccttata     120
tgggaaggcc atgccagcct agtgcgggag ctgaaggagt cactagggac ccctccaggt     180
gctgtggtgc tggccgtggg gggcggaggg ctcctggcag gtgtgactgc tggcctgctg     240
gaggtgggct ggcagcatgt gcccatcgtt gccatggaga cccgcggggc gcacagtttc     300
aattcggcct tgcaggcagg caggccggtc acctgccag acatcaccag tgtagccaag     360
agcctcggag ccaagacggt ggctgcacgg accttggagt gtgcaaagga gtgtgaggtc     420
```

-continued

```
ctctctgagg tggtagaaga ccgggaggct gtcagcgctg tgcagaggtt cctggacgat      480
gagcgcatgc tggtggaacc tgcctgcggt gccgccctgg ccgccatcta ctcgggcatc      540
ctgtggaggc tccaggctga gggccgcctg agttctgccc tagcttccgt tgtggtcatc      600
gtgtgcggtg gcaacaacat tagtagccaa cagcttcagg agctgaaaat ccagctgggc      660
tgcagctgaa gaatctcagg aactccccca gaggttcctg dacaccttgg tgggtcactc      720
aagggacctc ggttccagtg gtcctgccct cttccttcca ggtagccctc ctgggttgct      780
ctcagtggct ccctgctgtc cagtgaataa acctgactga gctg                      824
```

<210> SEQ ID NO 10
<211> LENGTH: 687
<212> TYPE: DNA
<213> ORGANISM: Mus musculus

<400> SEQUENCE: 10

```
ttagttgtca gccccagtcc acttccctcc ccacatcaag gaggaatgca tcctgagcag       60
ctgaccctgg agccacacag aatgtgggta cagaaggcac ccttggccac atcctcccca      120
cttaagacct ctgggatttc ttttggagta cctgaaggct cgcgaattg ctctaagcga       180 attgctattt tgagcaccca gcccagtcct tttctccacc cctcccaacc taaacccaga      240
cagttcatcc actcgttgcc ccacgccag tcccactctc acactcactc tgaagaagca       300
gcagtttcca cagcaggacg cgggacagca gctccatggc gcctgcgggg gacgtgcttt      360
gtcttactca gctctaactc tccagaaaaa cagccgaccc cctctccctg ccagcacccg      420
ctgacatcac ggagccctgg gccgggtctg gccccgccc actgcgctgc tcaactgctt       480
ggcctccccc atcttgactg gcctataatg ctgcaaacac cctgtccggg cccagttggt      540
gggagggtct gagtagaggc tcggccagtc actggtcagt cttggggagg agcagtagct      600
cagtcctggg acagaagacg aggcctggat gtgaagattc ctgaggccaa gcgggtgcca      660
agcatctggt aaacttcctg agtttcg                                         687
```

<210> SEQ ID NO 11
<211> LENGTH: 399
<212> TYPE: DNA
<213> ORGANISM: Mus musculus

<400> SEQUENCE: 11

```
atgattgaac ccttcttggg gacctggaaa ctggtctcca gtgaaaactt cgagaattac       60
gtgagggaac tgggagtgga atgtgaaccc cggaaagttg catgtttaat aaagccaagt      120
gttagcatta gtttcaatgg ggaaaggatg gacatccaag caggaagtgc atgcaggaac      180
acgaagatct ccttcaaatt gggggaagag tttgaagaga ccactgcaga caaccggaaa      240
gtgaagagcc ttataacttt tgaaggtggg tcaatgatcc agatccaaag atggcttggc      300
aaacagacaa caattaaaag aagaattgtg gatggaagaa tggtagtgga gtgcaccatg      360
aacaatgttg tcagcactag gacctacgaa agggtgtag                             399
```

<210> SEQ ID NO 12
<211> LENGTH: 1113
<212> TYPE: DNA
<213> ORGANISM: Mus musculus

<400> SEQUENCE: 12

```
gaggtagggt ttcgccagag accccggaag cgacggcttc tcgtctttgc taaggcttct       60 ggttttttgct acggtttctg atttcggctt tgggatgggt tgcgacggag gcaccatccc     120
```

| | |
|---|---|
| caagaggcac gagctggtga aggggccgaa gaaggtcgag aaggttgaca aagacgctga | 180 |
| actggtagcc caatggaact actgtaccct aagtcaggaa atcctgaggc gcccaatagt | 240 |
| tgcctgtgag cttggcagac tgtataacaa agacgcggtc atcgagtttc tgttggacaa | 300 |
| atctgctgag aaggccctgg ggaaggcggc atcgcacatc agaagcatca agaatgtgac | 360 |
| agagctcagg ctttctgaca accccgcctg ggaaggagat aaaggaaaca ccaagggcga | 420 |
| caagcatgat gacctccaga gagcgcggtt catctgccct gtggtgggcc tggagatgaa | 480 |
| tggccggcac aggtttttgct tcctccgatg ctgcggttgt gtgttttctg aacgcgcctt | 540 |
| gaaggagata aagctgaag tgtgtcacac gtgtggggct gccttccagg aggaggacat | 600 |
| cattgtgctc aatggcacca aggaggatgt ggagatgctg aagaagagga tggaggagag | 660 |
| gaggctgagg gccaagctgg aaaagaaaac aaagaaaccg aagacagcga ccgagtgtgc | 720 |
| gtcaaagccg gtaccacaca agattccgca gggccatcaa agtgaagtc tggcaagcct | 780 |
| gaggaggcga cccctgatcc tagagagaag aaaagcaccc cggctcccag gggcgcagca | 840 |
| actaatggga gtgcgtctgg gaaagttggc aagcccccat gtggggccct gaagaggtcc | 900 |
| attgcagaga gcgaggagtc tgaaacctac aagtctatct tcaccagcca cagctctgcc | 960 |
| aagcgctcca aggaggagtc tgcgcactgg gtcacccaca catcctactg cttctgaagc | 1020 |
| gggaccgggc cttcaccctg ggtttcccgt ggccttctgt gccacacttg cttggtgtgg | 1080 |
| cactgtgcta taaagctgtc ctctgcagtc ctc | 1113 |

<210> SEQ ID NO 13
<211> LENGTH: 976
<212> TYPE: DNA
<213> ORGANISM: Mus musculus

<400> SEQUENCE: 13

| | |
|---|---|
| gatgcgccgg aagtgcactg cggcgaacgc caggaagtcg agagcttgc agttgcagct | 60 |
| agttcttacc tgcagaacgc aagcggccgg agggtgtggg tacttttagc cagcggccgc | 120 |
| tgtcatgacg acccagggggg gcctagtggc caaccgaggc cggcggttca atgggccat | 180 |
| tgagctgagt gggccgggag gaggcagcag gggccgaagt gaccggggca gtggacaggg | 240 |
| agactccctc tatccagtcg gttacttgga caagcaagtg cctgatacca gcgtgcaaga | 300 |
| gaccgaccgg atcctggtgg agaagcgctg ctgggacatc gccttgggtc ccctcaagca | 360 |
| gattcccatg aacctcttca tcatgtacat ggcaggcaac accatttcca tcttccctac | 420 |
| tatgatggtg tgtatgatgg cctggcgacc cattcaagca cttatggcca tttcagccac | 480 |
| tttcaagatg ctggagagtt caagtcagaa gtttcttcaa ggcttggtct atctcattgg | 540 |
| gaacctgatg ggtttggcat tggcagttta caagtgccag tccatgggac tgttgcctac | 600 |
| acatgcatca gactggctag cctttattga gcccccctgag agaatggagt tcagtggagg | 660 |
| aggcttactt ctgtgacccc cagaaagcac catgcatatg gacctcatct gcattttaag | 720 |
| ctgttgactc ctaaatatcc tcccttaaaa cagtcatgca tgtggagaag agcctcctgt | 780 |
| ggtgaggcca gtgtgcagca tgttacagca gaaaagaaac tacagcacaa cttatgactg | 840 |
| aaaataatgt agaaaacttt atttatgttc ccagcacaga gcaaacaaa caaaccaga | 900 |
| ctctatgtaa acaaaagaat agcagctgct cagtagcagc ttctcctttc aataaattaa | 960 |
| acggttgaga acaatg | 976 |

<210> SEQ ID NO 14
<211> LENGTH: 179

```
<212> TYPE: DNA
<213> ORGANISM: Mus musculus

<400> SEQUENCE: 14
tttttttttt tttttttgc ttggcatatt tcttttcttt taaatacaac ttgcactgtt    60
tttactcata aatgagaagt tttatgttgt ttaacaatga cacctaaggc caagcgtcac   120
atacaaatca ggagtgaagc tctcatctgt gtagatgatg gtgtcctgcg ccatgtcct    179

<210> SEQ ID NO 15
<211> LENGTH: 2929
<212> TYPE: DNA
<213> ORGANISM: Mus musculus
<220> FEATURE:
<221> NAME/KEY: misc_feature
<222> LOCATION: (624)..(624)
<223> OTHER INFORMATION: Wherein N=A,T,C or G

<400> SEQUENCE: 15
ggcagctccc ggcgtgccct gccatctctg ctgcccgccg ccgacccctc cttcttctcg    60
tcccagtgcc accgagccgg agtccgagcc accgccgccg cagccacttc agccgcgggc   120
actatggcat ctggagttac agtgaatgat gaagtcatca aagttttaa tgatatgaaa    180 gtaagaaaat cttctacaca ggaggagatc aaaaaaagaa agaaagcagt tctcttctgt   240
tttgagcgat gacgaaagac aaataatagt agaggaagcc aagcagatct tggtgggtga   300
cattggtgac actgtagagg accctacac atcttttgtg aagttgttgc ctctgaatga   360
ttgccgatat gctttgtacg atgccacgta cgaaacaaaa gagtctaaga aagaagacct   420
agtatttata ttctgggctc ctgaaagtgc accgttaaaa agcaggatga tttatgctag   480
ctctaaagat gccattaaaa agaaatttac aggtattaaa catgagtggc aagtaaatgg   540
cttggacgat attaaggacc gctcgacgct gggatagaaa ctgggggca gtgttgtagt   600 ttcccttgaa ggaaagccac tatnaaataa tagccaagtg ccatttgatc ttaaggggct   660
tacacgtatc tctccagctc agtccactgg aattgtatta ggttttgttt ttttttgtta   720
attccctttt cactggtccc gttcgtgaat gagtgaatat aagaagcctg tcagtattgc   780
catgagactg tttcatatgg ttactttct gtattcccaa ggaatgcctt cctgtcttat    840
tttagccaaa acaaactggt tccatgcctt ccttgcagtg aacgttacaa tggatgtggt   900
tgtcaatgtg aatagcttag agtactacaa agggtaagct aactgaatgc cttgaaaata   960
ttatccactg gtcggtcata tgggagactt gtttcagtat tatttatagt tgcacttgat  1020
taccgtcctc tgaggcactg gagccttcat acacctcacc tgccttggca agcctatttt  1080
tgtgacctgg cagcacagat taacactat tcgttaaaag cactttttt ttaatgcgtt   1140 taatccctta taaagaatgc caattaagtt ttattacctg tcatcaattt atcctagtat  1200
ctcagtgttc attcttcttg ccttcatatt ttttcaaag aaacagctgt gctaatgtct   1260
ttggtttccc gatgagtgta cactactgta taatttatgt ttaccatatg agtcttgaaa  1320
cactacagat attttgaata tcagtcatgg tggcaatttc tgtataaaag agccttaaat  1380
ggaacattgt tttgagatca aactccctac cctcacaaaa gtggcacgt tgcaataaaa   1440 attgtggcag attacagaat gttgccttgt tttccttgga aattttgcaa attgttatgt  1500
gaaattttag ggtaacggtg attaagctct gcactggtat ttggaatttt ttttccttta  1560
atctttggtt taaaacatc ttaaaatcac ttatatacaa tcattaaaag agtggtaatt   1620
ttataaatgc ttatttatgt tataaaatgg agatcagaaa aaaattcttt ttgcactttg  1680
gcctatccag tatcttatct atcctctaga taagctagga tattaatcca gagttacatt  1740
```

```
actgagaatt gagtagtata agtaggatgt ttttattact tggtcataat gaaaataatt    1800
tgtaaaatgt cattcgaagg ttaatgatga ttgtgatgtt taggaatgtt tgtctcagcc    1860
acagttcctt catagctttt ccaaaatgaa ttgggaaaaa aaatcgtat  agcagtctta    1920 aagcttagta atggaacttg gctgtggccc agagctttct ccttatagag aatttgatct    1980
gctccgtgtg cgctctctgc tattagccgg agctatttat ggcaaacaca tgcttttgta    2040
tcttgtcata gtcatccaca gatggcaaaa ctggacttga ttctactggc atgtaagaca    2100
ggcgtgctag tgagcagtcg tgtgtggctc tggactctga ccccagagct ctgaagaatg    2160
ctcttatcag aagataggaa atgaaaatat ccttttttaa aatatgtgga agtaatttgg    2220
gtataattag ttttttttcta cctttttggaa agttgttttt ttgttgtttt ttttttttc    2280 ccagatgaga acattaacat agtggttaaa tgtctaggct tccatttaaa actacacaaa    2340
tgacttggga tcttttttagc actaaggaat ttgattcag  ccttccagct gttgctgtga    2400
gttgttccag acctttctgt ggcttttttgg taaggctgct tagaagcatg agaagcatga    2460
gaatggtaat gtgtgctaaa cctatgttta accaatcttt gcaccaaagg acttttttcac    2520 caatttattt tgttattctt ccaaatatta agtgatttct aaaaggtaaa gggtgacctt    2580
ttgtttttat atctaatttc tcaatttctt tatatgcatt tttagaataa tttgagagat    2640
taaatgctgc ttgaaactat tatactttga gttttagatt ggccaaatac attaatgtag    2700
ttaaattcat ctttaaagta cacatatgtg cctagagcca aaaaataata atgatttaat    2760
ttatgacctt atgttgagac taatttcaca tcttattttg cagtcattta cagtgaaaca    2820
atgttccagc tagctttaaa agctatacgg tgctaattag taaaatattg agggcaatat    2880
tttactgcta gcttgcaaaa ttataagtgt tttaaaaata aaatacatg                2929

<210> SEQ ID NO 16
<211> LENGTH: 1330
<212> TYPE: DNA
<213> ORGANISM: Mus musculus

<400> SEQUENCE: 16
gacagtctgt cagctgcggc tggtttctgc acatttccat gcagcagaca gcacaggcac      60
agaaccttct ctgctgcatt agagaagtcc acagatagcc ccaagttaca taggtggccc     120
agcaaactca gtccattagt gctgtgaaaa gaagttcctt actccttgga ttcaccggtc     180
agagcaaaaa acgcagttac ctctgaagta aagccgaaca aacttctaca ctgatctcag     240
agagcaaggg caaggacgca cgttcacgga ctcgcttttt tcaacagaca acaaagacgc     300
tgtggtagaa tttcatttca aaatgaaggc ttttgtttgg accctaagtg tactactctt     360
cctactgggc agtggtcatt gcaaaggagg acaactcaat aaaaaaaata acccaaagga     420
gatatccccg tgctactgat gggaaagagg aagcaaagaa atgttcatat acattcttgg     480
tacctgaaca aaaaataaca gggccaatct gtgtcaacac caaaggtcag gatgcaggca     540
ctattaagga catgatcacc aggatggacc tggagaacct caaggatgtg ctgtctaggc     600
agaagcggga gatagatgtc ctgcagctgg tggtagatgt ggacgggaac attgtaaacg     660
aggtgaagct gctgagaaag gaaagccgga acatgaactc cagagtcacg cagctctaca     720
tgcagctact acatgagatc atccgtaaaa gagacaattc actcgaactt cccagctgg      780 aaaacaaaat cctcaatgtc accacagaaa tgctgaagat ggcaacaagg tacagggagc     840
tagaggtgaa gtatgcgtcc ttgacggatc ttgtcaataa ccagtctgtg acgatcactg     900
tattggaaga gcagtgcctg aggatgtttt cccgacaaga ccccacgcg tctcccctc     960
```

```
ttgtccaggt ggtaccgcga cacagtccta acagccacca gtacacccct ggtctgctgg      1020
gaggcaatga gatacagagg gacccaggtt accccagaga cgtaatgcca ccacctgatc      1080
tgccaacagc tcccacgaaa agcccttca agattccagc agtgactttc atcaatgaag       1140
gtgagttact gcttcctggc caatggaaga acgaagctgg tatgctgatg ctgtatgatt      1200
cacgcaacaa tactcttatc ttagtaagtc ctacttctta tgtgctgatg ccattataca      1260
tgtccaatca aaattttcac ttttaaagt gatgtttgga tttgatataa aacatctctt       1320
ttctccgtgc                                                             1330

<210> SEQ ID NO 17
<211> LENGTH: 289
<212> TYPE: DNA
<213> ORGANISM: Mus musculus

<400> SEQUENCE: 17
ccaaagcacc cccatctttc gagttcgccc ccattccagt caacagagcc acttccaaga       60
ccacccctcc agcctaccca gagtaaccca aagaacaaa aaattcccca tctgtactct       120
ttcgggctca taccttcttc tttggaacat cacgtgggtg agctccagca tatggaaatt      180
ctctggatat tttctgggaa accctcccc gtgttcctct tcccgtggaa atgctatgcg       240
ggtttcgcaa tcgggtattc tcattaaatg gaaattctgt gtgcgctcc                  289

<210> SEQ ID NO 18
<211> LENGTH: 980
<212> TYPE: DNA
<213> ORGANISM: Mus musculus

<400> SEQUENCE: 18
ggaggtgtgc ggctggctgt tggagtgaag ccttggaaga catggctccc aacgtgttgg       60
cttccgaacc ggagattccg aaggcatccg ggccgtgttg ctggggccgc ccggggctgg      120
caaggggacg cggcacccaa actggctgaa aacttttgtg tctgtcattt ggccaccggg      180
gacatgctga gagccatggt agcttctggc tcagagctag gaaaaaagct gaaggcgaca      240
atggatgcag ggaaactggt gagtgacgaa atggttgtgg agctaattga aagaatttg       300 gagactcctt cgtgcaaaaa tggctttctt ctagatggct tccctcggac tgtgaggcag      360
gctgaaatgc ttgatgacct catggagaag aggaaagaga agctcgattc agtcattgag      420
ttcagcatcc aagactcgct gctgatccgg aggatcactg ggaggctgat tcaccccaag      480
agtggccggt cctaccatga ggaattcaac cctccaaagg agcccatgaa agatgatatc      540
actggggagc ccctgatccg caggtcagat gacaacgaga agccttgaa gacccgcctg       600 gaggcctacc acactcagac cactccgctc gtggagtact acaggaaacg cggcattcac      660
tgcgccatcg atgcgtccca gacccctgac atcgtgtttg cgagcatcct ggcagccttc      720
tccaaagcca catcctagta acagaaggcc aggcgagacc gcacccctgc tcatctcccc      780
gccgtgggat ccctgctctt aggtgctggg cagaggaag agggtggtca tgggaaggaa       840
ggatggatgg atggtgaggg aggtggggag gggctcctcg agaagaagatt ggaacagtgg      900 cagtgttata attagtaagg tttttttttt ttacacatag atgagaattt taaagtata       960 agcaagggaa aagattaatc                                                  980

<210> SEQ ID NO 19
<211> LENGTH: 617
<212> TYPE: DNA
<213> ORGANISM: Mus musculus
```

```
<400> SEQUENCE: 19
gagtgtctcc acggactaca gtggatggca tcgaagattc cctttgccac agatctgaca      60
gactatgaga aaatgccagt aagtccattt gggaaagtga agcccagcgg agaggggaca     120
gcacaaaggc ctatagaaat aagtgcctca ccattagcag agctggagga caagataaag     180
cggcacacac agcagatccg cactcgaagt ttcctgggta caaacccaat gcaagacatt     240
aagacagcca accaggacct ggaaaccact aagaaacttc aggaggagtt aaggaaactg     300
aaagtggaga tgaccttgaa caaagaccat ccatttccat cttttcactgg aaacctttca    360 cttcacccac cagcatcaca gcctcaaaat atattttta acacgaaatc ctaggaaggc      420
agcgctgtca gcaggagtga caagtacctt ccacacgagg agctgctgtc ccccatgtgt     480
gtggggactg gcctggatga caactcgcgg gtaactcgcg ggtcttccct gccacacagg     540
ctatggcttt aatagacct gattccttcc tgaggctata aaggtttag ctgcattaaa       600 cgagatgctt cagcagc                                                    617

<210> SEQ ID NO 20
<211> LENGTH: 7036
<212> TYPE: DNA
<213> ORGANISM: Mus musculus

<400> SEQUENCE: 20
gcctcgcgag ctctggcgtg gcgctcgccg gctggccctc acggggaaga ggtggcgttc      60
cgttggtgac gttaggctcc ggcggcgccg gcagggcgtt ctccggagct gtgcggccag     120
ctcgccgccg tcccgctgct gcgctcgcga tgggcgccca ggaccggccg cagtgtcact     180
tcgacatcga gatcaaccgg gaaccggttg gtcgaattat gtttcagctc ttctcagaca     240
tatgtccaaa aacatgcaaa aacttcctat gcctgtgctc aggggagaaa ggccttggga     300
aaacaactgg gaagaagtta tgttataaag gttctacatt ccaccgtgtg gttaaaaact     360
ttatgattca gggtggggac ttcagtgaag gtaatggaaa aggtggagaa tcaatttatg     420
gtggatactt taaagatgaa aactttattc tcaaacatga cagagcgttc cttttgtcaa     480
tggcaaatcg agggaaacat accaatggtt cccagttttt cataactaca aagcctgctc     540
cacacctgga tggggttcat gttgttttg gactggtaat atctggtttt gaagtaattg      600
aacagattga aaatctgaaa acagatgctg caagcagacc ttatgcagat gtccgagtta    660
ttgactgtgg ggtgctggcc acaaagttga caaaagatgt ttttgagaaa aaaggaaga    720 aaccaacctg ttcagaaggc tcggactctt cttcccgttc ctcttcctct tcagagtcct    780
cctcagagag tgaagttgag cgagagacaa tcagaaggag aagacataag aggaggccaa    840
aagtcagaca tgctaaaaag agacggaaag aaatgagcag ttcagaagaa ccgaggagga    900
agcgcacagt aagccctgaa ggttattctg agaggagtga tgtgaatgaa aaagatcag    960 ttgactcaaa cactaaaaga gaaaagcctg ttgtccgccc agaagagatt cctccagttc   1020
ccgagaaccg attttactt agaagagata tgcctgctat cactgtggag cctgaacaga    1080
acattccaga tgttgcacct gttgtaagtg atcagaaacc ctctgtatca aagtctggac    1140
ggaaaatcaa aggaagaggc acgattcgct atcacacacc tccaaggtca agatcccact    1200
ctgagtccaa agatgatgac agcagtgaaa cccctcctca ctggaaggag gagatgcaga    1260
gactgagagc ctacaggccc cgagcggaga gaagtggag caaaggagac aagctgagtg    1320 accctgttc aagccgatgg gatgaaagaa gcctgtccca gagatccaga tcatggtcct    1380
ataatggata ctattcagat cttagtacag cgagacactc tgatggtcac cataagaaac    1440
```

```
acagaaagga aaagaagttt aagcataaaa aaaaagctaa aaagcagaaa cattgcagaa   1500
gacacagaca gacaaaaaag aggagaatag ttatgcctga tttggaaccc tcaagatctc   1560
ccacccaccg aatgaagtcc tcttgtgtta gagaaaggag atctcgtgcc tcctcctcct   1620
cctctcatca ctcatccaag cgcgactggt ctaaatcaga ccaggatgac gggagtgctt   1680
caacccattc cagcagagac tcctacagat ccaagtctca ttcacgatca gattctagag   1740
ggagctctag atcaagggct gtgtcaaagt cctcatctcg ttctctcaac agatcaaaat   1800
ctagatctag ttccaggtca ggaccccgaa gaacatcaat atcccccaaa aaacctgctc   1860
agctgagtga aaataagcca gttaagacag aacctttaag gccgtcagtg ccacagaatg   1920
gaaatgtgct agtgcaacca gtggcagcag aaaacattcc tgtaatacca ttgagtgaca   1980
gccctccccc ttctaggtgg aagcctgggc agaagccctg gaagccctct tacgagcgaa   2040
ttcaggagat gaaagctaaa caacccact tgctgcctgt ccaaagcaca tacagcttaa   2100
caaatattaa agcaaccgtg agttcatcat cttatcacaa aagagaaaaa ccttcagaaa   2160
gtgatgggag tgcttattca aagtacagtg atagaagttc tggaagctca ggaaggtcgg   2220
ggagcaagtc ttctaggagc aggtcatcct ccaggtccta cacaaggtca aggtcaagaa   2280
gtctccctac ttcacgctca ctctctaggt ctccatcatc taggtctcac tcaccaaata   2340
agtacagtga tggttcccag cacagtaggt catcttcata tacttctgtt agcagtgatg   2400
atggaagacg agccatgttt agatccaaca ggaaaaaaag tgtcacttca cataaaagac   2460
atcgcagcaa ctctgaaaag acacttcaca gtaaatatgt cagaggcaga gagaaatcct   2520
cacgtcacag aaagtatagt gaaagtagat catctttaga ttacacttca gacagtgacc   2580
agtcacatgt tcaagtatac tcagccccag agaaggagaa gcaggaaaaa gtggaagcat   2640
tgaatgataa gcagggaaaa ggcagagaag aaggaaaacc caagcctgaa tgggaatgtc   2700
ctcgttctaa aaaagagaac tccgaagatc actctagaga tgacagtgtg tccaaaggga   2760
agaattgtgc ggggagtaaa tgggattcgg aatcaaactc agaacaagat gtgactaaga   2820
gcaggaaaag tgatccccgg agaggttcag aaaaggagga gggtgaagcc tcttcagact   2880
ccgagtcaga agttggtcag agtcacatca aagccaaacc cccagcaaag cctccaacaa   2940
gcactttcct gcccggcagc gacggtgcct ggaagtctag gagaccacag tcttcagcct   3000
ctgagtcaga gagctcctgc tccaacttgg ggaacattag aggagagccc cagaagcaaa   3060
aacactcaaa ggatgatctt aaggggatc acacaaaaag ggcaagagag aagtcaaaag   3120
ctaaaaaaga caaaaaacac aaggctccaa aacggaagca agctttccac tggcaacctc   3180
cactcgagtt tggtgacgat gaggaggagg agatgaatgg gaagcaagtt acacaggacc   3240
caaaagagaa aaggcatgtc tctgagaagt gtgaagctgt gaaagacggc attccaaacg   3300
tcgagaaaac ctgtgatgaa gcagttctc caagtaaacc caagaagggt actttagagc   3360
aggacccact tgcagagggt ggacatgatc ccagctcttg tcctgcacct ctgaaagtgg   3420
aggacaacac ggccagctct ccacctagcg cccagcacct tgaagagcat ggcccaggtg   3480
gaggggagga cgtgcttcag acagatgaca acatggagat ttgcacgcct gataggactt   3540
cccctgcaaa gggagaggtg gtgtccccctt tagcaaacca caggctagac agcccagagg   3600
tgaacattat tccagagcag gatgagtgta tggcacatcc tagagcagga ggagaacaag   3660
agagtagcat gtctgaaagc aagaccttgg gtgaaagtgg ggttaaacag gacagctcta   3720
ccagtgtgac cagtcctgta gaaacttctg gaaagaagga gggggctgag aagagccaaa   3780
tgaacctcac agataagtgg aagccattgc aaggtgtagg gaatctgtca gtgtctactg   3840
```

```
caaccacatc cagtgctctg gatgtgaagg cattatctac tgtgcctgaa gtgaaaccac   3900
aaggcttgag gatagaaatc aaaagcaaaa ataaggttcg gcctgggtct ctctttgatg   3960
aagtaagaaa gacggcacgc ctaaatcgaa ggccacggaa tcaagagagt tccagtgatg   4020
atcagacacc tagtcgggat ggtgatagcc agtccaggag tccacacaga tctcgaagca   4080
aatccgaaac caaatctcga cacagaacaa ggtctgtctc atacagtcac tcacgaagtc   4140
gatctagaag ctctacgtca tcttaccgat caagaagcta ctctagaagc cggagcaggg   4200
actggtatag cagaggccga acccgcagcc ggagcagttc ctatggaagt ttccatagtc   4260
acaggacgtc cagcaggagc cggtccagga gcagctctta tgacctccat agccgctcca   4320
gatcctacac ctacgatagc tactacagcc ggagtcgtag ccgcagccgc agccagagga   4380
gtgacagtta ccatcggggt agaagttaca acaggcggtc caggagtggt agatcctatg   4440
gctcagacag tgaaagtgac agaagttact ctcatcaccg agtcccagc gagagcagca    4500 gatacagctg agatgtctct gtacagattg tgtcttaagt gtaaatacct ggtaacttaa   4560
agcttaagaa actggatggc agtctgttgt gttttagtat tagacctcaa tcctatagtg   4620
gatatttctt gtcacttatt tacatgtgcg caaaagaatt taaagtgcag atgtccctag   4680
aaatatttct atgacccatt ttacagtagg caactatgga attttcattt tcttgaatca   4740
agaaatggta aatttgatgt aagtataatt tgcagtgtca ctgtagatag ggttttctgt   4800
agatcacatt gtctgtagaa ttcaggtttc tttttgtttc aggttttagc atccatgctg   4860
ccaaacacaa ttatggagag ctgtcacaag acacgtgttc tccatgtccc catgtcccca   4920
tgctggttgt cgtcttggtg tgtgctgtca gatgaggctg tccacatcca tattgaccat   4980
ggccaggtgt gcagggtggt agctcattcc tctgtgtccc agctgtgagc acccacactt   5040
cacagggaat gccagcccag ccaccccagc tcctgctttg gtgcttggtg cctttggttc   5100
ctcgtatacc ctatgtcata ttgtcacata ctgcatttcc tgatgccaga aaatgaattg   5160
tgattttttt ttttttaaatt cactggcacc aaaaataatt tcttctgagc tgggttcact   5220
gtgagtgtag gggcttcttc caaacacaga tatgtggtgg aggtccctg gaacagaacc    5280 tgtatggctg gtcatcttgt tctgcacatg tgtgctaaag tgccgagctg aagaatgtcc   5340
ttcagaagca gctccacaga cactccagcc aagcttcact ctcactgtgg caatagtagc   5400
agccctgccc caaccatcct attccctgtt tgtgtcgaga caccccccac ccccaccccc   5460
acgctgcccc ctgactccat gaagccctgc ctgatggagg aaacccagga caaaagttgg   5520
gggcagcagg gtcacaggct ctgctgcaca gaaagggggtt cttacggctt tgtgtggctc   5580
ctccaggaag aatctaacct gtaaaaacta gtgtgggttt gtttctttgt tttgtttttac  5640 tctttagttt gcattctttc cccaagtgta cttaatcacc ttagtgccgg ttaaatccag   5700
ttcacagact tcctgtcagg tatatggtgt agaagtctgt actctcctat cccacccagg   5760
ccttgctagt gcatttggga agagtaaagg ccttgggctg gaggaaatta ctaaagccct   5820
ggccagatgg aggggaagta ctggatatat gaaagtagtc ttccagggcc atgtggctca   5880
gtgatatata gcatgtgctt agcatgtaag tagctctggg atcagaggtc agcacccac    5940 aaataaataa tggtgttact ctgtgatgta tgtaagcagc attttggtgg ccagccagct   6000
tattgttcca ccatgtctgt aaattagtta attagaagga taacatcgga actcagtgct   6060
tggcgggtta gacatgtggt ttatagtgag tgggtccttc tacccccccc cccctttaa    6120 agttgcctac aaagaagggt gtttgaatct agtattcagt aggaagaatg cattcagagc   6180
ccaaataaac tggcaaatgt aattagtaag aaaaggtcac tattgggcca tatattctta   6240
```

```
tttggttgct gtgtaacaag ttatcccaaa tttctcagcc taagagtgcc tatgtgtcat    6300
tgacaaacag gcaatggtag ggttgactca tctgctcagg gtctcaaggt aaggtctgga    6360
agagctcatt tctcagaaga ctctgggaag acgtgacttg tagctgggcc cctctagagc    6420
cctcggtgga tgcccacatc gcctgctgta ggccttgcca gcttcaacca gcagggaccc    6480
tttgagtctt gtcttttttt caaaacctct gccctcctcc tgctttaagg gtccatgtaa    6540
gtagatcaga ctccagagat aaatctctac tcgaagtccc gtggccagag gaattacaga    6600
cattgtcggg ttctggggat tagcatagca agaggaaggg catccaccta ccacctactg    6660
ctgcatggac agggcttaac ctgtaccagc aggcactcat gttacgtaat gtcaaccttg    6720
ctgtttatac tcgactgaat acagaaatgg cttttcttct tatccacgat cattctgtat    6780
tttgaagtta ttttttttaat aaaattgaat tatgttgtgt aatgtgctta atagaaaatg    6840 cttttctttat tggatgattt tgtaacatcc tgtttactgc aagtggcata gttgatattg    6900
ttcaaaaatg tagaaaatac ttttgtacat actagcaatg tctaatttgt atatacttct    6960
atgaaatttc tctacaactt gaaaaggatc ttgtagaaat gaaaatacat gctgagtttg    7020
agcctaaaaa aaaaaa                                                    7036

<210> SEQ ID NO 21
<211> LENGTH: 2190
<212> TYPE: DNA
<213> ORGANISM: Mus musculus

<400> SEQUENCE: 21
gaagcaggga cgagtggagg tgccgcaggc tgagtcgcgg ccgggatgtc cgggcagccg      60
ccgccaccgc cgccgcaaca gcagccgccg ccgccgccgc ccccgcctc ggcggccgcc     120 cccgccaccg cgccgcccgg cctggcggtg ggccccggcc cggccgcagg cgtcccggtc     180
ccgggcctgg cggcgggcag cagcgccgct gccccttttcc cgcacggcga ctcggccctc     240
aacgagcagg agaaggagct gcagaggcgg ctgaagcgcc tctacccggc tgtggatgag     300
caggagacgc cgctgcccg gtcctggagc ccgaaggaca agttcagcta catcggcctc     360
tcgcagaaca acctgcgggt gcactacaaa ggtcatggta aacccccaa agatgcagca     420 tctgttcgag ccacgcatcc aataccagcg gcctgtggga tttattattt tgaagtaaaa     480
attgtcagta agggaagaga tggctacatg ggaattggtc tttctgctca aggtgtgaac     540
atgaatagac taccaggttg ggataaacat tcatatggtt accatgggga tgatggacat     600
tcattttgtt cttctggaac tggacaaccg tatggaccaa cttttacaac tggtgatgtc     660
attggctgtt gtgttaatct tatcaacaat acctgctttt acacgaagaa tggacatagt     720
ttaggtattg cttttcaccga cttaccgcca aatttgtatc ctactgtggg gcttcagaca     780
ccaggagaag tggttgatgc caactttggg caacatcctt ttgtgtttga tatagaagac     840
tacatgcgag aatggagaac caaaatacag gcccagatag accgctttcc tatcggggat     900
cgagaaggag aatggcagac catgatccaa aaaatggttt catcttattt agtcccaccat     960 gggtactgtg ccacagcaga ggcctttgcc agatctacag accagactgt tctagaagaa    1020
ttagcttcca ttaagaatag acaaagaatt cagaagttgg tgttagcagg acgaatggga    1080
gaagccattg aaacaacaca acagtatatac ccaagtttac ttgaaagaaa tcccaatctc    1140
cttttcacat taaagtacg tcagtttata gaaatggtga atggtacaga cagtgaagtg    1200
cggtgtttgg gaggccgaag tccaaaatct caagacagtt atcccgtcag tcctcgaccc    1260
tttagtagtc caagcatgag ccccagtcat ggaatgagta tccacagctt agcaccaggc    1320
```

| | |
|---|---|
| aaaagcagca ctgcacattt ttctggtttt gaaagttgta gcaatggtgt aatatcaaat | 1380 |
| aaagcacacc aatcatattg ccatagtaaa caccagctat ccagcttgac tgtaccggag | 1440 |
| ctaaacagtc tcaatgtatc aaggtcacag caagttaata actttaccag taatgatgta | 1500 |
| gacatggaaa cagatcacta ctccaatgga gttggagaaa cttcatccaa tggtttccta | 1560 |
| aatggtagct ctaaacatga ccacgaaatg gaagattgtg acaccgaaat ggaagttgac | 1620 |
| tgcagtcagt taagacgcca gctgtgtgga ggaagtcagg ctgccataga gaggatgatt | 1680 |
| cactttggcc gagagctaca agccatgagt gagcagctga ggagagaatg tgcaagaac | 1740 |
| acagcaaata gaaaatgct gaaggacgca ttcagcttac tagcatattc ggatccttgg | 1800 |
| aatagtccag ttggaaatca gcttgaccca attcagagag aacctgtgtg ctcagctctt | 1860 |
| aacagtgcaa tattagaaac ccacaatctg ccaaagcaac ctccacttgc cctagccatg | 1920 |
| ggacaggcca cacagtgtct aggcctgatg gctcggtcag gagttgggtc ctgtgcattt | 1980 |
| gccacagtgg aagactacct acattagcta tgcacttcaa gagctcacac tcacattgtg | 2040 |
| gcaaacagtc aacatggaag tagaccggct ctgctgattt gaaatttaga ttttttttta | 2100 |
| attatgtact ggggacaggt ttttgtcgct ttacattgct tcctagtttt acagcatgat | 2160 |
| gcaaatgaat tttctaactt agtgtttagg | 2190 |

<210> SEQ ID NO 22
<211> LENGTH: 857
<212> TYPE: DNA
<213> ORGANISM: Mus musculus

<400> SEQUENCE: 22

| | |
|---|---|
| gcagtcacgt gaggcgctaa gatggcggcg tcccagcgac caagttggtc cgagtcgaag | 60 |
| gttgctggtg ttgtgcagga gggaaatagg gaagcacccc aggacatcaa gatggcactt | 120 |
| tataaacatg gtcagctgat tccttcccta ggagatgcaa agttcagaag cccgataatc | 180 |
| tctgaaatta tagaaaagaa gtttgaacat tatagaaacg acaagacttt aaatatacat | 240 |
| ggaactttgg tctttggaac aagtagtagt ttgtctggca taatggcaaa cttagttttc | 300 |
| cgaaacagtt tcaaggttaa atatgaagct ttgaagacct atgcatccct gactacactt | 360 |
| ccagttttgg ctaccatcgt ttcttacaag ctctttgtaa cagatgcttt gcaatcaggt | 420 |
| gacataagca aggaaagctg tgttctgagg agcgcactaa ttggcatggc atgcggcgtt | 480 |
| tcctaccccca gtgctttggc tttctataaa aatggacgtt tggcagttaa gtatcagact | 540 |
| gttccactgc caccaaaggg aagagttatg ctccattggt tgctcctttg tcaaactggg | 600 |
| atgaaagcaa tggctattcc tctgttcttt cagatagtaa tgggagcttt tactggctta | 660 |
| catcattaca atatatgtga aaaccacgt gcaaggcttg tgcctgatga ttaaccaaag | 720 |
| actccatgga ctccatggaa gccggttcaa tggcatgaac ttctttatag acggactttg | 780 |
| ccactggtct aagagggaaa aggaactttt gcctggcata tatcagacac tcagtaatta | 840 |
| tgaatgttat aaatgtt | 857 |

<210> SEQ ID NO 23
<211> LENGTH: 1146
<212> TYPE: DNA
<213> ORGANISM: Mus musculus

<400> SEQUENCE: 23

| | |
|---|---|
| tggacccagc tgaggagcga agagctgctg gcagcgccga ttcccagcac gccgcttttt | 60 |
| agaacttcag ttgtcaaaat ggcagaatc tttcttgacc atatcggtgg tacccgtctg | 120 |

```
tttcttgtg caaactgtga tacaatcctg accaatcgct cagaactcat ctctactcgg      180
ttcacaggcg ccactggtag agcatttctt tttaacaagg tagttaactt gcagtacagt      240
gaagttcaag atcgggtcat gctcactggc cgccacatgg ttcgagatgt gagctgcaaa      300
aactgcaata gcaaactggg atggatctat gagtttgcta ctgaagacag ccagcgttat      360
aaggaaggcc gtgtgatcct ggaacgtgca ctagttcgag agagtgaagg ctttgaagag      420
catgtaccat ctgataactc ttgaagaaaa aagataaatc catcttttcc caggtctcct      480
tcactgaaaa caaatctcc ttacatacac tgtcaccta gcatcagaat cggattcatg      540
aactgcggaa caagaggttt tgagaatcta agatggaacc tttttttctt tcttttttt      600 ttttaaattt ggtatttcc aacccaacag cagtttgtag agagaatttt atgcataggc      660
tggtaatttt ttccctgtgt ttacatcttg agacagaaga gtttgcagct acatggttgg      720
ctatgtgagg gaaaaaaatt ggggtcctta gagtgaaaag gagtgttttg tgtatatttt      780
gagtggagaa tatgtcaaga gcatggtttt taaatttatt tgggctttat ttaaaattt      840 cttttaacc cagttattc acttaattg ctagcttcaa gaagagatcc gaatctgtgc      900
ccagcgctgg aggctcagtg ttagcatggc ttgtgctggc cagtgtgcca tattcttgtt      960
ggagaggaac tgtagcacca gaacccattc ttccttgtca gtcttgaccc acagatgtca     1020 ccaccoctag ttccttgtca ccatggactt ggtgttgatt ggaaactttc tgaaatgggg     1080
cagaactgct tggttgtctt ttcccatgta acttaagcat agtaatataa ataaagtggt     1140
agttgg                                                               1146

<210> SEQ ID NO 24
<211> LENGTH: 966
<212> TYPE: DNA
<213> ORGANISM: Mus musculus

<400> SEQUENCE: 24
aaaatgagta ctacatggct atttacgaat gggaagaata aggcttaact tttaatgtaa       60
ttaaatctgt gcactacatt cctgagcaat gagcagaatg tattttaagt atgtattaaa      120
tatttgaaat tataaatcta ggccgctgta gcccgcatcc agaggcaggg gcagctaggt      180
ttctttgagt tagagaccag cctggtctag gtagtaagtt ccaggactac cagagctgtg      240
cagcgagact gtctcaaaaa ccaaaccaaa ccaaaaccca acccaaacca aacaaagcca      300
aacaacaaca acaaaaacaa aaaaacccac caaaaaaacc aaggaaacaa aacaaccaaa      360
aatcaaaaaa ctaggctact ttaaaatgtc attatttatt ttgttaaaat tcctgagata      420
aacactattc taacaaaaga gccattaaga ctaagaatct ctaagatagt ttttatgttc      480
tcaaattcag aagaactaaa cacattattg cagtattaat aaaataaaaa ctcaagataa      540
gaaggtcaaa tgtgtccaag ataattgtct cctccacaat gaggcaaatc cataaggaat      600
aatgggggga agttcaatgc attagctttt gacagtcaaa acaggaacct ttaaaatact      660
ctgttcatgg ttaaaaataa tttgtactct aagtccagtg atcattgcca gggagaacca      720
aagttgagaa atttctatta aaaacatgac tcagaggaaa acatacaggg tctggtcatg      780
aaggaaatga tctggccccc attggtcact cctacagtca catggtcagg gcatctttaa      840
aagtgagcta tctggacttc agaggctcat agcaccctcc tgtgctgcag cctttctcac      900
ctggaagaca gctcctcctc gaaggtttac aaaatgtgtg atgccttgt gggaacctgg      960 aagctt                                                                966
```

```
<210> SEQ ID NO 25
<211> LENGTH: 564
<212> TYPE: DNA
<213> ORGANISM: Mus musculus
<220> FEATURE:
<221> NAME/KEY: misc_feature
<222> LOCATION: (433)..(488)
<223> OTHER INFORMATION: Wherein N=A,T,C or G

<400> SEQUENCE: 25
tcaaaataca aacatagact ttattaaatg ctgctcaatc ctcagtaaag atctctcatt      60
ataaaacagt tttccataca actgcaaggc aagaggctgg aatggtactg gtaacaacag     120
tgtgaaaaat acctgaccag gtaaaaacag acaaagcttc tacatagtca gctctgagga    180
cacctgctgc agttccttta aataaagcca ggcagtgaca gctagcagtc tgcatcacac     240
tgtgggaggg acccaaagct ccaccctgca ggcaggcagg cctggggact ggcagggtga    300
ggactgggaa ggccctgcct ccagccttgg aggagaggaa tgaaggaggt gagcctcggg    360
tccacccgtg gcctgtgctg ctccgcacac gctccgggga gccgctgctg aagggggggat  420 ttgggaacat canaattttg gtttacttcc cccccccaac tttaatactt tgtgcttcag   480
aagcctgnaa atgtcagatg ttgtaaaacc cagagtatgg cagtgtcttt aatgaggctg   540
ggctcttgtc ccctgcccac acct                                              564

<210> SEQ ID NO 26
<211> LENGTH: 399
<212> TYPE: DNA
<213> ORGANISM: Mus musculus

<400> SEQUENCE: 26
atgtgtgatg cctttgtggg aacctggaag cttgtctcca gtgaaaactt cgatgattac      60
atgaaagaag tgggagtggg cttttgccaca aggaaagtgg caggcatggc caagcccacc    120
atgatcatca gcgtaaatgg ggatttggtc accatccggt cagagagtac ttttaaaaac    180
accgagattt ccttcaaact gggcgtggaa ttcgatgaaa tcaccgcaga cgacaggaag    240
gtgaagagca tcataaccct agatggcggg gccctggtgc aggtgcagaa gtgggatgga   300
aagtcgacca caataaagag aaaacgagat ggtgacaagc tggtggtgga atgtgttatg    360
aaaggcgtga cttccacaag agtttatgaa agggcatga                               399

<210> SEQ ID NO 27
<211> LENGTH: 2113
<212> TYPE: DNA
<213> ORGANISM: Mus musculus

<400> SEQUENCE: 27
tggcggtggc ctgagcagcg cgagtgtgat gaggctgccc tgcctcgcag ctccgctcgc      60
agccagctga cagcgcctgc cctcagcaca cccggagggg agccgcgggg ccgtgacctt    120
ggccgaggag ggcagattga tcatccttgt atctgagcta ccaagttctg ggtgaaatgg   180
ctcagggaaa taattatgga cagaccagca acggggtggc ggacgaatca cccaacatgc    240
tggtgtacag aaagatggaa gatgtcatag cacgtatgca agacgagaaa aacgaaattc    300
ccatccgtac cgtcaaaagc ttccttttcca agatccccag tgtcttctcc gggtcagaca    360
ttgttcaatg gttaataaag aacttaacta tagaagatcc agtggaggct ctccatttgg    420
gaacgctaat ggctgccat ggctacttct ttcccatctc agatcatgtc ctcacactca    480
aggatgacgg caccttctac cggtttcaga caccctattt ttggccgtca aattgttggg   540
agccagaaaa cacagactat gctgtttacc tctgcaagag aacaatgcaa aacaaggcaa   600
```

```
ggctagagct agcagattat gaagccgaga gcctggccag gctgcagaga gcatttgccc    660
ggaagtggga gttcattttt atgcaagcag aagcacaagc taaagtggac aagaagagag    720
acaaaattga aggaagatc ctcgatagtc aagagagagc attctgggat gtccacaggc    780
ctgtgcctgg atgtgtaaat actacagaag tggacattaa gaagtcatcc cggatgagaa    840
acccacacaa acacgaaag tctgtctatg gtttacaaaa tgacatccga agtcacagtc    900
ccacccacac acctacacca gaaccaagc ctcctacaga agatgagctg caccaacaga    960
taaaatactg gcaaatacag ttagatagac atcggttaaa aatgtcaaaa gttgctgata   1020
gtctactaag ctatacggaa cagtatgtag aatatgaccc atttcttgtg ccgcctgacc   1080
cttccaatcc atggctttca gatgatacga ctttctggga acttgaagca agcaaagaac   1140
caagtcaaca gagggtaaaa cgatggggtt ttggtatgga tgaggcattg aaagacccag   1200
ttgggagaga gcagttcctt aagtttctag aatcagaatt cagctcagag aacttaaggt   1260
tctggttggc agtggaggac ctgaagagaa ggcctatccg agaggtcccc tcgagagtgc   1320
aggaaatatg gcaagaattt ctggctcctg gggcccccag tgccattaac ttggattcta   1380
agagttatga caagaccaca cagaatgtga aggaaccagg acgatacaca tttgaagatg   1440
ctcaggagca tatttacaag ctgatgaaga gcgactccta ccccgctttt ataagatcta   1500
gtgcctacca ggaacttcta caggcaaaga gaaaggaaa aactctcaca tccaagagct   1560
taacaagcct tgttcagtct tactagaagg accgtctttg tcacatgagt gctgaacgga   1620
gccatcgccc atacccttgta gcccatcgct gttacctgga gccaaggacg ttagaccaag   1680
atgttgcatg aacaaaggac tggaattgtt cttttctgtg tgcacataaa gtcatcacac   1740
ttgccaaggg acgctgtcat ttcattgcct tcatcttcat gtgtcgtctg cttccctctc   1800
tcctcgtgct aagctggatc cgtgtccttt ctttttaac gagttcaagt gaacgaaaac   1860
ttatttcccc cccttcctct ccttttcttg aagcttctgc tagatgaaaa ttcactgaaa   1920
attcagtcag tcacaaactg gaagaattgt aaaagaaaaa aaagtatat atcactaagt   1980 acacacatgg cttcacactt attaactaat aaattggcac agaaggtgtc gtttcacccct   2040 tgtatccaca gtctgaagca agcacccatt ttcatctgtt ctccggacat tgtctgttcc   2100
tgtttcttgc aca                                                      2113
```

<210> SEQ ID NO 28
<211> LENGTH: 1657
<212> TYPE: DNA
<213> ORGANISM: Mus musculus

<400> SEQUENCE: 28

```
aaaacatgga gtcagctccg gcagccccg accccgccgc cagcgaaccg ggcagcagcg     60
gctcggaggc ggccgcgggc tccagggaga ccccgctgac ccaggacacg ggccgcaaga    120
gcgaggcacc gggcgcgggg cgcaggcaga gctatgcgag ctccagccga ggtatctcag    180
tcacgaagaa gacacacaca tctcaaattg aaattattcc atgcaagatc tgtggagaca    240
aatcgtcagg aatccattat ggtgtcatta cgtgtgaagg ctgcaaggc ttttcagga     300 gaagtcagca gagcaatgcc acctactcct gtcctcgtca aagaactgt ttgattgatc    360 ggaccagcag aaaccgctgc cagcattgtc ggctgcagaa atgcctggcc gtggggatgt    420
ctcgagatgc tgtcaagttt ggtcggatgt ccaagaagca gagagacagc ttgtacgccg    480
aggtgcagaa gcaccggatg cagcagcagc agcgagacca ccagcagcag cctggggagg    540
cggagccgct gacgcccacc tacaacatct cagccaatgg gctgacggaa ctgcatgatg    600
```

-continued

```
acctcagcac ctatatggat gggcacaccc ccgagggcag caaggccgac tcagccgtca      660
gcagcttcta cctggacatc cagccctccc cagaccagtc gggattggac atcaatggga      720
tcaaacccga acccatatgt gactacacac cagcatctgg cttcttcccc tactgttcct      780
tcaccaacgg agagacttcc ccaaccgtgt ccatggcaga actagaacac cttgcccaga      840
acatatccaa atcccacctg gaaacctgcc agtacttgcg ggaagagctc cagcagataa      900
cgtggcagac cttcctgcag gaggagattg aaaactacca gaacaagcag agagaggtga      960
tgtggcagct gtgtgccatc aagattacag aagctatcca gtatgtggtg gagtttgcca     1020
aacgcattga tggatttatg gagctgtgtc aaaatgatca aattgtgctt ctaaaagcag     1080
gctcgctaga ggtggtgttt attaggatgt gccgtgcctt tgactctcag aacaacaccg     1140
tgtactttga cgggaagtat gcgagccccg atgtcttcaa gtccctaggt tgtgaagact     1200
tcatcagctt tgtgtttgaa tttgggaaga gtttgtgttc tatgcacctg accgaagacg     1260 aaaatcgcgtt attttctgca ttcgtactga tgtcagcgga tcgctcgtgg cttcaggaaa     1320
```

```
aaatcgcgtt attttctgca ttcgtactga tgtcagcgga tcgctcgtgg cttcaggaaa     1320
aggtaaaaat agaaaagctg caacagaaaa ttcagctggc ccttcagcac gtcctacaga     1380
agaaccaccg agaagatgga attctaacca agctaatatg caaggtgtct acgttaagag     1440
ccctatgtgg acgacatacg gaaaagctaa tggcatttaa agcaatatac ccagacattg     1500
tgcgactcca ttttcctcca ttatacaagg aattgttcac ttcagaattt gagccagcca     1560
tgcaaatcga tgggtaaatg tcgcgcccga gcacttctag aacatctgga gtacaaacat     1620
gaaagtaaga gagaaaattt ttaaaaaaaa aaaaaaa                              1657
```

<210> SEQ ID NO 29
<211> LENGTH: 2567
<212> TYPE: DNA
<213> ORGANISM: Mus musculus

<400> SEQUENCE: 29

```
aattcagggt aggggttttc tactgaggac ttttcttct tcacagctgc cttctgaaat       60
gtgtggagca actggtggat ggtttcctag cctttcaaag gtagtttaca atgatttga      120 agtgctgatc ctttcagagt ctcaacagat tatttcttaa acagctcata cattgctgtt     180
tatgcatgaa ttagaaccgg ccacgtaga aaacactgtg attgtacctg ggagttggcg      240
agaaaaccag tgctctccct tgattctgct gcacgaggag aatgggctgt gatcggaact     300
gtgggctcat tgctggagct gttattggtg cagtcctggc tgtgtttgga ggcattctca     360
tgccagtcgg agacatgctt attgagaaga caatcaaaag ggaagttgtc cttgaagaag     420
gaaccactgc tttcaaaaac tgggttaaaa caggcaccac tgtgtacaga cagttttgga    480
tctttgatgt gcaaaaccca gatgacgtgg caaagaacag cagcaaaatc aaggttaaac     540
aaagaggtcc ttacacatac agagttcgtt atctagccaa ggaaaatata actcaggacc     600
ccgaggacca cactgtgtct tttgtacagc ccaatggagc catctttgag ccttcactgt     660
ctgttggaac agaggatgac aacttcacag ttctgaatct ggctgtagca gctgcaccac     720
atatctacca aaattcattt gttcaagttg tgctcaactc tcttataaaa aagtccaagt     780
cttctatgtt ccaaacaaga tctttgaaag aactcttgtg gggttacaaa gatccattcc     840
tcagtttggt tccatatcct ataagtacca cagtggtgt gttttatcct acaatgaca       900 ctgtagatgg agtttataaa gttttcaatg gaaaggataa cataagcaaa gttgccataa     960
ttgagtccta taagggaaa aggaatttgt cctattggcc aagctattgc gacatgatta    1020
atggcacaga cgcagcctcc tttccacctt ttgttgaaaa gtctcggaca ttgagattct    1080
```

```
tttcctctga catttgcagg tctatctacg ctgtgttcgg atctgaaatc gaccttaaag    1140
gaatccccgt gtacagattt gttcttccag ccaatgcctt tgcatcaccc ctccagaatc    1200
cagacaacca ttgtttctgc actgaaaaag taatctccaa taactgtaca tcttatggtg    1260
tgctagacat tggcaaatgc aaagaaggaa agcctgtgta tatttcgctt ccacatttcc    1320
tacatgcaag tccagatgtt tcagaaccta ttgaaggctt acatccaaat gaagatgagc    1380
ataggacata cttagatgtg aacccataa ctggattcac tctacaattt gcaaaacgac     1440
tgcaggtcaa catattggtc aagccagcta gaaaaataga agcattaaag aatctgaaga    1500
gaccttacat tgtacctata ctgtggctaa atgagactgg gaccattggt gatgaaaaag    1560
cagaaatgtt caaaacacaa gtgactggga aaatcaagct ccttggcatg gtagagatgg    1620
ccttacttgg gattggagtg gtgatgtttg ttgcttttat gatttcatat tgtgcttgca    1680
aatccaagaa tggaaaataa gtagtggatg agcctacata tacactggct acatctttgg    1740
taaagccgat cacaaaatga aaacttaata tatgcttcgt ttttacaaaa cacacctatc    1800
tttaggagaa gaaatggtgg tgtgtgctct ctctctcttt ctctttctct cttattgcag    1860
atatatattt atttgtaaat atatatatat gcaataagtc acagcatatt tcaaaagatt    1920
aatatgtcac tataggcaat attttttaat aaaatcttgc acttttatta aaagtccatc    1980
atttgcaact gagtggactt caatttctgt agacccaatt atcctgtttg ttctgatttt    2040
actgatttgt tccatgttgg caaatttcaa gaatgtacat tctgagaaat ttttgttttc    2100
cctcactgga ggaaactgct atcatgactg gggtggcccc tttgtttata gcaaatttgg    2160
cttgcaactg tcagcacatg gcataagtat aacatcttga aagacttaag aatgaaaaat    2220
gaacaattca catgtgagcc actgcttata tattaagtct ctccctctct ggagttcttg    2280
gctacagcaa ggccagatat cacattggtt ttggttttgt tgttttgtt ttgttttgt      2340 tttttactct ctgacacaga gcttatgaaa tggacttttt ttttttttt ttttagcat      2400 accttagctc tttgtatttt aagtatgtcg tcatgttcca tgctgcatag ctctttaaaa    2460
aacctgagta ggttttctc tttctgctca gctgcaacta ataacaacct tggagagctg     2520
ttatagtgtt aaaagatgta aatgataata aagaattat taaatgg                   2567
```

<210> SEQ ID NO 30
<211> LENGTH: 1649
<212> TYPE: DNA
<213> ORGANISM: Mus musculus

<400> SEQUENCE: 30

```
gagctgtgct tgtctaggtt ggcgctgaag gatacacaga agcaaatgca cagatcggag      60
atgactccca cggggcagg cctgaaggcc accatcttct gcatcttgac ctgggtcagc      120
ctgacggctg ggaccgcgt atacatccac cccttccatc tcctttacca caacaagagc      180
acctgcgccc agctggagaa ccccagtgtg agacactcc cagagtcaac gttcgagcct     240
gtgcccattc aggccaagac ctcccctgtg aatgagaaga ccctgcatga tcagctcgtg    300
ctggccgccg agaagctaga ggatgaggac cggaagcggg ctgcccaggt cgcaatgatc    360
gccaacttcg tgggcttccg catgtacaag atgctgaatg aggcaggaag tggggccagt    420
ggggccatcc tctcaccacc agctctcttt ggcaccctgg tctcttttcta ccttggatcc    480 ttagatccca cggccagcca gctgcagacg ctgctggatg tccctgtgaa ggagggagac    540
tgcacctccc gactagatgg acacaaggtc ctcgctgccc tgcgggcat tcagggcttg     600 ctggtcaccc agggtgggag cagcagccag acacccctgc tacagtccat tgtggtgggg    660
```

```
ctcttcactg ctccaggctt tcgtctaaag cactcatttg ttcagagcct ggctctcttt      720
acccctgccc tcttcccacg ctctctggat ttatccactg acccagttct tgccactgag      780
aaaatcaaca ggttcataaa ggctgtgaca gggtggaaga tgaacttgcc actggagggg      840
gtcagtacag acagcaccct acttttcaac acctacgttc acttccaagg aacgatgaga      900
ggtttctctc agctgcctgg agtccatgaa ttctgggtgg acaacagcat ctcggtgtct      960
gtgcccatga tctccggcac tggcaacttc cagcactgga gtgacaccca gaacaacttc     1020
tccgtgacgt gcgtgcccct aggtgagaga gccaccctgc tgctcatcca gccccactgc     1080
acctcagatc tcgacagggt ggaggccctc atcttccgga acgacctcct gacttggata     1140
gagaacccgc tcctcgggc catccgcctg actctgcccc agctgaaaat ccgaggatcc      1200
tacaatctgc aggacctgct ggctgaggac aagctgccca ccttttggg tgcggaggca      1260 aatctgaaca acattggtga caccaaccc cgagtgggag aggttctcaa tagcatcctc       1320
ctcgaactca aagcaggaga ggaggaacag ccgaccacgt ctgtccagca gcctggctca     1380
ccggaggcac tggatgtgac cctgagcagc cccttcctgt cgccatccta agagcaggac     1440
tcaggcacgc tgcactttct gggcagagtg aataacccc agagtgtggt gtgaggcctt      1500
gtgcctagcc catggagaca aggccggtgt cggagaaccg ttctgggcaa aactcagtgc     1560 tgtcaccct ggctccccat cacgccttgt agcgcggcag aggccgtctc cttggagact      1620
gcgctgaccg agaataaatg atgagcagc                                      1649
```

<210> SEQ ID NO 31
<211> LENGTH: 1239
<212> TYPE: DNA
<213> ORGANISM: Mus musculus

<400> SEQUENCE: 31

```
gatgaccgca acagtagttg ctgcggctgc cactgcaacc atggtctcca gcagcagcgg       60
cctcgccgcc gcccgcctgt tgtcgcgcac cttcctcctg caacagaatg ggatacgaca      120
cgggtcttac acagcctctc ggaaacatat ctatattgat aaaaatacga agattatttg      180
ccagggtttc acaggcaaac agggtacctt tcacagtcag caggctttgg agtacggcac      240
caaactcgtg ggaggaacca ctccagggaa gggtggccag aagcacctgg gcttgcccgt      300
ctttaatact gtgaaggaag ccaaagagaa acaggagca acggcttctg tcatctatgt       360
ccctcctcct tttgctgctg ctgccattaa tgaagcaatc gacgcggaga ttcccttggt      420
tgtgtgcatt acgaaggta ttccgcagca ggatatggtg cgggtcaagc acagactgac       480
acgccaggga acgacgaggc taatcgggcc aaactgcccc ggcgtcatca accctggaga     540
atgcaaaatc ggcatcatgc ctggccacat tcacaagaag ggaagaatag gtatcgtgtc      600
caggtccggt actctgactt atgaagcagt tcaccaaaca acccaagtcg gattggggca      660
gtccttgtgt attggcattg gaggtgaccc ttttaatggg actgattta ttgattgcct        720 tgaagtcttc ctgaatgatc cagccacaga aggcatcata ctgattggtg aaattggtgg     780
tcacgctgaa gaaaatgctg ccgcgtttct gaaggagcat aactcaggtc caaaggccaa     840
gcctgtagtg tccttcattg ctggtataac tgctcctcct ggcagaagga tgggccatgc     900
aggggcaatt attgctggag gaaaaggtgg cgctaaagag aagatctctg ctcttcagag      960
tgctggggtg gttgtcagca tgtccccgc acagctggga actaccattt ataaggagtt      1020
tgaaaagagg aagatgcttt gaaggacaca acaagaaatt cttaaagct gtggaagaaa      1080 tctagacgtg agggccagtc caggctgtca gcccatgcag ctgacactgg ttggtctctc     1140
```

```
agtatgtggg aaatccaggc aagttttaga atgtcctaaa ttgagctatt ttcacttact    1200
gtgtaacaga gacagataat aaatctatca tttgatttg                          1239

<210> SEQ ID NO 32
<211> LENGTH: 1787
<212> TYPE: DNA
<213> ORGANISM: Mus musculus

<400> SEQUENCE: 32
ggggccctct ttccgacctg cccacggccc cgcccacctg aatgtaggtg aaaggtcggc      60
ggagccgctc gggcagcgga gcaagaccaa gactgcccgg agctgacaga cagacagaca     120
gaagactgag catggcagac gagccgaaac ccatcagtcc gtttaagaac ctcctggctg     180
gcggcttcgg cggcatgtgc ctggtgtttg tggggcaccc cctggacacg gtcaaggtcc     240
gactgcagac acaaccacca agtttgtctg gacagccacc tatgtactct gggaccttgg     300
actgtttccg gaagactctt atgagagagg gcatcacagg gctgtatcgg ggcatggctg     360
cgcccatcat tggagtcacc cctatgttcg ccgtgtgctt cttgggtttt ggtctgggga     420
agaaactaca gcagaaatct ccagaggatg aacttagcta cccacagctg tttacagctg     480
ggatgttatc tggtgtgttc accacaggaa tcatgacccc tggagaacgg atcaaatgct     540
tactgcagat tcaggcttct tcaggggaga caagtacag tggcaccttg gactgcgcaa     600
agaagctgta tcaagagttc gggatccgcg gcttctacaa agggactgtg ctcacactca     660
tgcgagatgt tcctgccagt gggatgtatt tcatgacata tgaatggctt aaaaatctct     720
tcactccaga ggggaaaaga gtggtcagtg acctcagcgt gcctcggatc ctggtggctg     780
gtggctttgc agggatcttc aactgggccg tggcaatccc cccggacgtg ctcaagtctc     840
gattccagac tgcacctcct ggaaaatatc ctaatggttt cagagatgtg ttgagagagc     900
tgatccgaga agaaggagtc acctccttgt acaaagggtt caatgcagtc atgatccgcg     960
ccttcccagc caacgccgcc tgtttccttg gctttgaaat tgccatgaag ttccttaatt    1020
ggattgcccc caacttgtga agctgaagac tcttcaagac ctgtggaagc tggacactgt    1080
tgctgagagg caggggcagg aggaggaagt cctgagaggg aggggaggga agaggtgtga    1140
tcagagctcc aggcttggct gtgatggtga aactgttgcc ttaatgatat cctctacctt    1200
gtataacttg gtgccatttt gaaacttgaa tttagaggat ttccagagaa ttggagatgg    1260
aataaatagt ttatagactc gataccttg gccaaattgc cacctactgg ttgactgaag    1320
gccctgttac actcaaaata ctccttcccg aagaggtgat ggctgactct ctggaggccc    1380
cttgcctact ttcagccagc taaaccagga gctgggatct ttaattgcta gccaggaaaa    1440
ctcaagagat gtctctggtg ccatccatat actcctggct gtgcatggga tgtgggtgtg    1500
aaccacacat ctgtctatcc aatggactgg gtagataata cctaagaaca gcccacctac    1560
taaccatttt ttttttgatat ttttacacaa gaaataataa gaagaaagct acaattgtct    1620
aaatccccag gagaaagtag agaatttttcc ctcctacaca gtgaagacag tcccagcctc    1680
ctgggataag tgtgagagcc ataatgtatg aaggctcctt ttgcacattc tttcccatg    1740 agagcactca gttttaacag gaaacaataa atattgtttc taatttt                1787

<210> SEQ ID NO 33
<211> LENGTH: 1169
<212> TYPE: DNA
<213> ORGANISM: Mus musculus

<400> SEQUENCE: 33
```

```
cggacgcgtg ggcggacgcg tgggtaagtt tccgcgtttc tctcaaccgc agccagcagt      60
gaaaatgtca gcgccagagg gtctgggaga tgctcatggc gacgccgacc gcggcgacct     120
ttccggggac ctccgtagtg tgctggtcac gagcgtgctc aacctcgagc cgctagatga     180
agatctctac agaggaaggc attactgggt acctacctcc cagcggctct ttgggggtca     240
aattatgggc caggcctgg tggctgcagc caagtctgtg agtgaagacg tccatgtcca      300
ctccctgcac tgctactttg tccgggcagg ggacccgaaa gtgccagtgc tgtaccacgt     360
agagaggata cggacaggag ccagcttctc agtgcgcgcc gtgaaggctg tgcagcatgg     420
caaggccatc ttcatctgcc aggcctcctt ccagcagatg cagcccagcc cgctgcagca     480
ccagttctcc atgccctccg tgcccccgcc agaagacctg ctggatcacg aggccctcat     540
tgaccagtac ttaagggacc ctaaccttca caagaagtat cgagtggggc tgaaccgagt     600
tgctgcccag gaggtaccta ttgagatcaa ggtggtgaac ccaccccacc tgacccagct     660
gcaggcactg gagcccaaac agatgttctg ggtgcgtgcc cggggctaca ttggggaagg     720
tgacatcaag atgcattgct gtgtggctgc ttatatctct gactacgcct tcctgggtac     780
agcactgctg ccccaccagt ccaagtataa ggtgaacttc atggcgtcac tggatcactc     840
catgtggttt catgccccat tccgagccga ccactggatg ctgtacgagt gtgagagccc     900
ctgggctggt ggctctcgag ggctggtgca tgggcggctg tggcgtcggg atggggtcct     960
tgctgtgacc tgtgcccagg agggtgtgat ccgattgaag cctcaggtgt cagagagtaa    1020
gctatagtga aagatgcctg gctcggcctg gggctaaaag gactttgcac tgccatttct    1080
gaggcaggag tcacagttga gagctggct tcctgcctct acatacaat aaagagattg      1140 ctaacactgg aaaaaaaaaa aaaaaaaaa                                      1169
```

<210> SEQ ID NO 34
<211> LENGTH: 2795
<212> TYPE: DNA
<213> ORGANISM: Mus musculus

<400> SEQUENCE: 34

```
ggcttcccga agtctcctgc tgctagtaag aggaagtact gcagggctga tgtcgcgacc      60
ttgtggactc ccggagcctg tcaggtaaag ctctccggct ccaagcaccg agcctgacc      120 aagccgggct ctgatcattg cacaggccct atctatccac cctgcagttc aggctcctca     180
gggctcccct ccagccggaa ctttgctctt ctgctcctgg ggacagagtt ggggttttca     240
cctaacaaga ttcacacacg cgcaggcgtg tcctcatctc ccagggtcac agcgtttccc     300
ttttgccaat ccgagtcact cttcaggaac ccccacagcg gaacctcaga accccaacat     360
ggccagacag ttatgcatca gccaaacaga gttcaagttc ctgggtggct tcttccaccc     420
ataaccgagg ttcttgctca aggcattgct gctcccagcc tggcctcagt actacaaggc     480
tgttctgaga actcaacaca gaatgggcca gccctgctcc tattttgatg gtattgtctc     540
gacacaatta gactttat ttcctgctgc ctctgggcag ttctaggggt tgtttaaaag       600
ccttcttcct ctttggctgg ctaattgtct tttctgaca gaggcctgtg agtatcagct      660
gtactgtgtg ccagctttca ttggccctt ccaggacatt tgattggttt gcagccagct     720
ctctgtcaca tggatgggat ggggcttgtg ggggggggg cggtgtttga gaataagcaa     780 accctctaa ccaaaggctt gttaaggatg cgctagtgat taacactcac agctcagggc     840
caccttgttc atgaactggc cactttacct gcacggctac cctcgagcaa gttacagatg     900
aggacttctc gaggctccag gagatgatgg gtagcccagg ctgatctcaa actttcggta     960
```

```
gtcgttctgc ctcagcttct ccaagcacta ggaggttgca ggtgtgagct agttaccgca   1020
cccggctcca cccagctttt gagatggaat gagttctggc tgacctaaac atctggtttt   1080
gcacagtcat actgcggaat agtgagaact aatgttacac tttctacagc cactgtgaca   1140
aagtcctacc aactggatga cttgaggaat agcaattagc ctctcttggg tctgaaggac   1200
ccataatcag gtctgaagtc cataatcaag gtattagcag gcacacaatc agaagtctct   1260
ggggatgttc cattgcccct tccagcttct ggtaactttc gatcatcctt ggcttatagc   1320
agcagatttt gggtcoccat tcccatcgtg ctgtctgtct gtctgtctct ctgtgtgtgt   1380
gtgtgtgtgt gtgtgtgtgt gtgtgtgtgt gtgtgtgtgt acatctatgt ctatagcctc   1440
ttccttcaaa gacacctgtt gttggattgg gagttctccc tacattcagg atggtgcaat   1500
ctcaagagcc ttaactactt acatctgcaa agaacccatt tctgaataac accacattct   1560
caggctctat gttgacatga ataaggtggt cactgtcaca caccatgcaa acaagcagca   1620
taaagcatag agctcatccg agggactcgg aaagagccac atgaaaacag tcccatttgt   1680
ggtgctaaat ctaaactttg gcggtaacta tcagtgatgg tacagtccct tgagctgcca   1740
cagaggcaac cttgtcactt tggaagttgg atcaagcgct caccctcggg cctcacctca   1800
aagtcaccga gtcaggtttt gggaaacaat ctgatagatg atgccaaggc tcgcctgaga   1860
aagtctgatg tcgggaccag atattctcac ctgtcctcta ataaattctc tgtccttgta   1920
ccactgctgg ccagaggagg aaagttgtat ttgatgttca cggtccgctc agacaagctg   1980
aaaagggaac ctgagaagt ctgcttccct ggaggaaaga gggacccggt ggacacagat   2040
gacacagcca ctgctctccg tgaagcccag gaggaggtgg ggctgcatcc ccaccaagtg   2100
gaggtggtct ctcacctggt gccatacgta tttgataatg atgcactggt aaccccgta    2160 gtgggttttc tagaccacaa cttccaggcc caacctaatg ctgatgaagt gaaggaagtc   2220
ttctttgtgc ctttggacta tttcctccat ccccaagtct actaccagaa gcaaatcaca   2280
cagtctggcc gtgatttcat catgcattgc ttcgagtaca aagaccctga gactggtgtg   2340
aactacctaa tccagggaat gacctcgaaa ctggctgtgt tggtggcctt aattattttg   2400
gaacaaagtc ctgccttcaa gattgatttt gatctccatg acctgatacc gtcttgtgaa   2460
aggaccttcc tttggagata ttcttaagc aagttgtgaa gacccttgaaa cccaaaagaa    2520 cgtacatgag gttttgtgt gagcttatgc tcagaacaac agtgtttagc aagtggcatc    2580
tgacaggtgt gaatattttc ctacaatgtg gctgtgagat ccttgcctga cttcctgttg   2640
ctgctttaga acactaaaag tttttcaaaa ctggaaaaat gcactggcag gggagaataa   2700
ttttacccat ttaaaaaaat ggcacgattt ttagtcatat tagggaaatt tgtcacatag   2760 taggcccctta ataatattt gtcaaatata tggct                              2795
```

<210> SEQ ID NO 35
<211> LENGTH: 2998
<212> TYPE: DNA
<213> ORGANISM: Mus musculus

<400> SEQUENCE: 35

```
ctgtcagcca actgattgca gatgtggttg gcattggagg aaccagattc cagcagtcct     60
tgtctatcat caacaactgt gccaacagcg accggatcat caagcacacc agcttttcct    120
ctgatgtgaa agatttgact aagaggatcc gcacagtcct gatggccaca gcccagatga    180
aggagcacga gaacgacccg gagatgctgg tggacctcca gtacagcctg ctaagtcct     240 acgccagcac ccctgagctc aggaagacgt ggctagacag tatggcgagg attcacgtta    300
```

| | | | | |
|---|---|---|---|---|
| aaaatgggga | cctctcagag | gcggcaatgt | gctatgtcca | cgtgacagcc | ttggtggcag | 360 |
| aatatctcac | acggaaaggc | atgttcagac | aggggtgcac | agccttcagg | gttatcacac | 420 |
| caaacatcga | tgaagaggct | tccatgatgg | aagacgtcgg | catgcaggac | gtccatttca | 480 |
| acgaggatgt | gctgatggag | ctgctggagc | agtgtgcgga | tggactttgg | aaggcggagc | 540 |
| gctatgagct | gatcgctgac | atctataagc | tcatcatccc | catctacgaa | aagcggaggg | 600 |
| atttcgagag | actagcccat | ctgtatgaca | cgctacaccg | cgcatacagc | aaagtgacag | 660 |
| aggtcatgca | ctcgggccgc | aggctcctgg | ggacctactt | ccgggtggct | ttctttggac | 720 |
| aggggttctt | cgaagacgaa | gatgggaagg | aatacatcta | caaagagccc | aagctcacgc | 780 |
| ctctgtcaga | gatttctcag | agactcctta | aactttactc | ggataaattt | ggttccgaaa | 840 |
| atgtcaaaat | gatacaggat | tctggcaagg | tcaacccgaa | ggatctggac | tccaagtttg | 900 |
| cctacatcca | ggtgacccac | gtgacccccat | tctttgacga | aaaggagtta | caagagagga | 960 |
| gaacagagtt | tgaacgatgt | cacaaacatcc | ggcgcttcat | gtttgagatg | cccttcaccc | 1020 |
| agaccgggaa | gaggcagggt | ggcgtggagg | agcagtgtaa | gcggcggacc | atcctgacag | 1080 |
| caatacactg | cttcccctac | gtgaagaagc | ggatccctgt | catgtaccag | caccacactg | 1140 |
| acctgaaccc | cattgaggtg | gccatcgatg | aaatgagcaa | gaaggtggcc | gagctccgcc | 1200 |
| agctctgctc | gtcggctgaa | gtggatatga | tcaaactgca | gctcaaactg | cagggcagtg | 1260 |
| tgagcgtcca | ggtcaatgct | ggtccgctag | catatgcccg | agccttcctc | gatgacacca | 1320 |
| acacaaaaag | atacctgac | aataaggtga | aactgctgaa | ggaagttttc | aggcaatttg | 1380 |
| tggaagcttg | tggtcaagcc | ttggcagtga | acgagcgtct | cattaaagaa | gaccaactgg | 1440 |
| agtaccagga | agagatgaag | gccaactaca | gggagatggc | caaggagctc | tccgacatca | 1500 |
| tgcgtgagca | gatttgcccc | ctggaggaga | agacaagcgt | gctaccaaat | tccctgcaca | 1560 |
| tcttcaacgc | catcagcggg | acaccaacaa | gcacagtggt | tcaagggttg | accagctcgt | 1620 |
| cctcagttgt | gtgattttac | ctcatgaacc | gtgtgtgggg | acatgctttg | tcatgtgcaa | 1680 |
| actcaggatg | acttccagag | ctaatcactg | gtgtggccaa | gcacaggaag | aagccatggg | 1740 |
| gaatgggaga | gagaaggagc | ctggactgtg | atatttaata | gcagatttta | taggagtcgg | 1800 |
| gggaaggtgc | acatagtttt | ttaaatctca | ctggcaatat | ttagttttcc | tcatgtctta | 1860 |
| acaggtatat | gtggatactc | ttgagctgaa | gttcagtttt | attcttctta | cagtatagta | 1920 |
| ttaaaataaa | tggtctaaag | gaaaagaggg | aaagtgtgct | gggacacctg | tggcaggtgt | 1980 |
| cctgggatac | ctgtagcagg | tgtcctggga | cacctgtagc | aggtgtgctg | ggacacctgt | 2040 |
| agcaggtgct | gggacacctg | tagcaggtgt | tgctgggact | gggacacctg | tagcaggtgt | 2100 |
| tgctgggact | gggacacctg | taacaggtgt | tgctgggact | gggacacctg | tagcaggtgt | 2160 |
| tgctgggact | gggacacctg | tagaaggtgt | cctgggactg | ggacacctgt | agcagacaaa | 2220 |
| gcagcactga | acctggggtt | ggggactaag | ctggaaaaat | cttgaaaata | tttttctccc | 2280 |
| tggggcacat | tcaggttgag | tacaagaact | atttttgtgt | ctaattttga | tgacggaaag | 2340 |
| gaattgccta | ttgtaatttt | gtactagtga | atgaggagac | ttagagcctt | tatattcatg | 2400 |
| ccttgtgttg | gcaacatgag | cacttcagaa | gctgagtgtg | agcctaagcc | tagtcagcat | 2460 |
| tatagaacca | aaggcctgta | ctagcaaaca | cacccatgct | aaaacctaaa | accccatgta | 2520 |
| catactgact | gtcaatacag | cctccttgct | atgtccacac | actcaccaca | tttctacact | 2580 |
| tttaatacgc | cagtgtccat | gttaagttta | ttattcgtgg | cccatttgtg | ctgttctcag | 2640 |
| tatatgcaaa | cacattggac | ttcactgttt | attcttgtac | ataagaagtg | caatatggag | 2700 |

```
atgtatacag tctttgctat attaggttta taaactgttt taaaaaaatt catccttttg    2760
ccaaaatgat gaactaagtg attggtaaac cctaagccct gtatgagtgg agggatagtt    2820
taaagttttc accatgttat attttctttt gagactttaa tttagtaatt ttatatttgg    2880
gaaaaaaaat aaaggttttt aatttaactg gaatcactgc cctgctgtaa ttaaatatcc    2940 tgtacccaa ctgtattaaa ataacattg ctgattttct ggtaataaaa aaaaaaa        2998
```

<210> SEQ ID NO 36
<211> LENGTH: 2103
<212> TYPE: DNA
<213> ORGANISM: Mus musculus

<400> SEQUENCE: 36

```
aagacttcgg cggcggcctt tggagatgca gtcggctcgg atgaccccga gtgtggggcg      60
acagctgctg cggctggggg cccgaagctc gcgatctact actgtgcttc agggacaacc     120 ccggccatc tctgcccagc gactttatgc cagggaggcc actcaggcag ttctggacaa     180
gccagaaacc ctctcctctg atgcttccac cagagaaaaa ccagccaggg cagaatcgaa     240
gtcctttgct gtggggatgt tcaaaggcca gcttaccatt gatcaggtgt tcccataccc     300
atctgtgctc agtgaagaac aggcacaatt tctcaaagag ctggtgggac cagtggcccg     360
gttctttgag gaagtgaatg accctgccaa gaacgacgcc ttggagaagg tggaggacga     420
cactttgcag ggactcaagg aactgggggc atttggcctg caagtaccca gcgagctggg     480
tggtttgggc ctctctaata cccagtatgc tcgcttggca gagattgtgg gcatgcatga     540
ccttggtgtt agcgttaccc tgggagctca tcagagcatc ggtttcaaag gcatcttgct     600
ctatggcaca aaggcccaga gagaaaaata ccttcccaga gtggcatctg ggcaggcttt     660
ggctgctttc tgcctaacag agccctcgag tggatccgat gtagcctcca tccgaagctc     720
agccataccc agccctgtg gaaaatatta cactctcaat gggagcaaga tctggatcag     780 taatggggc ctggctgaca ttttcactgt cttttgccaag acgccaatta agatgcagc     840 cacgggggcc gtgaaagaga agatcacagc ttttgtagtg gaaaggagct cggaggggt     900 tacccatggg ctcccctgaaa agaagatggg catcaaagca tctaacacgt cagaggtgta     960
ctttgatgga gtgaaggtgc catcagagaa tgtgctagga gaggtgggag atggcttcaa    1020
ggttgctgtc aacatcctca acaacggaag attcgggatg gctgcaaccc tcgcaggcac    1080
catgaaatcc ctcattgcca aggcggttga tcatgctact aatcgtaccc agtttgggga    1140
caaaattcac aactttgggg tgatccagga aaagctggct cggatggcta ttctgcagta    1200
tgtgactgag tccatggctt acatgctgag tgccaacatg gaccagggat tcaaagactt    1260
ccagatagaa gccgccatca gcaaaatctt ttgctcggag gcggcctgga agtggcaga    1320 tgagtgcatc caaataatgg ggggcatggg cttcatgaag gaaccagggg tggagcgtgt    1380
gctccgagat attcgaatct tccggatctt tgaagggca aatgacattc ttcgactgtt    1440
tgtggctctg caaggctgta tggacaaagg aaaggaactc actgggctgg gcaatgccct    1500
gaagaatcct tttggaaacg ttggcctcct gatgggagaa gcaggcaaac agctgagacg    1560
gaggacagga atcggcagtg gtttgagtct gtcaggggatt gtccacccag agttaagtcg    1620
cagtggtgaa ctggcagtgc aggctctgga tcaatttgcc accgtggtgg aggccaagct    1680
ggtgaaacac aagaaaggga ttgtcaacga gcagttcctg ctgcagcgac tggcggacgg    1740
cgccattgac ctctatgcca tggtggtggt tctgtccaga gcctcaaggt ccctgagtga    1800
gggctacccg acggcacagc atgagaaaat gctctgtgat agctggtgca ttgaggctgc    1860
```

```
aactcggatc cgagaaaaca tggccagtct gcagtccagc cctcagcatc aggagctctt    1920
ccggaacttc agaagcatct ccaaggccat ggtggagaat ggtggcctgg tcaccggtaa    1980 cccccctggga atctgagact cccaatcagg ccctggcaag gtcatgtgcc ttctctgatg    2040
ccaaaaccct ttatgggggt gatggagtac ttattgcctt aacaataaat tttctaccaa    2100
gtc                                                                  2103
```

<210> SEQ ID NO 37
<211> LENGTH: 3187
<212> TYPE: DNA
<213> ORGANISM: Mus musculus

<400> SEQUENCE: 37

```
cggagctcag ggctgaagat ggttcctctc ctgcccttat atgctctgct gctgctgttc     60
ctgtgtgata ttaaccctgc aaatgccaac agttactatg acaaggtcct ggctcacagc    120
cgcatcaggg gtcgggatca gggcccaaac gtctgtgccc tccagcaaat tctgggcacc    180
aaaaagaaat acttcagctc ctgtaagaac tggtatcaag gtgctatctg cgggaagaaa    240
accactgtgc tatatgaatg ctgccctggc tatatgagaa tggaagggat gaaaggctgc    300
cccgcagtga tgcctattga ccatgtttat ggcacgctgg gcattgtggg agccactacc    360
actcagcact actccgatgt ctcgaagctg agagaagaga ttgaaggaaa agggtcatac    420
acgtacttcg cgccgagtaa cgaggcttgg gagaacctgg attctgacat cgcagagga    480 ctggagaaca atgtcaatgt tgagctactg aatgccttac acagccacat ggttaataag    540
agaatgttaa ccaaggacct gaaacacggc atggttattc cttcaatgta caacaatctg    600
gggcttttta ttaaccatta tcccaatggg gttgtcactg tgaactgtgc tcgagtcatc    660
catgggaacc agattgccac aaatggtgtc gtccatgtca ttgaccgtgt cctgacacaa    720
attggtacct ccatccaaga cttccttgaa gcagaagacg accttccatc atttagagca    780
gccgccatca cctctgacct cttggagtcc cttggaagag atggtcactt cacgctcttt    840
gctcccacca atgaagcttt cgagaaactg ccacgaggtg tcctagaaag gatcatggga    900
gacaaagtgg cttctgaagc tctcatgaag taccacatcc taaatacct ccagtgctct    960 gaggccatca ctggaggagc cgtgtttgag accatggaag gaaacactat tgagataggg    1020
tgcgaagggg acagtatctc cattaacgga atcaagatgg tgaacaagaa agacattgtg    1080
actaagaatg gtgtcatcca cctgattgat gaagtcctca ttcctgattc tgccaaacaa    1140
gttattgagc tggctggaaa cagcaaacc actttcaccg acctggtagc ccaattaggc    1200
ttggcatcct ctctgaagcc agatggagag tacaccttat tagcacctgt gaacaatgcg    1260
ttctctgatg acactctgag catggaccaa cgccttctta agctaattct gcaaaatcac    1320
atattgaaag taaagttgg ccttagcgac ctctacaatg acagatact ggaaccatt    1380 ggaggcaaac aactccgagt ctttgtgtat cggacggcta tctgcataga aaactcatgc    1440
atggtgagag aagcaagca gggaaggaat ggtgccattc acatattccg agaaatcatc    1500
caaccagcag agaaatccct gcacgacaag ctgcggcaag acaagcgctt tagcatcttc    1560
ctcagcctcc ttgaagctgc agatttgaaa gatctcctga cacagcccgg agattggacc    1620
ttgtttgcac caaccaatga tgccttcaag ggaatgacta gcgaagaaag ggagcttctg    1680
attggggata aaaatgctct ccaaaacatc attctttatc acctgacccc aggggtttat    1740 attgaaagg gattcgaacc cggagtcact aatatcctga agaccacaca gggaagcaaa    1800
atctatctga aaggagtaaa cgaaacgctt ctagtgaatg agttgaagtc caagaatct    1860
```

```
gacatcatga cgacaaatgg tgtcatccac gtcgtggaca aactcctcta tccagcagat    1920
attccagttg gaaatgatca gctcttggaa ttactgaaca aactgataaa atacatccaa    1980
atcaagtttg ttcgtggcag caccttcaaa gaaatcccca tgactgtcta tagacctgca    2040
atgacgaaga tccaaattga aggtgatccc gacttcaggc tgattaaaga aggcgaaacg    2100
gtgacagaag tgatccacgg agagccagtc attaaaaagt acaccaaaat catagatgga    2160
gttcctgttg aaataactga aaacagact cgggaagaac gaatcattac aggtcctgag    2220
ataaaatata ccaggatttc cacaggaggt ggagaaacag agagacctt gcagaaattc    2280 ttgcaaaaag aggtctccaa ggtcacaaag ttcattgaag gtggcgatgg tcacttattt    2340
gaagatgagg agattaaaag actgcttcag ggagacacac ctgcaaagaa gataccagcc    2400
aacaaaaggg ttcaagggcc tagaagacga tcaagagaag gccgttctca gtgaaaaccc    2460
agaggccaga ccacagagtt tatataatcc taaatcaacg atctgatttt aagggaaatt    2520
gtaagagcca ccacactgac ttcagaatct gaaatgacaa ccaacagaag ccaatcttca    2580
agcaagtcca acacagagt tcatgtcttt gtttctgcat gagaaatata agaaaatgat    2640
agctagtctc ctgtgggta ggaactgagg aaatatagga ccatgcaggg attttatctc    2700
aatgagaaaa cttctgatta aagtagaatc caccaaagaa catcattgtg actgggtcca    2760
tacagctaag tctttgcaca gtaaaaacct tccgcctcag gaagaggctg gaaaaaccca    2820
aagcacacag ttacctttcc aggggaggct aaggtatcaa aaggggtgtt cagttataca    2880
acatgcaaac aaacctacca aattacgaac agtggtgtta catatttctc atgcaatgtg    2940
ggtttcctgc taaattttgt tattttttaca cttgatttat atcctcgaga tgattgtcat    3000
aagcttcttg caatacaaat gttttctctc aaacattttca ataaaaccat tcttcaggta    3060
taaagagaat tactgcagag ttggtaattc agaaaactca aggtttaagt taaaagtgag    3120
tttagacttt ggaataggac ttcatacct tttttattgt taacaagtac tcaataaagt    3180
aaactga                                                              3187
```

<210> SEQ ID NO 38
<211> LENGTH: 1871
<212> TYPE: DNA
<213> ORGANISM: Mus musculus

<400> SEQUENCE: 38

```
ggtcctgcga gtttagccat ggcgctcagc tttctctctc caagcctttc ccgcctcggc     60
ctgtgggctt ctgtagtgat cctgatggta accgtcctga agctcctcag cctgctgttt    120
cggaggcaga agctggccag ggcttttggac agcttcccag gccccccaa gcactggctt    180 tttggtcatg cccttgagat ccagaagaca ggaggcctgg acaaggtggt aacttggacc    240
gaacagttcc cctatgccca cccactctgg cttggacaat ttattgtttt cctgaacatc    300
tatgagcctg actatgctaa agctgtatac agccgagggg acccgaaggc tgcatatgtg    360
tatgacttct cctccagtg gatcggaaaa ggcctactgg ttctggaagg gccaaaatgg    420
ttccagcacc gcaagctgct cacacctggc ttccattatg atgtgctgaa gcccctatgtg   480 gccatatttg ctgagtccac acgggtgatg ctggacaagt gggagaaaaa ggctagtgag    540
aataagagct ttgacatctt ctgtgacgtg gccacatgg cactgacac cctcatgaag    600 tgcacctttg gcaaaggaga cagcggccta agccacagtg acaacagcta ctacctggca    660
gttagtgacc tcacactgct gatgcagcag cgcatcgact ccttccagta ccataatgac    720
ttcatttact ggctcacacc acatggccgc cgtttcttgc gggcctgcca gatagcccat    780
```

| | |
|---|---|
| gaccatacag atcatgtcat caggcagcgg aaggcagctc tgcaggatga aaggagcag | 840 |
| aaaaagcttc aggagcggag acacctggac ttcctcgaca ttctcctggg tgcccgggat | 900 |
| gaaagtggga tcaagttgtc agatgcagac ctccgggctg aagtggacac attcatgttc | 960 |
| gaaggccacg acaccaccac tagtggtatc tcttggtttc tctactgcat ggcccttat | 1020 |
| cctatgcacc agcagcgatg tagggaggag gtccgtgaga tcctagggga ccggactcc | 1080 |
| ttccagtggg atgatctggc ccagatgacc tacctgacca tgtgcatgaa ggagtgcttc | 1140 |
| cgcctctacc cacctgtacc ccaagtgtac cgccagctca gcaagccagt aacctttgtg | 1200 |
| gatggccgct ctctacctgc aggcagcctg atctctctgc acatctatgc cctccatcgg | 1260 |
| aacagtgctg tgtggcctga cccagaggtc tttgacccac tgcgcttttc tcctgagaat | 1320 |
| atgacaggac ggcatccctt tgccttcatg ccttttctg cagggccag gaattgcatt | 1380 |
| gggcaacagt ttgccatgaa cgagatgaag gtggtcacag ccctctgttt gctgcgcttt | 1440 |
| gaattctctc cagatccctc aaagatcccc attaaggtcc cccagctgat cttgcgctcc | 1500 |
| aaaaatggca tccacctcta cctgaagcca ctgggccctg gtctggaaa gtaggtctta | 1560 |
| ggagagcaag gatatggagt cattgtggat ccctgcctgt gggggttg tgagatataaaa | 1620 |
| gcatgcacat tgagagtatc ctggaagaca ttctcttgta acatgtgtg tggaatgatt | 1680 |
| caatgcctgg gctttcaaac tcattccttc actccacaaa tatttgctga atgtttccct | 1740 |
| gtcttgagaa acttcattta tttctcataa ctgcatttat ttagccatct cagtgtgcat | 1800 |
| tttggatata atagacataa ggaaaattgc ttaaactaaa tctgtacaaa ataaataata | 1860 |
| ctttaaaaag c | 1871 |

<210> SEQ ID NO 39
<211> LENGTH: 11009
<212> TYPE: DNA
<213> ORGANISM: Mus musculus

<400> SEQUENCE: 39

| | |
|---|---|
| gacctctact gcaagctggt tgggggtccg gtggctggcg gagatcccaa tcagacaatc | 60 |
| cagggccagt actgtgacat ctgtacagct gccaacagca acaaggcaca ccctgtgagc | 120 |
| aacgccatcg atggcacgga gcgctggtgg cagagcccac ccctgtcccg tggcctggag | 180 |
| tacaatgagg tcaacgtcac actggacctg gccaggtgt tccatgtggc ctatgtgctc | 240 |
| atcaagtttg ccaactcacc tcggcctgac ctctgggtgc tggagcggtc cacagacttc | 300 |
| ggtcacactt atcagccgtg gcagttcttt gcctcctcca gagggattg tttggagcgg | 360 |
| tttggacctc ggactctaga gcgcatcacg caggacgacg acgtcatctg caccacagaa | 420 |
| tactcgcgaa tagtgccttt ggagaatggc gagattgtgg tgtccttggt aaatgggcgc | 480 |
| cctggggcct tgaacttctc ctactcaccg ttacttcgag acttcaccaa agccaccaac | 540 |
| atccgcttgc ggtttctgcg aaccaacacg ctactgggcc acctcatggg caaggcgctg | 600 |
| cgggacccca cagtcacccg caggtattat tacagcatca agacatcag cattggtggg | 660 |
| cgctgtgtct gtcatggcca cgcagatgtc tgtgacgcca aggaccccat tggatccttc | 720 |
| aggctgcagt gtgcctgcca gcacaataca tgtgtggagct cttgtgaccg atgctgtcca | 780 |
| ggcttcaacc agcagccgtg gaagcccgcc accacggaca cgccaatga gtgccagtcc | 840 |
| tgcaattgcc acggccatgc ctacgactgt tactacgacc ctgaggtgga tcggcgcaat | 900 |
| gccagccaga accaggacaa cgtgtaccag ggtgaggtg tctgcctgga ttgccagcat | 960 |
| cacactacgg gtatcaactg tgagcgttgt ctgcctggct tcttccgtgc ccctgaccag | 1020 |

```
cctctcgact cacctcatgt ctgtcggccc tgcgactgtg agtcagactt cacggatggg   1080
acctgtgaag acttgacggg ccgctgttac tgcaggccga acttcacagg agagctatgt   1140
gctgcctgcg ctgagggcta cacggacttc ccacactgct accctctgcc ttcatttcct   1200
cacaatgaca cgagagaaca ggtgcttccc gctggacaaa tcgtgaactg tgattgcaat   1260
gctgcaggga cccagggcaa tgcctgccgg aaggacccaa ggttgggacg tgtgtctgc    1320 aaacccaact tccggggtgc ccactgtgag ctctgtgctc ctggattcca cgggcctagc   1380
tgccacccat gccagtgttc cagccctggg gtagccaaca gcctctgtga cccagagtct   1440
ggccagtgca tgtgccgcac cggctttgag ggggacaggt gtgaccactg tgcccttggc   1500
tatttccact ccctctctg tcagctgtgt ggctgcagcc cagcagggac cctgcctgaa    1560
ggctgtgacg aggctggccg ctgccagtgc cgacctggct tgacggtcc tcactgtgac    1620 cgatgccttc caggatacca tgggtatccc gactgtcacg cttgtgcctg tgaccctcgg   1680
ggggccctgg atcaacagtg tggagtgggc ggtttgtgcc actgccgtcc tggcaacaca   1740
ggtgccactt gtcaggaatg tagccccggc ttctacggct ccccagctg catcccctgc    1800 cactgctctg ccgatggctc cttgcataca acctgtgacc cgacaaccgg ccagtgtagg   1860 tgtcgaccc gagtgacagg actacattgt gatatgtgtg taccaggcgc ctataacttc    1920
ccctactgtg aagctggctc ttgtcatcct gctggtctgg ccccagccaa tcctgccctt   1980
cctgagacac aggctccctg tatgtgccgg gctcacgtgg aagggccaag ctgtgatcgc   2040
tgtaaacctg ggtactgggg gctgagcgcc agcaaccctg aaggctgcac acgctgcagc   2100
tgtgacccac gaggcaccct gggtggagtt actgagtgcc agggcaatgg gcagtgcttc   2160
tgcaaggctc acgtgtgtgg caagacctgt gcagcctgca aggatggctt ctttggcctg   2220
gattatgctg actactttgg ctgccgtagc tgtaggtgtg atgttggtgg tgccctgggt   2280
cagggctgtg aaccaaagac aggtgcctgc aggtgccgcc ctaacaccca aggacccacc   2340
tgtagcgagc cagcgaagga ccactacttg ccagacctgc accacatgcg gctggaacta   2400
gaggaggcgg ccactcccga gggccacgct gtacgctttg gcttcaaccc cctggagttt   2460
gagaacttta gctggagagg ctacgcacac atgatggcta tccagcccag gattgtggcc   2520
aggctgaacg tgacctcccc tgacctcttt cgactggttt tccgatatgt caaccgtgga   2580
tcaaccagcg tgaatgggca gatctctgtt cgtgaagagg gcaagctttc cagctgtacc   2640
aactgcacag agcagagcca gccagtggct ttcccaccca gcactgagcc tgcctttgtc   2700
actgtgcccc agaggggctt tggggaaccc tttgtgctga accccggcat ctgggccttg   2760
ctggtcgagg ctgaaggtgt acttcggac tacgtggtcc tactgcccag cacctactat    2820
gaggcagctc tcctacagca tcgagtaacg gaggcctgta cctaccgtcc ctcagccctg   2880
cactccacag agaactgtct tgtctatgct cacctacccc tggatggctt cccttcagca   2940
gctggaactg aggccctgtg tcgccatgac aacagcctgc cccggccctg ccccacagag   3000
cagctcagcc cctcacaccc accgctggcg acctgcttcg gcagtgatgt ggacatccag   3060
ctcgagatgg ccgtgcctca gcctggccaa tatgttctcg tggtggaata tgtcggtgag   3120
gattcacacc aagagatggg agtggctgtg cacacccctc agagagcccc ccagcaaggg   3180
gtgctcaacc tccaccctg cccatacagc tccctgtgcc ggagtccggc tcgggacacc    3240
cagcatcatc tagccatctt ccacctggac tctgaggcta gcatccggct cacagctgag   3300
caagctcact tcttcctgca cagcgtcacc ctggtacctg tggaggagtt cagtactgag   3360
tttgtggagc ccgggtctt ctgtgtgagc agtcatggaa cttcaacccc cagcagtgct    3420
```

```
gcctgtctag cctcccgatt cccgaagcca ccgcagccca tcatccttaa ggactgccag   3480
gtcttgccgc tgcctcccga cctgcctctg actcagtctc aggagctctc accaggtgca   3540 cccccgagg gaccacagcc tcggccgcca actgcggtgg atcctaatgc agaacccacc   3600
ttgctgcgcc accccaggg cacggtggtc ttcaccaccc aggtgccac cctgggccgc    3660 tatgccttcc tgctgcacgg ctaccagccg gtccaccct ccttccctgt ggaggtactc    3720
attaatggtg gccgcatctg gcagggccac gccaacgcca gcttttgtcc tcatggttat   3780
ggctgccgta ccctggtgtt gtgtgagggt cagacgatgc tggatgttac agacaacgag   3840
ctcaccgtga ctgtgcgtgt gccagaaggc cggtggctct ggctggacta cgtactcatt   3900
gtccctgagg atgcttacag ctccagttac ctccaagagg agcctttgga caaatcctat   3960
gacttcatca gccactgtgc cacccagggc taccacatta gccccagcag ctcatctcca   4020
ttctgccgga atgccgccac ctccttgtct ctcttctaca acaacggggc cctcccttgt   4080
ggctgccacg aggtgggtgc cgtaagcccc acgtgcgaac ccttcggggg ccagtgtccc   4140
tgccggggcc acgttattgg ccgtgactgt tcccgctgtg ccaccggcta ctggggtttc   4200
cccaactgca ggccctgtga ctgtggagcc cgcctgtgtg acgagctcac gggccagtgt   4260
atctgtccac cacgcactgt tcccctgac tgcttggtct gccagccaca gagctttggt    4320
tgccacccct tggtgggctg tgaggagtgt aactgctcag ggcccggcgt ccaggagctg   4380 acggaccta cctgtgacat ggacagcggc cagtgcagat gcagacccaa tgtagctgga    4440
cgtcgctgtg atacctgtgc cccgggcttc tatggctatc ctagctgtcg ccctgtgac    4500 tgccatgagg caggcaccat ggctagcgtg tgtgacccc tcacaggcca atgccattgc    4560
aaggagaacg tgcagggctc aagatgtgac cagtgtcgcg tgggaccctt ctccttggat   4620
gctgctaacc ccaagggctg tacccgctgc ttctgtttcg gggccacaga gcgctgtggg   4680
aactctaacc tcgcccgcca tgagttcgtg gacatggagg gctgggtgct gttgagcagt   4740
gaccggcagg tggtaccccca cgagcatcgg cctgagatag agctgctgca cgcagatctg   4800
cgctctgtgg ctgacacttt tcagagctg tactggcagg ctccgccctc ctatctggga    4860
gacagggtgt catcctacgg tggaaccctc cactatgagc tgcactcaga gacccagcga   4920
ggtgatatct tcattcccta cgagagccgg ccggacgtcg tgctgcaggg caaccaaatg   4980
agcatcgcct tcctggaact ggcgtaccct ccgcctggcc aggttcaccg aggacagcta   5040
cagctggtag aggggaactt ccggcacttg gagactcaca accccgtgtc ccgagaagaa   5100
ctcatgatgg tgctggccgg cctggagcag ctgcagatcc gtgctctctt ctcgcagacc   5160
tcttccagtg tctccttgcg tagagtggta ctggaggtgg ctagcgaggc tggtaggggg   5220
cctccagcca gcaatgtgga actgtgtatg tgccctgcca actaccgtgg ggactcgtgc   5280
caggaatgtg cccctggcta ttaccgggac accaagggtc tcttcctagg ccgatgtgtc   5340
ccctgtcagt gccatggcca ttcagatcgc tgccttcctg gctctggcat ttgtgtgggc   5400
tgccagcaca acacagaagg ggaccaatgt gagcgctgta ggcctggctt tgtcagcagt   5460
gatcccagta accctgcatc cccatgtgtg agctgcccctt gcccttggc agtgccctcc   5520 aataattttg cagacggttg cgtcttaaga aatggccgaa cccagtgcct ctgcaggcca   5580
ggctatgctg gtgcctcctg cgagcggtgt gcacctggct tttttgggaa ccccctggtg   5640
ctaggcagct cctgtcagcc ctgcgactgc agcggtaatg gagacccaa catgatcttc   5700 agtgactgcg accccctgac gggtgcctgt cgaggctgcc tccgtcacac cactgggccc   5760
cactgtgaac gctgtgcccc aggcttctat ggcaatgctt tgttgccagg caactgcacc   5820
```

```
cggtgtgact gttccccatg tgggacagaa acctgtgatc cccagagtgg acgctgcctg   5880
tgcaaagcag gcgtgactgg acaacgttgt gaccgctgtt tggaaggata cttcggtttt   5940
gagcaatgcc agggctgccg cccttgtgcc tgtggaccag ctgccaaggg ctccgagtgc   6000
caccctcaga gcggtcagtg tcactgccag ccagggacca caggacccca gtgcctcgag   6060
tgcgccctg  gctactgggg cctcccagag aagggctgca ggcgctgcca gtgtccccga   6120
ggccactgtg acccacacac gggccactgc acctgtcccc cggggctcag cggggaacgc   6180
tgtgacacct gcagccagca gcaccaggtg cctgtaccgg caagcctggg ggccatggc   6240
atacactgtg aagtgtgtga ccactgtgtg gttctccttc tggatgacct cgagcgggct   6300
ggtgccctcc tccccgctat ccgtgagcag ctgcagggta tcaatgccag ctccgcggcc   6360
tgggccaggc tgcacaggct gaatgcctcc attgctgacc tgcagagtaa actccggagg   6420
ccaccgggac cccgctacca ggcagcacag cagctacaga ctctagagca gcagagtata   6480
agccttcaac aggacacgga gaggctgggc agtcaggcca gggggtccaa ggtcaggca   6540
ggccagctac tggacaccac agagtccaca ctgggccggg cacagaagtt gttggagtct   6600
gtgcgagctg tgggccgtgc cctgaatgag ctggcatctc gcatgggcca aggatctcca   6660
ggcgatgcct tggtaccgtc tggcgagcag ctgcgctggg ctctggctga agtggagcgg   6720
ctgctctggg atatgcggac gcgtgacctg ggggcccagg gggcagtggc agaggccgaa   6780
ctggccgaag cccagaggct gatggctcgt gtccaggagc agctgaccag cttctgggag   6840
gagaaccagt cattggccac acacattcgg gaccagctgg ctcagtatga gtctggcctc   6900
atggatcttc gtgaggccct gaaccaggcc gttaatacca cccgggaggc tgaggaactc   6960
aacagccgca accaggaacg ggtgaaggaa gccctgcaat ggaaacagga actgtcccag   7020
gacaatgcca ccctgaaggc cactcttcaa gctgccagtc tcatcttggg ccatgtttct   7080
gagcttctgc agggcataga ccaggctaag gaggacctag agcacctggc ggccagcctg   7140
gatggagcct ggacaccctt actgaagagg atgcaggcct tttcccctgc cagcagcaag   7200
gtggacttgg tagaggctgc tgaggcccac gctcagaagc tgaaccagct ggcaatcaac   7260
ctgtctggca tcatccttgg catcaatcag gaccgcttca tccagagggc tgtggaagcc   7320
tccaatgcct acagcagcat ccttcaggcc gttcaggctg ccgaggatgc ggcaggccag   7380
gcactgaggc aggccagccg cacatgggag atggtggtgc agcggggcct agcagctgga   7440
gcccggcagc tgttagccaa cagcagtgcc ctggaggaga ccatccttgg acaccagggg   7500
aggctgggcc ttgctcaggg ccgtctgcag gctgcgggga tccagcttca taatgtctgg   7560
gccaggaaga accagctagc agcccagatc caggaggcac aagccatgct ggccatggac   7620
acgagcgaga ccagtgagaa gattgctcac gccaaggctg tggctgccga agccctcagt   7680
acggccaccc acgtgcagtc tcagcttcag ggtatgcaga agaatgtgga gaggtggcag   7740
agccagctgg gaggcctgca aggccaggac ctgagccagg tggaacggga tgcaagcagt   7800
tcagtgtcca ccctggagaa gacattgcca cagctgctgg ccaaactgag ccgtctagag   7860
aaccgtggag ttcacaatgc cagcctggct ttgtctgcca cattggtcg  tgtgcgcaag   7920
ctcattgccc aagcccggag tgccgccagc aaggtcaagg tgtccatgaa gttcaatggg   7980
cgttcagggg tacgactgcg tcccccacga gaccttgccg accttgctgc gtacactgcc   8040
ctcaagttcc acatccagag cccagtgcca gcgcccgaac ctggcaagaa cacgggggac   8100
cactttgttc tgtacatggg cagccgccag gccactgggg actacatggg agtgtctctg   8160
cgtaatcaga aggtgcactg ggtgtacagg ctaggaaagg ctggccccac aactctcagc   8220
```

```
atcgacgaga acatcgggga gcagtttgca gccgtcagca tcgacaggac cctccagttt   8280
ggccacatgt ctgtcaccgt ggagaaacag atggttcatg agatcaaggg agacacggtg   8340
gcccctggga gcgagggact actcaacctg catcctgacg attttgtctt ctacgtggga   8400
ggatacccca gcaacttcac gcccctgaa ccctccgat tccctggcta cctgggctgc   8460
attgagatgg aaacactgaa tgaggaggtg gtcagcctct acaattttga gcagaccttc   8520
atgctggaca cggcagtaga taaaccttgt gctcgctcca aggccaccgg tgacccatgg   8580
ctcacagatg gctcctacct ggatggcagt ggctttgccc gcatcagctt tgagaagcag   8640
ttcagcaaca caaaacgctt tgaccaggag ctgcggcttg tgtcctacaa tgggatcatc   8700
tttttcctca gcaagagag ccagttcttg tgcctggcag tgcaggaagg caccctggtg   8760
ctcttctatg acttcggctc tggcctgaag aaggccgacc cactgcagcc cccacaagcc   8820
ttgacggcag ccagcaaggc gatccaagtg tttctattgg ctggcaatcg caaacgtgtg   8880
ttggtgcgtg tggagcgggc cactgtgttc agcgtagacc aggataacat gctggagatg   8940
gctgatgcct actacttggg aggdgtgcca cctgaacagc tgcccttgag cctacggcag   9000 ctcttccccct ccggaggctc tgtccgtggy tgcatcaagg gtattaaggc tctgggcaag   9060
tacgtggacc tcaaacggtt gaacaccacg ggcatcagtt tcggctgcac cgctgacctg   9120
ctagtgggac gcaccatgac ttttcacggc cacggcttcc tgcccctggc acttcctgat   9180
gtggcaccca tcaccgaagt ggtctattct ggctttggct ttcgtggcac ccaggacaac   9240
aacctgctgt attaccgtac ctccccggat gggccgtacc aggtatccct gagggagggc   9300
cacgtgacac tccgttttat gaaccaagag gtggaaactc aaagggtctt tgctgatggt   9360
gctcctcact atgttgcctt ctatagcaat gtcacagggg tatggctgta tgtggatgac   9420
cagctacaac tagtaaagtc tcatgagaga acaactccca tgctccaact acagcccgag   9480
gaaccctcac ggcttctcct gggaggcctg cctgtgtctg gtaccttcca caacttcagt   9540
ggctgcatca gcaatgtttt tgtacagcga cttcggggac cacagcgtgt gtttgaccta   9600
caccagaaca tggggagtgt caatgtaagc gtaggctgta caccagccca actcatcgag   9660
acctcaaggg ccacggctca gaaggtttcc cgccgtagtc gacaacccag ccaggacctt   9720
gcctgcacga caccctggct ccctgggact attcaggatg cataccagtt tggggggaccc   9780 ctgcccagtt acctacagtt tgtgggtatc tctccgtccc acaggaatag gctccacctc   9840
tccatgcttg tccgtccaca tgcggcttcc cagggcctcc tgctctctac agccccccatg   9900 tcgggccgca gcccttcgtt ggtactcttt ctaaaccatg gacactttgt cgcacagact   9960
gagggccctg ggccccggct ccaggtccag agtcgccagc actcacgggc tggccagtgg  10020
cacagggtgt ccgtccgctg gggaatgcag cagatccagc ttgtggtgga cggcagccag  10080
acctggagcc agaaggctct ccaccatcgg gtccccaggg cagagcgacc acagccctac  10140
accctctctg taggaggtct tcctgccagc agttacagtt ccaagctccc tgtgtctgtg  10200
gggttcagcg gctgtctgaa gaaattacag ctggataagc agccactgag gaccccaacg  10260
caaatggtgg gggtcacacc ctgtgtctca ggcccctgg aagatggcct gttcttccca  10320
ggcagtgagg gagttgtcac attagagctc cccaaggcca agatgcccta tgtgagcctg  10380
gagctagaga tgcggccctt ggcagctgct ggcctcatct tccacctggg ccaggccctg  10440
gccactccct acatgcagct gaaggtgctg acagaacagg tcctgctgca ggcaaatgat  10500
ggggcagggg agttttccac gtgggtgacc taccccaagc tttgtgatgg acggtggcac  10560
cgagtggcag tgatcatggg cagggacaca ctccggctgg aggtagacac acagagcaac  10620
```

| | |
|---|---|
| cacaccacag gccgtttgcc agagagcttg gctggttctc cagcacttct gcacctcggg | 10680 |
| agcctgccca agtcttcaac tgctcggcca gagctccctg cctaccgagg atgcttgagg | 10740 |
| aagctgctga tcaatggggc ccctgtcaac gtgactgctt ctgtacaaat ccaggggggca | 10800 |
| gtggggatgc gcggatgccc ctcaggaacc ctagcacttt ccaagcaggg aaaggcactg | 10860 |
| acccagaggc acgccaagcc cagtgtctcc ccgctacttt ggcattgagg gttcccagac | 10920 |
| cttggggttt gcctacactt tctatgaata acaagtcatt tctggtttac actgtcttt | 10980 |
| agaggaaaag gactctgtag aacagatat | 11009 |

<210> SEQ ID NO 40
<211> LENGTH: 2468
<212> TYPE: DNA
<213> ORGANISM: Mus musculus

<400> SEQUENCE: 40

| | |
|---|---|
| caggctgagc tcatggcttc cccctgagg ttcgacgggc gtgtggtctt ggtcaccggc | 60 |
| cccgggggag gattgggccg agcttacgcc ctggcgtttg cagaaagagg agcattagtc | 120 |
| attgtgaacg acttaggagg ggacttcaag ggaattggta aaggctcctc tgctgcagac | 180 |
| aaggttgtgg cagagataag aaggaaaggc ggaaaagcag tggccaatta cgattcagtt | 240 |
| gaagcaggcg agaagcttgt gaagacggca ctggacacat tggcagaat agacgttgtg | 300 |
| gtcaacaatg ctggaatcct gagggaccgt tccttctcca ggataagtga tgaagactgg | 360 |
| gatataattc atagagttca tttgcggggc tccttccaag tgacccgggc agcatgggac | 420 |
| catatgaaga aacagaatta tggaagaatc cttatgactt cctcagcttc tggaatatat | 480 |
| ggcaactttg gccaggcgaa ttatagtgct gcaaagctgg gcattctggg tctctgcaat | 540 |
| actctcgcca ttgaaggcag gaagaacaac attcattgca acaccattgc ccccaacgct | 600 |
| gggtcacgga tgacggagac tgtgttgccg gaagatcttg ttgaagccct gaagccagag | 660 |
| tatgtggccc ctctggtgct ttggctttgc catgagagct gtgaggaaaa tggtggccta | 720 |
| tttgaggttg gagcaggatg gattggaaaa ttgcgctggg agaggaccct gggcgccatc | 780 |
| gtcagaaagc ggaatcagcc catgactccc gaggcagtga gggacaactg ggagaagatc | 840 |
| tgtgacttca gcaatgccag caagccgcag accattcaag aatcaacagg tggtatagtc | 900 |
| gaagttttac ataaggtaga ttcagaagga atctcaccaa accgtaccag tcacgcggca | 960 |
| cctgcagcca cgtcaggatt cgttggtgct gttggccata aacttccttc atttttcttct | 1020 |
| tcgtatacgg agctgcagag tattatgtat gccctcggag tgggagcgtc agtcaaaaat | 1080 |
| ccaaaggatt tgaagtttgt ttatgaaggc agtgctgact tctcctgttt gcccaccttc | 1140 |
| ggagtcattg tcgctcagaa gtccatgatg aatggagggc tggcagaggt tcctgggctg | 1200 |
| tcattcaact ttgcaaaggc tcttcacggg gagcagtact tggagctgta taagccactt | 1260 |
| cttcgatcag gagaattaaa atgtgaagca gttattgctg acatcctgga taaaggctct | 1320 |
| ggcgtagtga ttgttatgga cgtctattct tattctggga aggaacttat atgctataat | 1380 |
| cagttctctg tctttgttgt tggctctggg ggctttggtg gaaaacggac atcagaaaaa | 1440 |
| ctcaaagcag ctgtagctgt accaaatcga cctccagatg ctgtactgag agatgccacc | 1500 |
| tcactgaatc aggccgcgct gtaccgcctc agcggagact ggaatcctct acacattgac | 1560 |
| ccggactttg cgagcgttgc cggttttgag aagcccatat tacatggact atgtaccttt | 1620 |
| ggattttctg caaggcatgt tttacagcag tttgcagata atgatgtatc aagattcaag | 1680 |
| gcgattaagg ttcgttttgc caaaccagtg tatccaggac agactctaca aactgagatg | 1740 |

```
tggaaggaag gaaacagaat tcattttcaa accaaggtcc acgagactgg agatgttgtc    1800
atttcaaatg cgtacgtgga tctcgtgcct gcatctggag tttcaaccca gacaccttca    1860
gagggtggag agctccagag tgctcttgtg tttggggaga taggccgccg cctcaagagt    1920
gttggccgtg aggtggtaaa gaaagcgaat gctgtgtttg aatggcatat cacgaaaggt    1980
gggactgttg cagccaagtg gaccattgac ctgaagagcg gctcagggga ggtgtaccaa    2040
ggccccgcaa agggctctgc tgatgtgacc atcatcattt ccgatgagga ttttatggaa    2100
gtggtcttcg gcaagcttga cccacagaag gccttcttca gtggcaggct gaaggccaga    2160
gggaacatca tgctgagcca gaaactacag atgattctta aagactatgc caagctctga    2220
agggaaccca ctgtgtgctg ttaaaggagt caataattaa atactgtcta cccagctgag    2280
ccgcagcctt ctgcgatcca caggagtgtg caggagaaat cgcttcacat ttccagattc    2340
agataacttg catattttca ttttctacta attttttcaca tattttttaca aggaactgta    2400 atctaggtag caaaataatc attctgttca tagatctgta tcttaataaa aaaaatcaac    2460
caaaaacc                                                             2468

<210> SEQ ID NO 41
<211> LENGTH: 60
<212> TYPE: DNA
<213> ORGANISM: Mus musculus

<400> SEQUENCE: 41
gcgtgccatg attctttcat ccaaacttcc cagaagcgaa tctaatcctc ttagttccat      60

<210> SEQ ID NO 42
<211> LENGTH: 60
<212> TYPE: DNA
<213> ORGANISM: Mus musculus

<400> SEQUENCE: 42
tgtcatatca ctgggtagac aggtacccat taccttagca agtatgttta gtgctcagtg      60

<210> SEQ ID NO 43
<211> LENGTH: 60
<212> TYPE: DNA
<213> ORGANISM: Mus musculus

<400> SEQUENCE: 43
cagttgtagt cacttgatac tgcattccga acttgagtct attgaatcca gaatgtgaat      60

<210> SEQ ID NO 44
<211> LENGTH: 60
<212> TYPE: DNA
<213> ORGANISM: Mus musculus

<400> SEQUENCE: 44
gactgcagcc ttggagcaaa acttaggttt tcatatgttt ttaaatatgt tgcttttgtg      60

<210> SEQ ID NO 45
<211> LENGTH: 60
<212> TYPE: DNA
<213> ORGANISM: Mus musculus

<400> SEQUENCE: 45
atgcacagaa taagttctcc aacatttatt attggtcagt tgatgttgct tagtgtcccc      60

<210> SEQ ID NO 46
<211> LENGTH: 60
```

```
<212> TYPE: DNA
<213> ORGANISM: Mus musculus

<400> SEQUENCE: 46
aacacagcct attttcgtga acattgaagt ttgtaacgga agataggat ctcattttca      60

<210> SEQ ID NO 47
<211> LENGTH: 60
<212> TYPE: DNA
<213> ORGANISM: Mus musculus

<400> SEQUENCE: 47
aggctacttc cttctcctca cctacatgta ttccctgctt cttagaattg tagctcattg     60

<210> SEQ ID NO 48
<211> LENGTH: 60
<212> TYPE: DNA
<213> ORGANISM: Mus musculus

<400> SEQUENCE: 48
gtaattgaac caagtcttta ctgaatgcct ggaaaatgaa agcttaatca acttaccctg     60

<210> SEQ ID NO 49
<211> LENGTH: 60
<212> TYPE: DNA
<213> ORGANISM: Mus musculus

<400> SEQUENCE: 49
ttccgttgtg gtcatcgtgt gcggtggcaa caacattagt agccaacagc ttcaggagct     60

<210> SEQ ID NO 50
<211> LENGTH: 60
<212> TYPE: DNA
<213> ORGANISM: Mus musculus

<400> SEQUENCE: 50
agcagtagct cagtcctggg acagaagacg aggcctggat gtgaagattc ctgaggccaa     60

<210> SEQ ID NO 51
<211> LENGTH: 60
<212> TYPE: DNA
<213> ORGANISM: Mus musculus

<400> SEQUENCE: 51
atgattgaac ccttcttggg gacctggaaa ctggtctcca gtgaaaactt cgagaattac     60

<210> SEQ ID NO 52
<211> LENGTH: 60
<212> TYPE: DNA
<213> ORGANISM: Mus musculus

<400> SEQUENCE: 52
aagaaaccga agacagcgac cgagtgtgcg tcaaagccgg taccacacaa gattccgcag     60

<210> SEQ ID NO 53
<211> LENGTH: 60
<212> TYPE: DNA
<213> ORGANISM: Mus musculus

<400> SEQUENCE: 53
gcagcatgtt acagcagaaa agaaactaca gcacaactta tgactgaaaa taatgtagaa     60

<210> SEQ ID NO 54
<211> LENGTH: 60
```

```
<212> TYPE: DNA
<213> ORGANISM: Mus musculus

<400> SEQUENCE: 54
gtgacgcttg gccttaggtg tcattgttaa acaacataaa acttctcatt tatgagtaaa    60

<210> SEQ ID NO 55
<211> LENGTH: 60
<212> TYPE: DNA
<213> ORGANISM: Mus musculus

<400> SEQUENCE: 55
gagactaatt tcacatctta ttttgcagtc atttacagtg aaacaatgtt ccagctagct    60

<210> SEQ ID NO 56
<211> LENGTH: 60
<212> TYPE: DNA
<213> ORGANISM: Mus musculus

<400> SEQUENCE: 56
gtatgattca cgcaacaata ctcttatctt agtaagtcct acttcttatg tgctgatgcc    60

<210> SEQ ID NO 57
<211> LENGTH: 60
<212> TYPE: DNA
<213> ORGANISM: Mus musculus

<400> SEQUENCE: 57
agtaacccaa aagaacaaaa aattccccat ctgtactctt tcgggctcat accttcttct    60

<210> SEQ ID NO 58
<211> LENGTH: 60
<212> TYPE: DNA
<213> ORGANISM: Mus musculus

<400> SEQUENCE: 58 ggagggctc ctcgagagaa gattggaaca gtggcagtgt tataattagt aaggttttt    60

<210> SEQ ID NO 59
<211> LENGTH: 60
<212> TYPE: DNA
<213> ORGANISM: Mus musculus

<400> SEQUENCE: 59
acctgattcc ttcctgaggc tatagaaggt ttagctgcat taaacgagat gcttcagcag    60

<210> SEQ ID NO 60
<211> LENGTH: 60
<212> TYPE: DNA
<213> ORGANISM: Mus musculus

<400> SEQUENCE: 60
ctcgactgaa tacagaaatg gcttttcttc ttatccacga tcattctgta ttttgaagtt    60

<210> SEQ ID NO 61
<211> LENGTH: 60
<212> TYPE: DNA
<213> ORGANISM: Mus musculus

<400> SEQUENCE: 61
gtcgctttac attgcttcct agttttacag catgatgcaa atgaatttc taacttagtg     60

<210> SEQ ID NO 62
<211> LENGTH: 60
```

```
<212> TYPE: DNA
<213> ORGANISM: Mus musculus

<400> SEQUENCE: 62
ctattcctct gttctttcag atagtaatgg gagcttttac tggcttacat cattacaata    60

<210> SEQ ID NO 63
<211> LENGTH: 60
<212> TYPE: DNA
<213> ORGANISM: Mus musculus

<400> SEQUENCE: 63
gcagaactgc ttggttgtct tttcccatgt aacttaagca tagtaatata aataaagtgg    60

<210> SEQ ID NO 64
<211> LENGTH: 60
<212> TYPE: DNA
<213> ORGANISM: Mus musculus

<400> SEQUENCE: 64
cctttctcac ctggaagaca gctcctcctc gaaggtttac aaaatgtgtg atgcctttgt    60

<210> SEQ ID NO 65
<211> LENGTH: 60
<212> TYPE: DNA
<213> ORGANISM: Mus musculus

<400> SEQUENCE: 65
atgtcagatg ttgtaaaacc cagagtatgg cagtgtcttt aatgaggctg ggctcttgtc    60

<210> SEQ ID NO 66
<211> LENGTH: 60
<212> TYPE: DNA
<213> ORGANISM: Mus musculus

<400> SEQUENCE: 66
cctttgtggg aacctggaag cttgtctcca gtgaaaactt cgatgattac atgaaagaag    60

<210> SEQ ID NO 67
<211> LENGTH: 60
<212> TYPE: DNA
<213> ORGANISM: Mus musculus

<400> SEQUENCE: 67
gcttctgcta gatgaaaatt cactgaaaat tcagtcagtc acaaactgga agaattgtaa    60

<210> SEQ ID NO 68
<211> LENGTH: 60
<212> TYPE: DNA
<213> ORGANISM: Mus musculus

<400> SEQUENCE: 68
gtggacgaca tacggaaaag ctaatggcat ttaaagcaat atacccagac attgtgcgac    60

<210> SEQ ID NO 69
<211> LENGTH: 60
<212> TYPE: DNA
<213> ORGANISM: Mus musculus

<400> SEQUENCE: 69
atatattaag tctctccctc tctggagttc ttggctacag caaggccaga tatcacattg    60

<210> SEQ ID NO 70
<211> LENGTH: 60
```

<212> TYPE: DNA
<213> ORGANISM: Mus musculus

<400> SEQUENCE: 70
actttctggg cagagtgaat aaccccaga gtgtggtgtg aggccttgtg cctagcccat    60

<210> SEQ ID NO 71
<211> LENGTH: 60
<212> TYPE: DNA
<213> ORGANISM: Mus musculus

<400> SEQUENCE: 71
aagatgcttt gaaggacaca acaagaaatt ctttaaagct gtggaagaaa tctagacgtg    60

<210> SEQ ID NO 72
<211> LENGTH: 60
<212> TYPE: DNA
<213> ORGANISM: Mus musculus

<400> SEQUENCE: 72
tgggtgtgaa ccacacatct gtctatccaa tggactgggt agataatacc taagaacagc    60

<210> SEQ ID NO 73
<211> LENGTH: 60
<212> TYPE: DNA
<213> ORGANISM: Mus musculus

<400> SEQUENCE: 73
ttgagagctg ggcttcctgc ctcttacata caataaagag attgctaaca ctggaaaaaa    60

<210> SEQ ID NO 74
<211> LENGTH: 60
<212> TYPE: DNA
<213> ORGANISM: Mus musculus

<400> SEQUENCE: 74
tcagaacaac agtgtttagc aagtggcatc tgacaggtgt gaatattttc ctacaatgtg    60

<210> SEQ ID NO 75
<211> LENGTH: 60
<212> TYPE: DNA
<213> ORGANISM: Mus musculus

<400> SEQUENCE: 75
ccctgtatga gtggagggat agtttaaagt tttcaccatg ttatattttc ttttgagact    60

<210> SEQ ID NO 76
<211> LENGTH: 60
<212> TYPE: DNA
<213> ORGANISM: Mus musculus

<400> SEQUENCE: 76
ctggcaaggt catgtgcctt ctctgatgcc aaaacccttt atggggtga tggagtactt    60

<210> SEQ ID NO 77
<211> LENGTH: 60
<212> TYPE: DNA
<213> ORGANISM: Mus musculus

<400> SEQUENCE: 77
tggtgaaaca caagaaaggg attgtcaacg agcagttcct gctgcagcga ctggcggacg    60

<210> SEQ ID NO 78
<211> LENGTH: 60

```
<212> TYPE: DNA
<213> ORGANISM: Mus musculus

<400> SEQUENCE: 78
tagctggtgc attgaggctg caactcggat ccgagaaaac atggccagtc tgcagtccag      60

<210> SEQ ID NO 79
<211> LENGTH: 60
<212> TYPE: DNA
<213> ORGANISM: Mus musculus

<400> SEQUENCE: 79
ctgcagagtt ggtaattcag aaaactcaag gtttaagtta aaagtgagtt tagactttgg      60

<210> SEQ ID NO 80
<211> LENGTH: 60
<212> TYPE: DNA
<213> ORGANISM: Mus musculus

<400> SEQUENCE: 80
ctgtcttgag aaacttcatt tatttctcat aactgcattt atttagccat ctcagtgtgc      60

<210> SEQ ID NO 81
<211> LENGTH: 60
<212> TYPE: DNA
<213> ORGANISM: Mus musculus

<400> SEQUENCE: 81
taaaagcatg cacattgaga gtatcctgga agacattctc ttgtaaacat gtgtgtggaa      60

<210> SEQ ID NO 82
<211> LENGTH: 60
<212> TYPE: DNA
<213> ORGANISM: Mus musculus

<400> SEQUENCE: 82
gattcaatgc ctgggctttc aaactcattc cttcactcca caaatatttg ctgaatgttt      60

<210> SEQ ID NO 83
<211> LENGTH: 60
<212> TYPE: DNA
<213> ORGANISM: Mus musculus

<400> SEQUENCE: 83
cctacacttt ctatgaataa caagtcattt ctggtttaca ctgtctttta gaggaaaagg      60

<210> SEQ ID NO 84
<211> LENGTH: 60
<212> TYPE: DNA
<213> ORGANISM: Mus musculus

<400> SEQUENCE: 84
atcatcattt ccgatgagga ttttatggaa gtggtcttcg gcaagcttga cccacagaag      60

<210> SEQ ID NO 85
<211> LENGTH: 60
<212> TYPE: DNA
<213> ORGANISM: Mus musculus

<400> SEQUENCE: 85
tttcaaacca aggtccacga gactggagat gttgtcattt caaatgcgta cgtggatctc      60

<210> SEQ ID NO 86
<211> LENGTH: 60
```

```
<212> TYPE: DNA
<213> ORGANISM: Mus musculus

<400> SEQUENCE: 86
gcaggagaaa tcgcttcaca tttccagatt cagataactt gcatattttc attttctact      60
```

METHODS FOR CHARACTERIZING AGONISTS AND PARTIAL AGONISTS OF TARGET MOLECULES

CROSS-REFERENCE TO RELATED APPLICATION

This application claims the benefit of U.S. Provisional Application No. 60/668,773, filed Apr. 5, 2005, which is herein incorporated by reference.

FIELD OF THE INVENTION

The present invention relates to methods for screening biologically active agents, such as candidate drug molecules, to identify agents that possess a desired biological activity.

BACKGROUND OF THE INVENTION

Identifying new drug molecules for treating human diseases is a time consuming and expensive process. A candidate drug molecule is usually first identified in a laboratory using an assay for a desired biological activity. The candidate drug is then tested in animals to identify any adverse side effects that might be caused by the drug. This phase of preclinical research and testing may take more than five years. See, e.g., J. A. Zivin, "Understanding Clinical Trials," *Scientific American*, pp. 69-75 (April 2000). The candidate drug is then subjected to extensive clinical testing in humans to determine whether it continues to exhibit the desired biological activity, and whether it induces undesirable, perhaps fatal, side effects. This process may take up to a decade. Id. Adverse effects are often not identified until late in the clinical testing phase when considerable expense has been incurred testing the candidate drug.

For example, an agonist (also referred to as a full agonist) is a chemical substance that binds to a target molecule (e.g., a receptor molecule), in or on a cell, to produce a biochemical and/or physiological effect. A partial agonist is a chemical substance that binds to a target molecule, but does not produce as great a magnitude of a biochemical and/or physiological effect as the agonist. The maximum magnitude of the biochemical and/or physiological effect produced by an agonist of a target molecule cannot be produced by a partial agonist of the same target molecule, even by increasing the dosage of the partial agonist. Some agonists of a target molecule are medically useful drugs that typically produce both desirable and undesirable biological effects. In contrast, partial agonists of a target molecule, that are medically useful drugs, often produce a weaker undesirable biological response than does an agonist of the same target molecule. Thus, partial agonists may be better drugs than full agonists because a partial agonist causes a desirable biological effect, and causes little or no undesirable biological effects.

There is a need, therefore, for methods for identifying partial agonists of target molecules that possess a desirable biological activity, and which cause fewer, or less severe, adverse effects than an agonist of the same target molecules.

SUMMARY OF THE INVENTION

In accordance with the foregoing, in one aspect the present invention provides methods for determining whether an agent is more like a partial agonist of a target molecule than a full agonist of the same target molecule. The methods of the invention thereby facilitate identification of partial agonists that may be medically useful drugs having limited undesirable side effects compared to a full agonist of the same target molecule. As described more fully herein, the methods of this aspect of the invention compare the expression of populations of genes in response to an agent to determine whether the agent is more like a partial agonist of a target molecule than a full agonist of the same target molecule.

Accordingly, in one aspect, the present invention provides methods for determining whether an agent is more like a partial agonist of a target molecule than a full agonist of the same target molecule. The methods each include the steps of (a) comparing the magnitude of gene expression of a first population of genes, in a cell type, in response to an agent, to the magnitude of gene expression of the first population of genes, in the cell type, in response to a full agonist of a target molecule, to produce a first comparison result, wherein the first comparison result is represented by a first numerical value; (b) comparing the magnitude of gene expression of a second population of genes, in a cell type, in response to the agent to the magnitude of gene expression of the second population of genes, in the cell type, in response to the full agonist of the target molecule, to produce a second comparison result, wherein the second comparison result is represented by a second numerical value; and (c) using the first numerical value and the second numerical value to determine whether the agent is more like a partial agonist of the target molecule than the full agonist of the target molecule, wherein any part of step (a) can occur before, during, or after any part of step (b). The methods of this aspect of the invention are useful, for example, for determining whether an agent (e.g., chemical compound) induces a biological response in a living thing that is more like the biological response induced in the living thing by a partial agonist of a target molecule (e.g., a receptor, such as a PPARγ molecule described more fully herein) than the biological response induced in the living thing by a full agonist of the target molecule (e.g., PPARγ). The methods of this aspect of the present invention are dose-independent.

In another aspect, the present invention provides methods to screen compounds to identify a candidate compound that may reduce blood plasma glucose concentration in a mammal (e.g., a human being). The methods of this aspect of the invention each include the step of contacting a cell of a cell type with a compound and determining whether the compound causes a significant increase in the level of expression of a population of 29 genes that each hybridize under stringent conditions to a different member of the group of nucleic acid molecules consisting of SEQ ID NOS:1-29, wherein if the compound causes a significant increase in the level of expression of the population of 29 genes then the compound is selected as a candidate compound that may reduce blood plasma glucose concentration in a mammal. SEQ ID NOS:1-29 are cDNA molecules that correspond to 29 different genes as described herein. The methods of this aspect of the invention are useful, for example, for selecting partial agonists of PPARγ that reduce blood plasma glucose concentration in a mammal.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

THE FIGURE shows a graph of gene score 1 (GS1) versus gene score 2 (GS2) for several partial and full agonists of PPARγ, as described in Example 2.

DETAILED DESCRIPTION OF THE PREFERRED EMBODIMENT

Unless specifically defined herein, all terms used herein have the same meaning as they would to one skilled in the art of the present invention. Practitioners are particularly directed to Sambrook et al. (1989) *Molecular Cloning: A Laboratory Manual,* 2d ed., Cold Spring Harbor Press, Plainsview, N.Y. (1989), and Ausubel et al., *Current Protocols in Molecular Biology* (Supplement 47), John Wiley & Sons, New York (1999), for definitions and terms of the art.

In one aspect, the present invention provides methods for determining whether an agent is more like a partial agonist of a target molecule than a full agonist of the same target molecule. The methods of the present invention permit comparison of the magnitudes of expression levels of populations of genes in a living thing to determine whether an agent is more like a partial agonist of a target molecule than a full agonist of the same target molecule. The methods each include the steps of (a) comparing the magnitude of gene expression of a first population of genes, in cells of a cell type, in response to an agent to the magnitude of gene expression of the first population of genes, in cells of the cell type, in response to a full agonist of a target molecule, to produce a first comparison result, wherein the first comparison result is represented by a first numerical value; (b) comparing the magnitude of gene expression of a second population of genes, in cells of the cell type, in response to the agent to the magnitude of gene expression of the second population of genes, in cells of the cell type, in response to the full agonist of the target molecule, to produce a second comparison result, wherein the second comparison result is represented by a second numerical value; and (c) using the first numerical value and the second numerical value to determine whether the agent is more like a partial agonist of the target molecule than the full agonist of the target molecule, wherein any part of step (a) can occur before, during, or after any part of step (b).

The methods of this aspect of the present invention are dose-independent (i.e., in the practice of the methods it is not necessary to use the same dose, or a comparable dose based on $EC_{50}$, of the agent and the full agonist of the target molecule in order to determine whether the agent is more like a partial agonist of the target molecule than the full agonist of the same target molecule). Thus, for example, the methods of the present invention are particularly useful for high-throughput screening of numerous candidate drug molecules because it is not necessary to determine the $EC_{50}$ of each test compound, and to match the dosage of each test compound to the dosage of the reference compound(s) so that comparable $EC_{50}$s of the candidate and reference compounds are used. An additional advantage of the methods of this aspect of the present invention is that it is not necessary to identify compound-specific signature genes, or proteins, to practice the methods of this aspect of the present invention.

As used herein, the term "agent" encompasses any physical, chemical, or energetic agent that induces a biological response in a living organism in vivo and/or in vitro. Thus, for example, the term "agent" encompasses chemical molecules, such as therapeutic molecules, or candidate therapeutic molecules, that may be useful for treating one or more diseases in a living organism, such as in a mammal (e.g., a human being). The term "agent" also encompasses energetic stimuli, such as ultraviolet light. The term "agent" also encompasses physical stimuli, such as forces applied to living cells (e.g., pressure, stretching or shear forces).

For example, the methods of the present invention can be used to determine whether an agent is more like a full agonist or a partial agonist of a target molecule (e.g., a receptor molecule). A full agonist is a chemical substance that binds to a target molecule, in or on a cell, to produce a biochemical and/or physiological effect. A partial agonist also binds to a target molecule, but does not produce as great a magnitude of a biochemical or physiological effect as the full agonist. The maximum magnitude of the biochemical and/or physiological effect produced by a full agonist of a target molecule cannot be produced by a partial agonist of the same target molecule, even by increasing the dosage of the partial agonist.

An example of a receptor molecule is the peroxisome proliferator-activated receptor gamma (hereinafter referred to as PPARγ). A family of structurally and functionally related PPARγs exists in mammals. PPARγs are nuclear hormone receptors, activated by fatty acids, and their eicosanoid metabolites, and by some synthetic compounds, such as the thiazolidinedione (abbreviated as TZD) class of compounds. PPARγs play an important physiological role in metabolism, maintenance of cellular energy homeostasis, and cellular differentiation. Two members of the TZD class of compounds (rosiglitazone and pioglitazone) are PPARγ agonists that reduce hyperglycemia in type 2 diabetes patients. See, e.g., J. L. Oberfield et al., *Proc. Nat'l Acad. Sci. U.S.A.* 96:6102-6106 (1999). In spite of their significant antidiabetic activity, however, the use of TZDs has been limited by adverse side-effects, such as plasma volume expansion and weight gain. Thus, there is a need to identify other ligands that bind to PPARγs and that have desirable biological effects (e.g., reducing blood plasma glucose concentration) but that do not have significant adverse biological effects.

Contacting a living cell with an agent: In the practice of the present invention comparisons are made between populations of genes that are expressed in at least one living cell (typically in multiple living cells) of a cell type. For ease of description, the use of multiple living cells will be described, although it will be understood that the following description also applies to the use of a single living cell of a cell type. The living cells of the cell type are contacted with an agent before the comparisons are made between populations of genes that are expressed in the living cells.

The living cells can be any type of living cell (e.g., prokaryotic cell or eukaryotic cell, including animal cell and plant cell), although typically the living cells are mammalian cells. In order to be useful in the practice of the present invention, the living cells must include sufficient target molecules (e.g., PPARγ receptors) to provide a measurable response to an agonist, or partial agonist, of the target molecules. The living cells can be cultured in vitro, or can be living cells in vivo. Typically, numerous living cells (e.g., a population of cells cultured in vitro, or a multiplicity of living cells that exist within a living tissue, organ or organism) are contacted with an agent.

An example of a method for contacting living cells, cultured in vitro, with a chemical agent is addition of the agent to the medium in which the living cells are cultured. Examples of methods for contacting living cells, in vivo, with an agent is injection into the bloodstream, or injection into a target tissue or organ, or nasal administration of the agent, or transdermal administration of the agent, or use of a drug delivery device that is implanted into the body of a living subject and which gradually releases the agent into the living body.

First Population of Genes and Second Population of Genes: the present invention provides methods for determining whether an agent is more like a partial agonist of a target molecule than a full agonist of the same target molecule. The methods of the present invention use a first population of genes. Each member of the first population of genes is selected from a population of regulated genes wherein each gene is regulated by a partial agonist of a target molecule, and also by a full agonist of the same target molecule. The population of regulated genes only includes genes that are regulated in the same direction by the partial agonist and by the full agonist (i.e., only genes that are either upregulated by both the full and partial agonist, or genes that are downregulated by both the full and partial agonist are present in the population of regulated genes).

With respect to each member of the first population of genes, the ratio of the magnitude of regulation of the gene by a partial agonist of a target molecule to the magnitude of regulation of the gene by a full agonist of the same target molecule is consistently greater than the same ratio (magnitude of regulation by the partial agonist/magnitude of regulation by the full agonist) for any of the regulated genes that are not included in the first population of genes.

An example of a first population of genes is an efficacy-related population of genes. As used herein, the phrase "efficacy-related population of genes" refers to a population of genes, present in a living thing, that yields at least one expression pattern, in response to a full agonist of a target molecule, and in response to a partial agonist of the target molecule, that correlates (positively or negatively) with the presence of at least one desired biological response caused by the full or partial agonist in the living thing. By way of example, SEQ ID NOS:1-29 are cDNA molecules that correspond to a population of 29 different efficacy-related genes as described herein. It will be understood that SEQ ID NOS: 1-29 are cDNA sequences, and that the expression of the corresponding gene transcripts (e.g., mRNA molecules) are analyzed in the practice of the present invention.

The methods of the present invention also use a second population of genes. Each member of the second population of genes is selected from a population of regulated genes wherein each gene is regulated by a partial agonist of a target molecule, and also by a full agonist of the same target molecule. The population of regulated genes only includes genes that are regulated in the same direction by the partial agonist and by the full agonist (i.e., only genes that are either upregulated by both the full and partial agonist, or genes that are downregulated by both the full and partial agonist are present in the population of regulated genes).

With respect to each member of the second population of genes, the ratio of the magnitude of regulation of the gene by a partial agonist of a target molecule to the magnitude of regulation of the gene by a full agonist of the same target molecule is consistently lower than the same ratio (magnitude of regulation by the partial agonist/magnitude of regulation by the full agonist) for any of the regulated genes that are not included in the second population of genes.

An example of a second population of genes is a toxicity-related population of genes. As used herein, the phrase "toxicity-related population of genes" refers to a population of genes, present in a living thing, that yields at least one expression pattern, in response to a full agonist of a target molecule, and in response to a partial agonist of the target molecule, that correlates (positively or negatively) with the presence of at least one undesirable biological response caused by the full or partial agonist in the living thing. By way of example, SEQ ID NOS:30-40 are cDNA molecules that correspond to a population of 11 different toxicity-related genes as described herein. It will be understood that SEQ ID NOS:30-40 are cDNA sequences, and that the expression of the corresponding gene transcripts (e.g., mRNA molecules) is analyzed in the practice of the present invention.

The magnitude and/or pattern of expression of a first population of genes and/or second population of genes can be measured, for example, by measuring the magnitude and/or pattern of expression of gene transcripts (e.g., mRNA that is present in total RNA extracted from a living thing, or completely or partially purified mRNA extracted from a living thing), or by measuring the magnitude and/or pattern of expression of proteins encoded by the genes.

Useful first and second populations of genes can be identified by any method, or combination of methods, that permits detection and measurement of the expression of a population of genes (e.g., protein microarrays and/or nucleic acid microarrays). EXAMPLE 1 herein describes a representative procedure for identifying the efficacy-related population of genes that corresponds to SEQ ID NOS:1-29, and for identifying the toxicity-related population of genes that corresponds to SEQ ID NOS:30-40.

Detecting Gene Expression by Measuring Gene Transcript Expression: In the practice of the present invention, the magnitude of gene expression of a first population of genes, and the magnitude of gene expression of a second population of genes are measured in cells of a cell type that have been contacted with an agent.

Gene expression may be measured, for example, by extracting (and optionally purifying) mRNA from the living thing, and using the mRNA as a template to synthesize cDNA which is then labeled (e.g., with a fluorescent dye) and can be used to measure gene expression. While the following, exemplary, description is directed to embodiments of the invention in which the extracted mRNA is used as a template to synthesize cDNA, which is then labeled, it will be understood that the extracted mRNA can also be used as a template to synthesize cRNA which can then be labeled and can be used to measure gene expression.

RNA molecules useful as templates for cDNA synthesis can be isolated from any organism or part thereof, including organs, tissues, and/or individual cells. Any suitable RNA preparation can be utilized, such as total cellular RNA, or such as cytoplasmic RNA or such as an RNA preparation that is enriched for messenger RNA (mRNA), such as RNA preparations that include greater than 70%, or greater than 80%, or greater than 90%, or greater than 95%, or greater than 99% messenger RNA. Typically, RNA preparations that are enriched for messenger RNA are utilized to provide the RNA template in the practice of the methods of this aspect of the invention. Messenger RNA can be purified in accordance with any art-recognized method, such as by the use of oligo-dT columns (see, e.g., Sambrook et al., 1989, *Molecular Cloning—A Laboratory Manual* (2nd Ed.), Vol. 1, Chapter 7, Cold Spring Harbor Laboratory, Cold Spring Harbor, N.Y.).

Total RNA may be isolated from cells by procedures that involve breaking open the cells and, typically, denaturation of the proteins contained therein. Additional steps may be employed to remove DNA. Cell lysis may be accomplished with a nonionic detergent, followed by microcentrifugation to remove the nuclei and hence the bulk of the cellular DNA. In one embodiment, RNA is extracted from cells using guanidinium thiocyanate lysis followed by CsCl centrifugation to separate the RNA from DNA (Chirgwin et al., 1979, *Biochemistry* 18:5294-5299). Messenger RNA may be selected with oligo-dT cellulose (see Sambrook et al., supra). Separation of RNA from DNA can also be accomplished by organic extraction, for example, with hot phenol or phenol/chloroform/isoamyl alcohol. If desired, RNase inhibitors may be added to the lysis buffer. Likewise, for certain cell types, it may be desirable to add a protein denaturation/digestion step to the protocol.

The sample of total RNA typically includes a multiplicity of different mRNA molecules, each different mRNA molecule having a different nucleotide sequence (although there may be multiple copies of the same mRNA molecule). In a specific embodiment, the mRNA molecules in the RNA sample comprise at least 100 different nucleotide sequences. In other embodiments, the mRNA molecules of the RNA sample comprise at least 500, 1,000, 5,000, 10,000, 20,000, 30,000, 40,000, 50,000, 60,000, 70,000, 80,000, 90,000 or 100,000 different nucleotide sequences. In another specific embodiment, the RNA sample is a mammalian RNA sample, the mRNA molecules of the mammalian RNA sample comprising about 20,000 to 30,000 different nucleotide sequences, or comprising substantially all of the different mRNA sequences that are expressed in the cell(s) from which the mRNA was extracted.

In the context of the present example, cDNA molecules are synthesized that are complementary to the RNA template molecules. Each cDNA molecule is preferably sufficiently long (e.g., at least 50 nucleotides in length) to subsequently serve as a specific probe for the mRNA template from which it was synthesized, or to serve as a specific probe for a DNA sequence that is identical to the sequence of the mRNA template from which the cDNA molecule was synthesized. Individual DNA molecules can be complementary to a whole RNA template molecule, or to a portion thereof. Thus, a population of cDNA molecules is synthesized that includes individual DNA molecules that are each complementary to all, or to a portion, of a template RNA molecule. Typically, at least a portion of the complementary sequence of at least 95% (more typically at least 99%) of the template RNA molecules are represented in the population of cDNA molecules.

Any reverse transcriptase molecule can be utilized to synthesize the cDNA molecules, such as reverse transcriptase molecules derived from Moloney murine leukemia virus (MMLV-RT), avian myeloblastosis virus (AMV-RT), bovine leukemia virus (BLV-RT), Rous sarcoma virus (RSV) and human immunodeficiency virus (HIV-RT). A reverse transcriptase lacking RNaseH activity (e.g., SUPERSCRIPT II™ sold by Stratagene, La Jolla, Calif.) has the advantage that, in the absence of an RNaseH activity, synthesis of second strand cDNA molecules does not occur during synthesis of first strand cDNA molecules. The reverse transcriptase molecule should also preferably be thermostable so that the cDNA synthesis reaction can be conducted at as high a temperature as possible, while still permitting hybridization of any required primer(s) to the RNA template molecules.

The synthesis of the cDNA molecules can be primed using any suitable primer, typically an oligonucleotide in the range of ten to 60 bases in length. Oligonucleotides that are useful for priming the synthesis of the cDNA molecules can hybridize to any portion of the RNA template molecules, including the oligo-dT tail. In some embodiments, the synthesis of the cDNA molecules is primed using a mixture of primers, such as a mixture of primers having random nucleotide sequences. Typically, for oligonucleotide molecules less than 100 bases in length, hybridization conditions are 5° C. to 10° C. below the homoduplex melting temperature (Tm); see generally, Sambrook et al. *Molecular Cloning: A Laboratory Manual*, 2nd ed., Cold Spring Harbor Press, 1987; Ausubel et al., *Current Protocols in Molecular Biology*, Greene Publishing, 1987).

A primer for priming cDNA synthesis can be prepared by any suitable method, such as phosphotriester and phosphodiester methods of synthesis, or automated embodiments thereof. It is also possible to use a primer that has been isolated from a biological source, such as a restriction endonuclease digest. An oligonucleotide primer can be DNA, RNA, chimeric mixtures or derivatives or modified versions thereof, so long as it is still capable of priming the desired reaction. The oligonucleotide primer can be modified at the base moiety, sugar moiety, or phosphate backbone, and may include other appending groups or labels, so long as it is still capable of priming cDNA synthesis.

An oligonucleotide primer for priming cDNA synthesis can be derived by cleavage of a larger nucleic acid fragment using non-specific nucleic acid cleaving chemicals or enzymes or site-specific restriction endonucleases; or by synthesis by standard methods known in the art, e.g., by use of an automated DNA synthesizer (such as are commercially available from Biosearch, Applied Biosystems, etc.) and standard phosphoramidite chemistry. As examples, phosphorothioate oligonucleotides may be synthesized by the method of Stein et al. (*Nucl. Acids Res.* 16:3209-3221, 1988), methylphosphonate oligonucleotides can be prepared by use of controlled pore glass polymer supports (Sarin et al., 1988, *Proc. Natl. Acad. Sci. U.S.A.* 85:7448-7451).

Once the desired oligonucleotide is synthesized, it is cleaved from the solid support on which it was synthesized and treated, by methods known in the art, to remove any protecting groups present. The oligonucleotide may then be purified by any method known in the art, including extraction and gel purification. The concentration and purity of the oligonucleotide may be determined, for example, by examining the oligonucleotide that has been separated on an acrylamide gel, or by measuring the optical density at 260 nm in a spectrophotometer.

After cDNA synthesis is complete, the RNA template molecules can be hydrolyzed, and all, or substantially all (typically more than 99%), of the primers can be removed. Hydrolysis of the RNA template can be achieved, for example, by alkalinization of the solution containing the RNA template (e.g., by addition of an aliquot of a concentrated sodium hydroxide solution). The primers can be removed, for example, by applying the solution containing the RNA template molecules, cDNA molecules, and the primers, to a column that separates nucleic acid molecules on the basis of size. The purified, cDNA molecules, can then, for example, be precipitated and redissolved in a suitable buffer.

The cDNA molecules are typically labeled to facilitate the detection of the cDNA molecules when they are used as a probe in a hybridization experiment, such as a probe used to screen a DNA microarray, to identify an efficacy-related population of genes. The cDNA molecules can be labeled with any useful label, such as a radioactive atom (e.g., $^{32}P$), but typically the cDNA molecules are labeled with a dye. Examples of suitable dyes include fluorophores and chemiluminescers.

By way of example, cDNA molecules can be coupled to dye molecules via aminoallyl linkages by incorporating allylamine-derivatized nucleotides (e.g., allylamine-dATP, allylamine-dCTP, allylamine-dGTP, and/or allylamine-dTTP) into the cDNA molecules during synthesis of the cDNA molecules. The allylamine-derivatized nucleotide(s) can then be coupled, via an aminoallyl linkage, to N-hydroxysuccinimide ester derivatives (NHS derivatives) of dyes (e.g., Cy-NHS, Cy3-NHS and/or Cy5-NHS). Again by way of example, in another embodiment, dye-labeled nucleotides may be incorporated into the cDNA molecules during synthesis of the cDNA molecules, which labels the cDNA molecules directly.

It is also possible to include a spacer (usually 5-16 carbon atoms long) between the dye and the nucleotide, which may improve enzymatic incorporation of the modified nucleotides during synthesis of the cDNA molecules.

In the context of the present example, the labeled cDNA is hybridized to a DNA array that includes hundreds, or thousands, of identified nucleic acid molecules (e.g., cDNA molecules) that correspond to genes that are expressed in the type of cells wherein gene expression is being analyzed. Typically, hybridization conditions used to hybridize the labeled cDNA to a DNA array are no more than 25° C. to 30° C. (for example, 10° C.) below the melting temperature (Tm) of the native duplex of the cDNA that has the lowest melting temperature (see generally, Sambrook et al. *Molecular Cloning: A Laboratory Manual,* 2nd ed., Cold Spring Harbor Press, 1987; Ausubel et al., *Current Protocols in Molecular Biology*, Greene Publishing, 1987). Tm for nucleic acid molecules greater than about 100 bases can be calculated by the formula Tm=81.5+0.41%(G+C)−log(Na+). For oligonucleotide molecules less than 100 bases in length, exemplary hybridization conditions are 5° to 10° C. below Tm.

Preparation of microarrays. Nucleic acid molecules can be immobilized on a solid substrate by any art-recognized means. For example, nucleic acid molecules (such as DNA or RNA molecules) can be immobilized to nitrocellulose, or to a synthetic membrane capable of binding nucleic acid molecules, or to a nucleic acid microarray, such as a DNA microarray. A DNA microarray, or chip, is a microscopic array of DNA fragments, such as synthetic oligonucleotides, disposed in a defined pattern on a solid support, wherein they are amenable to analysis by standard hybridization methods (see, Schena, *BioEssays* 18:427, 1996).

The DNA in a microarray may be derived, for example, from genomic or cDNA libraries, from fully sequenced clones, or from partially sequenced cDNAs known as expressed sequence tags (ESTs). Methods for obtaining such DNA molecules are generally known in the art (see, e.g., Ausubel et al. (eds.), 1994, *Current Protocols in Molecular Biology*, Vol. 2, Current Protocols Publishing, New York). Again by way of example, oligonucleotides may be synthesized by conventional methods, such as the methods described herein.

Microarrays can be made in a number of ways, of which several are described below. However produced, microarrays preferably share certain characteristics. The arrays are preferably reproducible, allowing multiple copies of a given array to be produced and easily compared with each other. Preferably the microarrays are small, usually smaller than 5 cm², and they are made from materials that are stable under nucleic acid hybridization conditions. A given binding site or unique set of binding sites in the microarray should specifically bind the product of a single gene (or a nucleic acid molecule that represents the product of a single gene, such as a cDNA molecule that is complementary to all, or to part, of an mRNA molecule). Although there may be more than one physical binding site (hereinafter "site") per specific gene product, for the sake of clarity the discussion below will assume that there is a single site.

In one embodiment, the microarray is an array of polynucleotide probes, the array comprising a support with at least one surface and typically at least 100 different polynucleotide probes, each different polynucleotide probe comprising a different nucleotide sequence and being attached to the surface of the support in a different location on the surface. For example, the nucleotide sequence of each of the different polynucleotide probes can be in the range of 40 to 80 nucleotides in length. For example, the nucleotide sequence of each of the different polynucleotide probes can be in the range of 50 to 70 nucleotides in length. For example, the nucleotide sequence of each of the different polynucleotide probes can be in the range of 50 to 60 nucleotides in length. In specific embodiments, the array comprises polynucleotide probes of at least 2,000, 4,000, 10,000, 15,000, 20,000, 50,000, 80,000, or 100,000 different nucleotide sequences.

Thus, the array can include polynucleotide probes for most, or all, genes expressed in a cell, tissue, organ or organism. In a specific embodiment, the cell or organism is a mammalian cell or organism. In another specific embodiment, the cell or organism is a human cell or organism. In specific embodiments, the nucleotide sequences of the different polynucleotide probes of the array are specific for at least 50%, at least 75%, at least 80%, at least 85%, at least 90%, at least 95%, or at least 99% of the genes in the genome of the cell or organism. Most preferably, the nucleotide sequences of the different polynucleotide probes of the array are specific for all of the genes in the genome of the cell or organism. In specific embodiments, the polynucleotide probes of the array hybridize specifically and distinguishably to at least 10,000, to at least 20,000, to at least 50,000, to at least 80,000, or to at least 100,000 different polynucleotide sequences. In other specific embodiments, the polynucleotide probes of the array hybridize specifically and distinguishably to at least 90%, at least 95%, or at least 99% of the genes or gene transcripts of the genome of a cell or organism. Most preferably, the polynucleotide probes of the array hybridize specifically and distinguishably to the genes or gene transcripts of the entire genome of a cell or organism.

In specific embodiments, the array has at least 100, at least 250, at least 1,000, or at least 2,500 probes per 1 cm², preferably all or at least 25% or 50% of which are different from each other. In another embodiment, the array is a positionally addressable array (in that the sequence of the polynucleotide probe at each position is known). In another embodiment, the nucleotide sequence of each polynucleotide probe in the array is a DNA sequence. In another embodiment, the DNA sequence is a single-stranded DNA sequence. The DNA sequence may be, e.g., a cDNA sequence, or a synthetic sequence.

When a cDNA molecule that corresponds to an mRNA of a cell is made and hybridized to a microarray under suitable hybridization conditions, the level of hybridization to the site in the array corresponding to any particular gene will reflect the prevalence in the cell of mRNA transcribed from that gene. For example, when detectably labeled (e.g., with a fluorophore) DNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal.

In some embodiments, cDNA molecule populations prepared from RNA from two different cell populations, or tissues, or organs, or whole organisms, are hybridized to the binding sites of the array. A single array can be used to simultaneously screen more than one cDNA sample. For example, in the context of the present invention, a single array can be used to simultaneously screen a cDNA sample prepared from a living thing that has been contacted with an agent (e.g., candidate partial agonist of PPARγ), and the same type of living thing that has not been contacted with the agent. The cDNA molecules in the two samples are differently labeled so that they can be distinguished. In one embodiment, for example, cDNA molecules from a cell population treated with a drug is synthesized using a fluorescein-labeled NTP, and cDNA molecules from a control cell population, not treated with the drug, is synthesized using a rhodamine-labeled NTP. When the two populations of cDNA molecules are mixed and hybridized to the DNA array, the relative intensity of signal from each population of cDNA molecules is determined for each site on the array, and any relative difference in abundance of a particular mRNA detected.

In this representative example, the cDNA molecule population from the drug-treated cells will fluoresce green when the fluorophore is stimulated, and the cDNA molecule population from the untreated cells will fluoresce red. As a result, when the drug treatment has no effect, either directly or indirectly, on the relative abundance of a particular mRNA in a cell, the mRNA will be equally prevalent in treated and untreated cells and red-labeled and green-labeled cDNA molecules will be equally prevalent. When hybridized to the DNA array, the binding site(s) for that species of RNA will emit wavelengths characteristic of both fluorophores (and appear brown in combination). In contrast, when the drug-exposed cell is treated with a drug that, directly or indirectly, increases the prevalence of the mRNA in the cell, the ratio of green to red fluorescence will increase. When the drug decreases the mRNA prevalence, the ratio will decrease.

The use of a two-color fluorescence labeling and detection scheme to define alterations in gene expression has been described, e.g., in Schena et al., 1995, *Science* 270:467-470, which is incorporated by reference in its entirety for all purposes. An advantage of using cDNA molecules labeled with two different fluorophores is that a direct and internally controlled comparison of the mRNA levels corresponding to each arrayed gene in two cell states can be made, and variations due to minor differences in experimental conditions (e.g., hybridization conditions) will not affect subsequent analyses. However, it will be recognized that it is also possible to use cDNA molecules from a single cell, and compare, for example, the absolute amount of a particular mRNA in, e.g., a drug-treated or an untreated cell.

Exemplary microarrays and methods for their manufacture and use are set forth in T. R. Hughes et al., *Nature Biotechnology* 19:342-347 (April 2001), which publication is incorporated herein by reference.

Preparation of nucleic acid molecules for immobilization on microarrays. As noted above, the "binding site" to which a particular, cognate, nucleic acid molecule specifically hybridizes is usually a nucleic acid, or nucleic acid analogue, attached at that binding site. In one embodiment, the binding sites of the microarray are DNA polynucleotides corresponding to at least a portion of some or all genes in an organism's genome. These DNAs can be obtained by, for example, polymerase chain reaction (PCR) amplification of gene segments from genomic DNA, cDNA (e.g., by reverse transcription or RT-PCR), or cloned sequences. Nucleic acid amplification primers are chosen, based on the known sequence of the genes or cDNA, that result in amplification of unique fragments (i.e., fragments that typically do not share more than 10 bases of contiguous identical sequence with any other fragment on the microarray). Computer programs are useful in the design of primers with the required specificity and optimal amplification properties. See, e.g., Oligo version 5.0 (National Biosciences). Typically each gene fragment on the microarray will be between about 50 bp and about 2000 bp, more typically between about 100 bp and about 1000 bp, and usually between about 300 bp and about 800 bp in length.

Nucleic acid amplification methods are well known and are described, for example, in Innis et al., eds., 1990, *PCR Protocols: A Guide to Methods and Applications*, Academic Press Inc., San Diego, Calif., which is incorporated by reference in its entirety for all purposes. Computer controlled robotic systems are useful for isolating and amplifying nucleic acids.

An alternative means for generating the nucleic acid molecules for the microarray is by synthesis of synthetic polynucleotides or oligonucleotides, e.g., using N-phosphonate or phosphoramidite chemistries (e.g., Froehler et al., 1986, *Nucleic Acid Res* 14:5399-5407). Synthetic sequences are typically between about 15 and about 100 bases in length, such as between about 20 and about 50 bases.

In some embodiments, synthetic nucleic acids include non-natural bases, e.g., inosine. Where the particular base in a given sequence is unknown or is polymorphic, a universal base, such as inosine or 5-nitroindole, may be substituted. Additionally, it is possible to vary the charge on the phosphate backbone of the oligonucleotide, for example, by thiolation or methylation, or even to use a peptide rather than a phosphate backbone. The making of such modifications is within the skill of one trained in the art.

As noted above, nucleic acid analogues may be used as binding sites for hybridization. An example of a suitable nucleic acid analogue is peptide nucleic acid (see, e.g., Egholm et al., 1993, *Nature* 365:566-568; see also U.S. Pat. No. 5,539,083).

In another embodiment, the binding (hybridization) sites are made from plasmid or phage clones of genes, cDNAs (e.g., expressed sequence tags), or inserts therefrom (Nguyen et al., 1995, *Genomics* 29:207-209). In yet another embodiment, the polynucleotide of the binding sites is RNA.

Attaching nucleic acids to the solid support. The nucleic acids, or analogues, are attached to a solid support, which may be made, for example, from glass, silicon, plastic (e.g., polypropylene, nylon, polyester), polyacrylamide, nitrocellulose, cellulose acetate or other materials. In general, non-porous supports, and glass in particular, are preferred. The solid support may also be treated in such a way as to enhance binding of oligonucleotides thereto, or to reduce non-specific binding of unwanted substances thereto. For example, a glass support may be treated with polylysine or silane to facilitate attachment of oligonucleotides to the slide.

Methods of immobilizing DNA on the solid support may include direct touch, micropipetting (see, e.g., Yershov et al., *Proc. Natl. Acad. Sci. USA* 93(10):4913-4918 (1996)), or the use of controlled electric fields to direct a given oligonucleotide to a specific spot in the array. Oligonucleotides are typically immobilized at a density of 100 to 10,000 oligonucleotides per $cm^2$, such as at a density of about 1000 oligonucleotides per $cm^2$.

A preferred method for attaching the nucleic acids to a surface is by printing on glass plates, as is described generally by Schena et al., 1995, Science 270:467-470. This method is especially useful for preparing microarrays of cDNA. (See also DeRisi et al., 1996, *Nature Genetics* 14:457-460; Shalon et al., 1996, *Genome Res.* 6:639-645; and Schena et al., *Proc. Natl. Acad. Sci. USA* 93(20):10614-19, 1996.)

In an alternative to immobilizing pre-fabricated oligonucleotides onto a solid support, it is possible to synthesize oligonucleotides directly on the support (see, e.g., Maskos et al., *Nucl. Acids Res.* 21:2269-70, 1993; Lipshutz et al., 1999, *Nat. Genet.* 21(1 Suppl):20-4). Methods of synthesizing oligonucleotides directly on a solid support include photolithography (see McGall et al., *Proc. Natl. Acad. Sci. (USA)*

93:13555-60, 1996) and piezoelectric printing (Lipshutz et al., 1999, *Nat. Genet.* 21(1 Suppl):20-4).

A high-density oligonucleotide array may be employed. Techniques are known for producing arrays containing thousands of oligonucleotides complementary to defined sequences, at defined locations on a surface using photolithographic techniques for synthesis in situ (see Pease et al., 1994, *Proc. Natl. Acad. Sci. USA* 91:5022-5026; Lockhart et al., 1996, *Nature Biotechnol.* 14:1675-80) or other methods for rapid synthesis and deposition of defined oligonucleotides (Lipshutz et al., 1999, *Nat. Genet.* 21(1 Suppl):20-4.).

In some embodiments, microarrays are manufactured by means of an ink jet printing device for oligonucleotide synthesis, e.g., using the methods and systems described by Blanchard in International Patent Publication No. WO 98/41531, published Sep. 24, 1998; Blanchard et al., 1996, *Biosensors and bioelectronics* 11:687-690; Blanchard, 1998, in *Synthetic DNA Arrays in Genetic Engineering*, Vol. 20, J. K. Setlow (ed.), Plenum Press, New York at pages 111-123; U.S. Pat. No. 6,028,189 to Blanchard. Specifically, the oligonucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes).

Other methods for making microarrays, e.g., by masking (Maskos and Southern, 1992, *Nuc. Acids Res.* 20:1679-1684), may also be used. In principle, any type of array, for example dot blots on a nylon hybridization membrane (see Sambrook et al., 1989, *Molecular Cloning—A Laboratory Manual* (2d ed.), Vols. 1-3, Cold Spring Harbor Laboratory, Cold Spring Harbor, N.Y.), could be used, although, as will be recognized by those of skill in the art, very small arrays are typically preferred because hybridization volumes will be smaller.

Signal detection and data analysis. When fluorescently labeled probes are used, the fluorescence emissions at each site of an array can be detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, *Genome Research* 6:639-645, which is incorporated by reference in its entirety for all purposes). In one embodiment, the arrays are scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Shalon et al., 1996, Genome Res. 6:639-645 and in other references cited herein. Alternatively, the fiber-optic bundle described by Ferguson et al., 1996, *Nature Biotechnol.* 14:1681-1684, may be used to monitor mRNA abundance levels at a large number of sites simultaneously.

Signals are recorded and may be analyzed by computer, e.g., using a 12 bit analog to digital board. In some embodiments the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration.

The relative abundance of an mRNA in two biological samples is scored as a perturbation and its magnitude determined (i.e., the abundance is different in the two sources of mRNA tested), or as not perturbed (i.e., the relative abundance is the same). Preferably, in addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

By way of example, two samples, each labeled with a different fluor, are hybridized simultaneously to permit differential expression measurements. If neither sample hybridizes to a given spot in the array, no fluorescence will be seen. If only one hybridizes to a given spot, the color of the resulting fluorescence will correspond to that of the fluor used to label the hybridizing sample (for example, green if the sample was labeled with Cy3, or red, if the sample was labeled with Cy5). If both samples hybridize to the same spot, an intermediate color is produced (for example, yellow if the samples were labeled with fluorescein and rhodamine). Then, applying methods of pattern recognition and data analysis known in the art, it is possible to quantify differences in gene expression between the samples. Methods of pattern recognition and data analysis are described in e.g., International Publication WO 00/24936, which is incorporated by reference herein.

Measuring Gene Expression by Measuring Magnitude of Expression of a Population of Proteins: The magnitude of expression of a first population of genes and/or a second population of genes can be measured, for example, by measuring the magnitude of expression of proteins encoded by the genes.

Any useful method for measuring protein expression patterns can be used. Typically all, or substantially all, proteins are extracted from a living thing, or a portion thereof. The living thing is typically treated to disrupt cells, for example by homogenizing the cellular material in a blender, or by grinding (in the presence of acid-washed, siliconized, sand if desired) the cellular material with a mortar and pestle, or by subjecting the cellular material to osmotic stress that lyses the cells. Cell disruption may be carried out in the presence of a buffer that maintains the released contents of the disrupted cells at a desired pH, such as the physiological pH of the cells. The buffer may optionally contain inhibitors of endogenous proteases. Physical disruption of the cells can be conducted in the presence of chemical agents (e.g., detergents) that promote the release of proteins.

The cellular material may be treated in a manner that does not disrupt a significant proportion of cells, but which removes proteins from the surface of the cellular material, and/or from the interstices between cells. For example, cellular material can be soaked in a liquid buffer, or, in the case of plant material, can be subjected to a vacuum, in order to remove proteins located in the intercellular spaces and/or in the plant cell wall. If the cellular material is a microorganism, proteins can be extracted from the microorganism culture medium.

It may be desirable to include one or more protease inhibitors in the protein extraction buffer. Representative examples of protease inhibitors include: serine protease inhibitors (such as phenylmethylsulfonyl fluoride (PMSF), benzamide, benzamidine HCl, ε-Amino-n-caproic acid and aprotinin (Trasylol)); cysteine protease inhibitors, such as sodium p-hydroxymercuribenzoate; competitive protease inhibitors, such as antipain and leupeptin; covalent protease inhibitors, such as iodoacetate and N-ethylmaleimide; aspartate (acidic) protease inhibitors, such as pepstatin and diazoacetylnorleucine methyl ester (DAN); metalloprotease inhibitors, such as EGTA [ethylene glycol bis(β-aminoethyl ether) N,N,N',N'-tetraacetic acid], and the chelator 1,10-phenanthroline.

The mixture of released proteins may, or may not, be treated to completely or partially purify some of the proteins for further analysis, and/or to remove non-protein contaminants (e.g., carbohydrates and lipids). In some embodiments, the complete mixture of released proteins is analyzed to determine the amount and/or identity of some or all of the proteins. For example, the protein mixture may be applied to a substrate bearing antibody molecules that specifically bind to one or more proteins in the mixture. The unbound proteins are removed (e.g., washed away with a buffer solution), and the amount of bound protein(s) is measured. Representative techniques for measuring the amount of protein using antibodies are described in Harlow and Lane, 1988, *Antibodies: A Laboratory Manual*, Cold Spring Harbor, N.Y., and include such techniques as the ELISA assay. Moreover, protein microarrays can be used to simultaneously measure the amount of a multiplicity of proteins. A surface of the microarray bears protein binding agents, such as monoclonal antibodies specific to a plurality of protein species. Preferably, antibodies are present for a substantial fraction of the encoded proteins, or at least for those proteins whose amount is to be measured. Methods for making monoclonal antibodies are well known (see, e.g., Harlow and Lane, 1988, Antibodies: A Laboratory Manual, Cold Spring Harbor, N.Y.). Protein binding agents are not restricted to monoclonal antibodies, and can be, for example, scFv/Fab diabodies, affibodies, and aptamers. Protein microarrays are generally described by M. F. Templin et al., Protein Microarray Technology, *Trends in Biotechnology*, 20(4):160-166(2002). Representative examples of protein microarrays are described by H. Zhu et al., Global Analysis of Protein Activities Using Proteome Chips, *Science*, 293:2102-2105 (2001); and G. MacBeath and S. L. Schreiber, Printing Proteins as Microarrays for High-Throughput Function Determination, *Science*, 289:1760-1763 (2000).

In some embodiments, the released protein is treated to completely or partially purify some of the proteins for further analysis, and/or to remove non-protein contaminants. Any useful purification technique, or combination of techniques, can be used. For example, a solution containing extracted proteins can be treated to selectively precipitate certain proteins, such as by dissolving ammonium sulfate in the solution, or by adding trichloroacetic acid. The precipitated material can be separated from the unprecipitated material, for example by centrifugation, or by filtration. The precipitated material can be further fractionated if so desired.

By way of example, a number of different neutral or slightly acidic salts have been used to solubilize, precipitate, or fractionate proteins in a differential manner. These include NaCl, $Na_2SO_4$, $MgSO_4$ and $NH_4(SO_4)_2$. Ammonium sulfate is a commonly used precipitant for salting proteins out of solution. The solution to be treated with ammonium sulfate may first be clarified by centrifugation. The solution should be in a buffer at neutral pH unless there is a reason to conduct the precipitation at another pH; in most cases the buffer will have ionic strength close to physiological. Precipitation is usually performed at 0-4° C. (to reduce the rate of proteolysis caused by proteases in the solution), and all solutions should be precooled to that temperature range.

Representative examples of other art-recognized techniques for purifying, or partially purifying, proteins from a living thing are exclusion chromatography, ion-exchange chromatography, hydrophobic interaction chromatography, reversed-phase chromatography and immobilized metal affinity chromatography.

Hydrophobic interaction chromatography and reversed-phase chromatography are two separation methods based on the interactions between the hydrophobic moieties of a sample and an insoluble, immobilized hydrophobic group present on the chromatography matrix. In hydrophobic interaction chromatography the matrix is hydrophilic and is substituted with short-chain phenyl or octyl nonpolar groups. The mobile phase is usually an aqueous salt solution. In reversed phase chromatography the matrix is silica that has been substituted with longer n-alkyl chains, usually $C_8$ (octylsilyl) or $C_{18}$ (octadecylsilyl). The matrix is less polar than the mobile phase. The mobile phase is usually a mixture of water and a less polar organic modifier.

Separations on hydrophobic interaction chromatography matrices are usually done in aqueous salt solutions, which generally are nondenaturing conditions. Samples are loaded onto the matrix in a high-salt buffer and elution is by a descending salt gradient. Separations on reversed-phase media are usually done in mixtures of aqueous and organic solvents, which are often denaturing conditions. In the case of protein purification, hydrophobic interaction chromatography depends on surface hydrophobic groups and is usually carried out under conditions which maintain the integrity of the protein molecule. Reversed-phase chromatography depends on the native hydrophobicity of the protein and is carried out under conditions which expose nearly all hydrophobic groups to the matrix, i.e., denaturing conditions.

Ion-exchange chromatography is designed specifically for the separation of ionic or ionizable compounds. The stationary phase (column matrix material) carries ionizable functional groups, fixed by chemical bonding to the stationary phase. These fixed charges carry a counterion of opposite sign. This counterion is not fixed and can be displaced. Ion-exchange chromatography is named on the basis of the sign of the displaceable charges. Thus, in anion ion-exchange chromatography the fixed charges are positive and in cation ion-exchange chromatography the fixed charges are negative.

Retention of a molecule on an ion-exchange chromatography column involves an electrostatic interaction between the fixed charges and those of the molecule, binding involves replacement of the nonfixed ions by the molecule. Elution, in turn, involves displacement of the molecule from the fixed charges by a new counterion with a greater affinity for the fixed charges than the molecule, and which then becomes the new, nonfixed ion.

The ability of counterions (salts) to displace molecules bound to fixed charges is a function of the difference in affinities between the fixed charges and the nonfixed charges of both the molecule and the salt. Affinities in turn are affected by several variables, including the magnitude of the net charge of the molecule and the concentration and type of salt used for displacement.

Solid-phase packings used in ion-exchange chromatography include cellulose, dextrans, agarose, and polystyrene. The exchange groups used include DEAE (diethylaminoethyl), a weak base, that will have a net positive charge when ionized and will therefore bind and exchange anions; and CM (carboxymethyl), a weak acid, with a negative charge when ionized that will bind and exchange cations. Another form of weak anion exchanger contains the PEI (polyethyleneimine) functional group. This material, most usually found on thin layer sheets, is useful for binding proteins at pH values above their pI. The polystyrene matrix can be obtained with quaternary ammonium functional groups for strong base anion exchange or with sulfonic acid functional groups for strong acid cation exchange. Intermediate and weak ion-exchange materials are also available. Ion-exchange chromatography need not be performed using a column, and can be performed as batch ion-exchange chromatography with the slurry of the stationary phase in a vessel such as a beaker.

Gel filtration is performed using porous beads as the chromatographic support. A column constructed from such beads will have two measurable liquid volumes, the external volume, consisting of the liquid between the beads, and the internal volume, consisting of the liquid within the pores of the beads. Large molecules will equilibrate only with the external volume while small molecules will equilibrate with both the external and internal volumes. A mixture of molecules (such as proteins) is applied in a discrete volume or zone at the top of a gel filtration column and allowed to percolate through the column. The large molecules are excluded from the internal volume and therefore emerge first from the column while the smaller molecules, which can access the internal volume, emerge later. The volume of a conventional matrix used for protein purification is typically 30 to 100 times the volume of the sample to be fractionated. The absorbance of the column effluent can be continuously monitored at a desired wavelength using a flow monitor.

A technique that can be applied to the purification of proteins is High Performance Liquid Chromatography (HPLC). HPLC is an advancement in both the operational theory and fabrication of traditional chromatographic systems. HPLC systems for the separation of biological macromolecules vary from the traditional column chromatographic systems in three ways: (1) the column packing materials are of much greater mechanical strength, (2) the particle size of the column packing materials has been decreased 5- to 10-fold to enhance adsorption-desorption kinetics and diminish band-spreading, and (3) the columns are operated at 10-60 times higher mobile-phase velocity. Thus, by way of non-limiting example, HPLC can utilize exclusion chromatography, ion-exchange chromatography, hydrophobic interaction chromatography, reversed-phase chromatography and immobilized metal affinity chromatography.

An exemplary technique that is useful for measuring the amounts of individual proteins in a mixture of proteins is two dimensional gel electrophoresis. This technique typically involves isoelectric focussing of a protein mixture along a first dimension, followed by SDS-PAGE of the focussed proteins along a second dimension (see, e.g., Hames et al., 1990, *Gel Electrophoresis of Proteins: A Practical Approach*, IRL Press, New York; Shevchenko et al., 1996, *Proc. Nat'l Acad. Sci. U.S.A.* 93:1440-1445; Sagliocco et al., 1996, *Yeast* 12:1519-1533; Lander, 1996, *Science* 274:536-539; and Beaumont et al., *Life Science News*, 7, 2001, Amersham Pharmacia Biotech. The resulting series of protein "spots" on the second dimension SDS-PAGE gel can be measured to reveal the amount of one or more specific proteins in the mixture. The identity of the measured proteins may, or may not, be known; it is only necessary to be able to identify and measure specific protein "spots" on the second dimension gel. Numerous techniques are available to measure the amount of protein in a "spot" on the second dimension gel. For example, the gel can be stained with a reagent that binds to proteins and yields a visible protein "spot" (e.g., Coomassie blue dye, or staining with silver nitrate), and the density of the stained spot can be measured. Again by way of example, all, or most, proteins in a mixture can be measured with a fluorescent reagent before electrophoretic separation, and the amount of fluorescence in some, or all, of the resolved protein "spots" can be measured (see, e.g., Beaumont et al., *Life Science News*, 7, 2001, Amersham Pharmacia Biotech).

Again by way of example, any HPLC technique (e.g., exclusion chromatography, ion-exchange chromatography, hydrophobic interaction chromatography, reversed-phase chromatography and immobilized metal affinity chromatography) can be used to separate proteins in a mixture, and the separated proteins can thereafter be directed to a detector (e.g., spectrophotometer) that detects and measures the amount of individual proteins.

In some embodiments of the invention it is desirable to both identify and measure the amount of specific proteins. A technique that is useful in these embodiments of the invention is mass spectrometry, in particular the techniques of electrospray ionization mass spectrometry (ESI-MS) and matrix-assisted laser desorption/ionization mass spectrometry (MALDI-MS), although it is understood that mass spectrometry can be used only to measure the amounts of proteins without also identifying (by function and/or sequence) the proteins. These techniques overcame the problem of generating ions from large, non-volatile, analytes, such as proteins, without significant analyte fragmentation (see, e.g., R. Aebersold and D. R. Goodlett, Mass Spectrometry in Proteomics, *Chemical Reviews*, 102(2): 269-296 (2001)).

Thus, for example, proteins can be extracted from cells of a living thing and individual proteins purified therefrom using, for example, any of the art-recognized purification techniques described herein (e.g., HPLC). The purified proteins are subjected to enzymatic degradation using a protein-degrading agent (e.g., an enzyme, such as trypsin) that cleaves proteins at specific amino acid sequences. The resulting protein fragments are subjected to mass spectrometry. If the sequence of the complete genome (or at least the sequence of part of the genome) of the living thing from which the proteins were isolated is known, then computer algorithms are available that can compare the observed protein fragments to the protein fragments that are predicted to exist by cleaving the proteins encoded by the genome with the agent used to cleave the extracted proteins. Thus, the identity, and the amount, of the proteins from which the observed fragments are derived can be determined.

Again by way of example, the use of isotope-coded affinity tags in conjunction with mass spectrometry is a technique that is adapted to permit comparison of the identities and amounts of proteins expressed in different samples of the same type of living thing subjected to different treatments (e.g., the same type of living tissue cultured, in vitro, in the presence or absence of a candidate drug) (see, e.g., S. P. Gygi et al., Quantitative Analysis of Complex Protein Mixtures Using Isotope-Coded Affinity Tags (ICATs), *Nature Biotechnology*, 17:994-999(1999)). In an exemplary embodiment of this method, two different samples of the same type of living thing are subjected to two different treatments (treatment 1 and treatment 2). Proteins are extracted from the treated living things and are labeled (via cysteine residues) with an ICAT reagent that includes (1) a thiol-specific reactive group, (2) a linker that can include eight deuteriums (yielding a heavy ICAT reagent) or no deuteriums (yielding a light ICAT reagent), and (3) a biotin molecule. Thus, for example, the proteins from treatment 1 may be labeled with the heavy ICAT reagent, and proteins from treatment 2 may be labelled with the light ICAT reagent. The labeled proteins from treatment 1 and treatment 2 are combined and enzymatically cleaved to generate peptide fragments. The tagged (cysteine-containing) fragments are isolated by avidin affinity chromatography (that binds the biotin moiety of the ICAT reagent). The isolated peptides are then separated by mass spectrometry. The quantity and identity of the peptides (and the proteins from which they are derived) may be determined. The method is also applicable to proteins that do not include cysteines by using ICAT reagents that label other amino acids.

Numerical Values Representing Comparison Results: the magnitudes of the expression of gene populations are compared in the practice of the present invention, and the resulting comparison results are expressed as numerical values. For example, the magnitude of gene expression of a first population of genes, in a cell type, in response to an agent is compared to the magnitude of gene expression of the first population of genes, in the same cell type, in response to a full agonist (functioning as a reference compound) of a target molecule, to produce a first comparison result, wherein the first comparison result is represented by a first numerical value.

Any useful mathematical technique can be used to obtain a numerical value that represents a comparison result obtained in the practice of the present invention. For example, the first and second numerical values used in the practice of the present invention can be represented by the scale factor S as defined in the following exemplary statistical methods:

(1).

$$S = \sum_{i=1}^{n} X_i \Big/ \sum_{i=1}^{n} R_i;$$

wherein n stands for the number of genes and/or proteins.

(2).

$$S = \left(\sum_{i=1}^{n} X_i / R_i\right) \Big/ n$$

(3). Fit a straight line by: $X_i = S \ast R_i$
(4). Least $\chi^2$ fitting: choose a value of S to minimize the $\chi^2$:

$$\chi^2 = \sum_{i=1}^{n} (S \ast R_i - X_i)^2 / (\sigma_{Ri}^2 + \sigma_{Xi}^2)$$

(5). Least square fitting: choose a value of S to minimize the $Q^2$:

$$Q^2 = \sum_{i=1}^{n} (S \ast R_i - X_i)^2$$

In the foregoing formulae, Ri, $\sigma_{Ri}$ stand for the log(Ratio) and error of the log(Ratio) for ith gene, or ith protein, from the template experiment; Xi and $\sigma_{Xi}$ stand for the log(Ratio) and error of log(Ratio) of the same gene, or protein, expressed in response to a candidate agent. The template experiment is the experiment that yields gene expression data, or protein expression data, in response to an agent having a known biological activity.

Almost all statistical "fitting" algorithms can be used to generate a scale factor for comparing the expression responses (transcriptional, proteomic or metabolic) produced by an agent with the expression responses produced by a reference agent.

Another exemplary method that can be used to analyze or compare gene expression profiles is averaging. For example, the average expression value for each gene, in a first or second population of genes, response to the candidate agent is divided by the average expression value for each gene in response to the reference agent to yield a percentage expression value for each gene. The mean of all of the percentage expression values is calculated and is the comparison value for the candidate agent. Similarly, for example, if protein expression levels are being measured, the average expression value for each protein in response to the candidate agent is divided by the average expression value for each protein in response to the reference agent to yield a percentage expression value for each protein. The mean of all of the percentage expression values is calculated and is the comparison value for the candidate agent.

Standard statistical techniques can be found in statistical texts, such as *Modern Elementary Statistics*, John E. Freund, 7th edition, published by Prentice-Hall; and *Practical Statistics for Environmental and Biological Scientists*, John Townend, published by John Wiley & Sons, Ltd.

Using the First Numerical Value and the Second Numerical Value: In the practice of the present invention the first numerical value and the second numerical value are used to determine whether the agent is more like a partial agonist of the target molecule than a full agonist of the same target molecule. Typically, an agent is more like a partial agonist of a target molecule than a full agonist of the same target molecule if the comparison result for the first population of genes is significantly greater than the comparison result for the second population of genes (i.e., the first numerical value for the first population of genes is significantly greater than the second numerical value for the second population of genes).

For example, a chi-square fitting algorithm can be used to compute first and second comparison results (each represented by a numerical value) for several reference full agonists (or, for example, for several different doses of a single full agonist). The first and second comparison results for each reference agonist (or dosage) are plotted on an x-y graph (such as the x-y graph shown in THE FIGURE); the first comparison results are plotted on the y-axis, and the second comparison results are plotted on the x-axis. A best fitting straight line for these data is plotted using a standard statistical fitting technique, which may also provide the confidence intervals for the plotted data. If the intersection of the first and second numerical results, for a candidate agent, on the x-y graph is located at a point above the best fitting straight line, and the distance between the point and the best fitting straight line is statistically larger than the confidence interval for the best fitting straight line, then the agent is more like a partial agonist than an agonist of the target molecule.

Again by way of example, the ratio of the first numerical value to the second numerical value can be calculated. If the ratio of the first numerical value to the second numerical value is significantly greater than a defined value (e.g., greater than 1) then the agent is more like a partial agonist than an agonist of the target molecule.

Ranking Candidate Compounds: The methods of the present invention can include the step of ranking agents wherein the position of the agent in the rank indicates the level of similarity of the agent to a partial agonist of a target molecule. For example, the ratio of the first numerical value to the second numerical value can be calculated for each agent. The agents can then be ranked based on the value of the foregoing ratio, wherein the agent having the largest ratio is ranked at the top and is considered to be most like a partial agonist of a target molecule, and the candidate having the smallest ratio is ranked at the bottom and is considered to be least like a partial agonist of the same target molecule. Some of the ranked agents may be chosen for further study. For example, agents ranked at or near the top may be chosen for further study.

Screening for Compounds that Reduce Blood Plasma Glucose Levels: In another aspect, the present invention provides methods to screen compounds to identify a candidate compound that may reduce blood plasma glucose concentration in a mammal (e.g., a human being). The methods of this aspect of the invention each include the step of contacting a cell, of a cell type, with a compound and determining whether the compound causes a significant increase in the level of expression of a population of 29 genes that each hybridize under stringent conditions to a different member of the group of nucleic acid molecules consisting of SEQ ID NOS:1-29, wherein if the compound causes a significant increase in the level of expression of the population of 29 genes then the compound is selected as a candidate compound that may reduce blood plasma glucose concentration in a mammal. Selected compounds may be administered to a mammal to determine whether the selected compounds reduce blood plasma glucose concentration in the mammal.

This aspect of the invention relies, at least in part, on the discovery that the level of expression of the population of genes corresponding to SEQ ID NOS:1-29 is significantly increased by partial agonists of PPARγ. Partial agonists of PPARγ have the property of being able to reduce blood plasma glucose concentration in a mammal when administered to the mammal in an effective amount. Thus, a significant increase in the level of expression of the genes corresponding to SEQ ID NOS:1-29 correlates with a reduction in blood plasma glucose concentration in a mammal.

SEQ ID NOS:1-29 are cDNA molecules that correspond to 29 different genes as described herein. Each of the 29 genes hybridizes under stringent conditions to its corresponding cDNA having a nucleic acid sequence set forth in one of SEQ ID NOS:1-29, but not to any other of the 29 cDNAs having the sequences set forth in SEQ ID NOS:1-29. In this context, stringent hybridization conditions are at least of 5×SSC at 55° C. for one hour. Other exemplary stringent hybridization conditions are 5×SSC at 65° C. for one hour. The abbreviation "SSC" refers to a buffer used in nucleic acid hybridization solutions. One liter of the 20× (twenty times concentrate) stock SSC buffer solution (pH 7.0) contains 175.3 g sodium chloride and 88.2 g sodium citrate.

In the practice of this aspect of the invention, the level of expression of the aforementioned population of 29 genes in response to a compound is typically compared to the level of expression of the aforementioned population of 29 genes in a control cell of the same cell type, wherein the control cell has been treated identically to the cell contacted with the compound, except that the control cell has not been contacted with the compound. If the level of expression of the aforementioned population of 29 genes is significantly higher in the cell contacted with the compound, compared to the level of expression of the aforementioned population of 29 genes in the control cell, then the compound is typically selected as a candidate compound that may reduce blood plasma glucose concentration in a mammal.

The selected compound is typically subjected to further study to determine whether the compound reduces blood plasma glucose concentration in a mammal (e.g., a controlled experiment is conducted wherein the selected compound is administered to a group of mammals, such as rats or mice, and the effect of the compound on blood plasma glucose concentration is determined).

The level of expression of the aforementioned population of 29 genes in a cell (or population of cells) may be measured, for example, by any of the gene expression measurement techniques described herein. For example, any of the statistical techniques described in the portion of the present patent application entitled "Numerical Values Representing Comparison Results" can be used to compare the level of expression of the aforementioned population of 29 genes in a cell (or population of cells) contacted with a compound, with the level of expression of the aforementioned population of 29 genes in a control cell (or population of control cells) not contacted with the compound, and to determine whether a significant difference exists between the levels of gene expression in the contacted and uncontacted cell(s).

The methods of this aspect of the present invention may include the additional step of determining the ratio of gene expression of the aforementioned population of 29 genes, to the ratio of gene expression of a population of 11 genes, wherein the 11 genes each hybridize under stringent conditions to a different member of the group of nucleic acid molecules consisting of SEQ ID NOS:30-40. SEQ ID NOS: 30-40 are cDNA molecules that correspond to 11 different genes as described herein. In this context, stringent hybridization conditions are at least 5×SSC at 55° C. for one hour. Other exemplary stringent hybridization conditions are 5×SSC at 65° C. for one hour.

A multiplicity of candidate compounds may be ranked based on the ratio of gene expression of the 29 genes to the 11 genes, wherein compounds producing a ratio higher than a selected ratio value are further tested to determine whether the compounds reduce blood plasma glucose concentration in a mammal.

The following examples merely illustrate the best mode now contemplated for practicing the invention, but should not be construed to limit the invention.

EXAMPLE 1

This example describes the identification of an efficacy-related population of genes (SEQ ID NOS:1-29) and a toxicity-related population of genes (SEQ ID NOS:30-40) that can be used to determine whether an agent is more like a partial agonist of PPARγ than a full agonist of PPARγ. This Example also discloses the sequences of a population of 29 oligonucleotide probes (SEQ ID NOS:41-69) that are hybridization probes for the 29 genes of the efficacy-related population of genes (SEQ ID NOS:1-29), and the sequences of a population of 17 oligonucleotide probes (SEQ ID NOS:70-86) that are hybridization probes for the 11 genes of the toxicity-related population of genes (SEQ ID NOS:30-40).

Table 1 shows the GENBANK® accession number and gene name for each member of the efficacy-related population of genes.

TABLE 1

| Accession number | Gene Name | Gene SEQ ID NO | Probe SEQ ID NO |
|---|---|---|---|
| NM_016740 | S100a11 | 1 | 41 |
| AK020722 | 1110003F05Rik | 2 | 42 |
| AK004305 | D10Ertd749e | 3 | 43 |

TABLE 1-continued

| Accession number | Gene Name | Gene SEQ ID NO | Probe SEQ ID NO |
|---|---|---|---|
| NM_025662 | Pigk | 4 | 44 |
| AK016205 | Dixdc1 | 5 | 45 |
| AK011301 | Nap1l1 | 6 | 46 |
| AK010169 | 2310075E07Rik | 7 | 47 |
| AK014794 | Zmynd17 | 8 | 48 |
| AK014487 | Sdsl | 9 | 49 |
| AK007076 | 1700095D18Rik | 10 | 50 |
| NM_011598 | Fabp9 | 11 | 51 |
| AK010321 | 2410001C21Rik | 12 | 52 |
| NM_026519 | 2610318K02Rik | 13 | 53 |
| BF318286 | 3110043O21Rik | 14 | 54 |
| AK004659 | Cfl2 | 15 | 55 |
| NM_028333 | Angptl1 | 16 | 56 |
| BB326776 | BB326776 | 17 | 57 |
| AK010936 | Ak2 | 18 | 58 |
| AK009798 | 2310044E02Rik | 19 | 59 |
| NM_010918 | Nktr | 20 | 60 |
| NM_019930 | Ranbp9 | 21 | 61 |
| AK003201 | 1110001A23Rik | 22 | 62 |
| AK010201 | 2310076K21Rik | 23 | 63 |
| M20497 | Fabp4 | 24 | 64 |
| BE457517 | Ppp2r5a | 25 | 65 |
| M13264 | Fabp4 | 26 | 66 |
| AF011360 | Rgs7 | 27 | 67 |
| U53228 | Rora | 28 | 68 |
| L23108 | Cd36 | 29 | 69 |

Table 2 shows the GENBANK® accession number and gene name for each member of the toxicity-related population of genes.

TABLE 2

| Accession number | Gene Name | Gene SEQ ID NO | Probe SEQ ID NO |
|---|---|---|---|
| BC019496 | Agt | 30 | 70 |
| AK005080 | Suclg1 | 31 | 71 |
| AK075624 | Slc25a20 | 32 | 72 |
| BC005792 | Pte1 | 33 | 73 |
| NM_024446 | Nudt7 | 34 | 74 |
| BC009134 | D14Wsu89e | 35 | 75 |
| Z71189 | Acadvl | 36 | 76 |
|  |  |  | 77 |
|  |  |  | 78 |
| D13664 | Postn | 37 | 79 |
| D50834 | Cyp4b1 | 38 | 80 |
|  |  |  | 81 |
|  |  |  | 82 |
| U37501 | Lama5 | 39 | 83 |
| X89998 | Hsd17b4 | 40 | 84 |
|  |  |  | 85 |
|  |  |  | 86 |

The magnitude of expression of a first population of genes (e.g., an efficacy-related population of genes) useful in the practice of the present invention is consistently more regulated by partial agonists of a target molecule than by full agonists of the same target molecule. In the present Example, genes for inclusion in an efficacy-related population of genes were consistently more regulated by partial agonists of PPARγ than by full agonists of PPARγ.

The criteria applied to determining that a gene was consistently more regulated by partial agonists of PPARγ than by full agonists of PPARγ were: (1) the ratio of the magnitude of gene expression caused by the partial agonists over the magnitude of gene expression caused by the full agonists was consistently larger than the average of such ratio determined by using all robust signature genes (wherein signature genes are genes that show greater regulation by the partial agonists than by the full agonists); and (2) the ratio of the magnitude of gene expression caused by the partial agonists of PPARγ over the ratio of gene expression caused by the full agonists of PPARγ was consistently equal to or larger than the ratio of the endpoint efficacy (Glucose Correction) effect caused by the partial agonists of PPARγ to the endpoint efficacy (Glucose Correction) caused by the full agonists of PPARγ.

Genetically altered, diabetic, mice (db/db strain, available from the Jackson Laboratory, Bar Harbor, Me., U.S.A., as strain C57B1/KFJ, and described by Chen et al., *Cell* 84:491-495 (1996), and by Combs et al., *Endocrinology* 142:998-1007 (2002)) were treated with two PPARγ full agonists, and 7 PPARγ partial agonists. The compounds were administered to the animals daily. Serum glucose measurements were taken at the onset (before dosing) and 24 hr after the 7th dose. Glucose Correction was computed as 100-(db Treated With Drug-Lean Treated With Vehicle)/(dbTreated With Vehicle-Lean Treated With Vehicle)*100, all using Day7 glucose measurements. Glucose Lowering was computed as (Day7-Day0)/Day0 for each treatment. Epididymal white adipose tissue (EWAT tissue) was removed from the treated mice 6 hours after the 8th dose and was subsequently profiled using Agilent v1.2 25K mouse DNA microarrays.

Table 3 shows the identity and dosage of the two PPARγ full agonists, and 7 PPARγ partial agonists administered to the mice.

TABLE 3

| Chemical Name | Type | Doses (mg/kg/day) |
|---|---|---|
| 5-(4-{2-[methyl(pyridin-2-yl)amino]ethoxy}benzyl)-1,3-thiazolidine-2,4-dione | Full (Rosiglitazone) | 3, 30, 100 |
| {2-[2-(4-phenoxy-2-propylphenoxy)ethyl]-1H-indol-5-yl}acetic acid | Full | 3, 30 |
| sodium (2R)-2-(3-{[3-(4-chlorophenoxy)-2-methyl-6-(trifluoromethoxy)-1H-indol-1-yl]methyl}phenoxy)butanoate | Partial | 3, 20 |
| sodium (2R)-2-(4-chloro-3-{[3-(6-methoxy-1,2-benzisoxazol-3-yl)-2-methyl-6-(trifluoromethoxy)-1H-indol-1-yl]methyl}phenoxy)propanoate | Partial | 10, 30 |
| sodium (2R)-2-(4-chloro-3-{[3-(6-methoxy-1,2-benzisoxazol-3-yl)-2-methyl-6-(trifluoromethoxy)-1H-indol-1-yl]methyl}phenoxy)butanoate | Partial | 5, 20 |
| sodium (2S)-2-(2-chloro-5-{[3-(4-chlorophenoxy)-2-methyl-6-(trifluoromethoxy)-1H-indol-1-yl]methyl}phenoxy)propanoate | Partial | 10, 50 |
| 5-chloro-1-(4-chlorobenzyl)-3-(phenylthio)-1H-indole-2-carboxylic acid | Partial | 10, 30 |
| Partial Agonist No: 1 | Partial | 10, 30 |
| sodium (2S)-2-(3-{[3-(4-chlorophenoxy)-2-methyl-6-(trifluoromethoxy)-1H-indol-1-yl]methyl}phenoxy)propanoate | Partial | 5, 30 |

The first population of genes was selected using the following procedures:

(1) Selecting robust efficacy-related genes: Genes were selected that had expression that was significantly correlated (pvalue for the correlation <0.01) with the efficacy endpoint (Glucose correction). The selected genes were then compared to genes that showed robust regulation (pvalue for replicate combined logRatio <0.01, and fold change >1.2×) in at least two out of four of the following animal groups that were each treated with one of the following four high doses of the PPARγ full agonist rosiglitazone: rosiglitazone administered at a dosage of 30 mg/kg/day; rosiglitazone administered at a dosage of 100 mg/kg/day; rosiglitazone administered at a dosage of 30 mg/kg/day (in the second batch of the profiling experiment); and {2-[2-(4-phenoxy-2-propylphenoxy)ethyl]-1H-indol-5-yl}acetic acid administered at a dosage of 30 mg/kg/day. 1205 genes were identified using this method.

(2) Computing a fullness score for each treatment: Replicate gene expression profiles of mice treated with 100 mg/kg/day rosiglitazone were combined (error weighted average) into one template experiment. The 1205 genes identified in step (1) were further compared with the robust signature genes that had a replicate combined pvalue <0.01, and a fold change in the magnitude of gene expression >1.3× in the template experiment. 610 genes were identified using this method.

Chi-square fitting of the expression data of the selected 610 genes was used to obtain a fullness score for each treatment (i.e., for each dosage of each PPARγ full or partial agonist). The chi-square fitting formula was:

$$\chi^2 = \sum_{i=1}^{n} (S * R_i - X_i)^2 / (\sigma_{R_i}^2 + \sigma_{X_i}^2)$$

Where Ri, σRi stand for the logRatio and error for logRatio of the full template. Xi and σXi stand for the logRatio and error for logRatio of the tested compound. This chi square fitting method is described, for example, by W. Press et al., Numerical Recipes in C, Chapter 14, Cambridge University Press (1991).

The fullness score is represented by S in the above formula, and is a measure of the average ratio of the level of gene expression of the 610 genes caused by a test compound (e.g., PPARγ partial agonist) versus the level of gene expression caused by the template compound (e.g., PPARγ full agonist).

(3) Using the fullness score to select genes having expression that was more regulated by PPARγ partial agonists than by the template compound: animals were selected that had been treated with a PPARγ partial agonist, and that had a fullness score (S) greater than 0.3. Genes that were expressed in the selected animals were selected wherein the ratio of regulation (logRatio) by the PPARγ partial agonist over regulation by the template compound was larger than the fullness score in more than 80% of the selected animals.

(4) Using efficacy end point data to select genes that were more regulated by PPARγ partial agonists than by the template compound: animals were selected that had been treated with PPARγ partial agonists and that had the following efficacy end point measurements: Glucose Correction >40% and Glucose Lowering >40%. Genes were then selected wherein the regulation (logRatio) of gene expression by the PPARγ partial agonists over the regulation (logRatio) of gene expression by the template compound was equal to or larger than the ratio of the glucose correction by the PPARγ partial agonists over the glucose correction by the template compound in more than 80% of the selected animals.

(5) Identification of Efficacy-related Genes: 29 genes (SEQ ID NOS:1-29) were identified that occurred in each of the gene populations identified in foregoing steps (1), (3) and (4). These 29 genes (SEQ ID NOS:1-29) consistently showed more regulation by PPARγ partial agonists than by PPARγ full agonists.

(6) Similar criteria were applied to the Sprague Dawley Rat profiling experiments to select a second population of genes that consistently showed less regulation by PPARγ partial agonists than by PPARγ full agonists. The rat animal model was used because it is believed to be a better animal model to study toxicity effects of PPARγ agonists. The selected rat genes were then mapped to mouse sequences and 11 homologous mouse genes (SEQ ID NOS:30-40) were obtained, so that the first (efficacy-related) populations of genes (SEQ ID NOS:1-29), and the second (toxicity-related) populations of genes (SEQ ID NOS:30-40) can both be used to study the effects of PPARγ agonists and PPARγ partial agonists in the same model organism (mice).

EXAMPLE 2

This example shows the use of the efficacy-related population of genes (SEQ ID NOS:1-29) and the toxicity-related population of genes (SEQ ID NOS:30-40) to distinguish between representative PPARγ partial agonists and representative PPARγ full agonists.

Experiment: 3T3-L1 cells were induced to fully differentiate into adipocytes by the protocol described in *Endocrinology* 143(6):2106-18 (2002). At day 8, cells were incubated with the testing compound for 24 hours.

The testing compounds included eleven partial PPARγ agonists, two full PPARγ agonists, and two compounds that did not interact with PPARγ: compound L-023499 (a liver X-receptor), and compound L-634273 (a PPARα agonist). The testing compounds and their dosages are set forth in Table 4.

TABLE 4

| Chemical Name | Type | Dose (μM) |
|---|---|---|
| 5-(4-{2-[methyl(pyridin-2-yl)amino]ethoxy}benzyl)-1,3-thiazolidine-2,4-dione) | Rosiglitazone | 1, 10 |
| 5-{4-[2-(5-ethylpyridin-2-yl)ethoxy]benzyl}-1,3-thiazolidine-2,4-dione | Full | 10, 30 |
| sodium (2R)-2-(4-chloro-3-{[3-(6-methoxy-1,2-benzisoxazol-3-yl)-2-methyl-6-(trifluoromethoxy)-1H-indol-1-yl]methyl}phenoxy)propanoate | Partial | 1, 10 |
| Partial Agonist No: 2 | Partial | 1, 10 |
| Partial Agonist No: 3 | Partial | 1, 10 |
| Partial Agonist No: 4 | Partial | 1, 10 |
| Partial Agonist No: 5 | Partial | 1, 10 |
| Partial Agonist No: 6 | Partial | 1, 10 |
| Partial Agonist No: 7 | Partial | 1, 10 |
| Partial Agonist No: 8 | Partial | 1, 10 |
| Partial Agonist No: 9 | Partial | 1, 10 |
| Partial 9 | Partial | 1, 10 |
| Partial Agonist No: 10 | Partial | 1, 10 |
| WY14643 ({4-chloro-6-[(2,3-dimethylphenyl)amino]pyrimidin-2-yl}thio)acetic acid | PPAR alpha | 1, 10 |
| 3-(3-{[7-propyl-3-(trifluoromethyl)-1,2-benzisoxazol-6-yl]oxy}propyl)dihydropyrimidine-2,4(1H,3H)-dione | LXR agonist | 1, 10 |

Analysis: The following method was used to distinguish between PPARγ partial agonists and PPARγ full agonists using the efficacy-related population of genes (SEQ ID NOS: 1-29) and the toxicity-related population of genes (SEQ ID NOS:30-40) described in Example 1.

(1) A gene expression score was computed using the expression data of the population of 29 efficacy-related genes (SEQ ID NOS:1-29). Replicate gene expression profiles from 3T3L1 adipocytes treated with rosiglitazone (at a concentration of 10 μM) were combined (error weighted average) into one template experiment. The expression data from the 29 efficacy-related genes (SEQ ID NOS:1-29) were subjected to chi-square fitting (as described in step (2) of Example 1) to obtain a gene score (GS 1) for each treatment.

(2) Step (1) of this Example was repeated using the 11 toxicity-related genes (SEQ ID NOS:30-40) to obtain a gene score (GS2) for each treatment.

(3) The FIGURE shows the comparison plot that was generated using the two gene scores (GS1-vs-GS2). The comparison plot shows that the PPARγ full agonists distributed along the 45 degree diagonal line, while the PPARγ partial agonists distributed above the diagonal line. The vehicle samples and compounds that were not PPARγ agonists, or PPARγ partial agonists, distributed around zero, or below the diagonal line.

The observed distinction between PPARγ partial agonists and PPARγ full agonists is independent of the dosage. The results of additional experiments (data not shown) demonstrated that PPARγ full agonists, used at medium dosage, also distributed along the diagonal line, and that the PPARγ partial agonists and PPARγ full agonists can be distinguished regardless of dosage.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of determining whether an agent is more like a partial agonist of a target molecule than a full agonist of the same target molecule, the method comprising the steps of:
   (a) comparing the magnitude of gene expression of a first population of genes, in cells of a cell type, in response to an agent to the magnitude of gene expression of the first population of genes, in cells of the cell type, in response to a full agonist of a target molecule, to produce a first comparison result, wherein the first population of genes is an efficacy-related population of genes that consists of a population of 29 genes that each hybridize under stringent conditions to a different member of the group of nucleic acid molecules consisting of SEQ ID NOS:1-29, and wherein the first comparison result is represented by a first numerical value;
   (b) comparing the magnitude of gene expression of a second population of genes, in cells of the cell type, in response to the agent to the magnitude of gene expression of the second population of genes, in cells of the cell type, in response to the full agonist of the target molecule, to produce a second comparison result, wherein the second population of genes is a toxicity-related population of genes that consists of a population of 11 genes that each hybridize under stringent conditions to a different member of the group of nucleic acid molecules consisting of SEQ ID NOS:30-40, and wherein the second comparison result is represented by a second numerical value; and
   (c) using the first numerical value and the second numerical value to determine whether the agent is more like a partial agonist of the target molecule than the full agonist of the target molecule, wherein any part of step (a) can occur before, during, or after any part of step (b),
   wherein steps (a), (b), and (c) are performed by a suitably programmed computer.

2. The method of claim 1 wherein gene expression is measured by measuring RNA expression.

3. The method of claim 1 wherein gene expression is measured by measuring mRNA expression.

4. The method of claim 1 wherein gene expression is measured by measuring protein expression.

5. The method of claim 1 wherein chi-square analysis is used to compare the magnitudes of expression of the gene populations to obtain the first and second numerical values.

6. The method of claim 1 wherein the determination is made that the agent is more like the partial agonist than the full agonist if the comparison result for the first population of genes is significantly greater than the comparison result for the second population of genes.

7. The method of claim 1 wherein the first and second numerical values are compared on a comparison plot to determine whether the agent is more like the partial agonist than the full agonist of the target molecule.

8. The method of claim 1 wherein the ratio of the first numerical value to the second numerical value is used to determine whether the agent is more like the partial agonist than the full agonist of the target molecule.

9. The method of claim 8 wherein the determination is made that the agent is more like the partial agonist than the full agonist if the ratio of the first numerical value to the second numerical value is greater than a selected value.

10. The method of claim 8 wherein the determination is made that the agent is more like the partial agonist than the full agonist if the ratio of the first numerical value to the second numerical value is greater than one.

11. The method of claim 1 wherein the determination is made that the agent is more like the partial agonist than the full agonist if the comparison result for the efficacy-related population of genes is significantly greater than the comparison result for the toxicity-related population of genes.

12. The method of claim 1 wherein a ratio of the first numerical value to the second numerical value is calculated, and the determination is made that the agent is more like the partial agonist than the full agonist if the ratio is greater than one.

13. The method of claim 1 wherein a ratio of the second numerical value to the first numerical value is calculated, and the determination is made that the agent is more like the partial agonist than the full agonist if the ratio is less than one.

14. The method of claim 1 wherein the target molecule is a PPARγ molecule.

15. The method of claim 14 wherein the determination is made that the agent is more like a partial PPARγ agonist than a full PPARγ agonist if the comparison result for the efficacy-related population of genes is significantly greater than the comparison result for the toxicity-related population of genes.

16. The method of claim 1 further comprising the step of ranking a multiplicity of agents to form a rank of agents, wherein the position of an agent in the rank indicates the level of similarity of the agent to a partial agonist of the target molecule.

17. The method of claim 1 wherein the cells are contacted with a non-saturating amount of the agent before the magnitude of gene expression of the first population of genes and the magnitude of gene expression of the second population of genes are measured.

18. The method of claim 1 wherein the cells are contacted with a saturating amount of the agent before the magnitude of gene expression of the first population of genes and the magnitude of gene expression of the second population of genes are measured.

19. A method of determining whether an agent is more like a partial agonist of a PPARγ molecule than a full agonist of the PPARγ molecule, the method comprising the steps of:
   (a) comparing the magnitude of gene expression, in cells of a cell type, of a first population of 29 genes, that each hybridize under stringent conditions to a different member of the group of nucleic acid molecules consisting of SEQ ID NOS:1-29, in response to an agent, to the magnitude of gene expression, in cells of the cell type, of the first population of genes in response to a full agonist of a PPARγ molecule, to produce a first comparison result, wherein the first comparison result is represented by a first numerical value;

(b) comparing the magnitude of gene expression, in cells of the cell type, of a second population of 11 genes, that each hybridize under stringent conditions to a different member of the group of nucleic acid molecules consisting of SEQ ID NOS:30-40, in response to the agent, to the magnitude of gene expression of the second population of genes, in cells of the cell type, in response to the full agonist of the PPARγ molecule, to produce a second comparison result, wherein the second comparison result is represented by a second numerical value; and (c) using the first numerical value and the second numerical value to determine whether the agent is more like a partial agonist of the PPARγ molecule than the full agonist of the PPARγ molecule, wherein any part of step (a) can occur before, during, or after any part of step (b), wherein steps (a), (b), and (c) are performed by a suitably programmed computer.

* * * * *